US011920187B2

(12) United States Patent
Bakker et al.

(10) Patent No.: US 11,920,187 B2
(45) Date of Patent: Mar. 5, 2024

(54) VARIN MARKERS

(71) Applicant: Phylos Bioscience, Inc., Portland, OR (US)

(72) Inventors: Erica Bakker, Portland, OR (US); Alisha Holloway, Portland, OR (US); Kayla Hardwick, Portland, OR (US)

(73) Assignee: Phylos Bioscience, Inc., Portland, OR (US)

( * ) Notice: Subject to any disclaimer, the term of this patent is extended or adjusted under 35 U.S.C. 154(b) by 0 days.

(21) Appl. No.: 17/822,115

(22) Filed: Aug. 24, 2022

(65) Prior Publication Data

US 2023/0014963 A1 Jan. 19, 2023

Related U.S. Application Data

(63) Continuation of application No. PCT/US2021/044908, filed on Aug. 6, 2021.

(60) Provisional application No. 63/064,874, filed on Aug. 12, 2020.

(51) Int. Cl.
*C12Q 1/6827* (2018.01)
*C12Q 1/6858* (2018.01)

(52) U.S. Cl.
CPC ......... *C12Q 1/6827* (2013.01); *C12Q 1/6858* (2013.01); *C12Q 2600/156* (2013.01)

(58) Field of Classification Search
CPC ................ C12Q 1/6827; C12Q 1/6858; C12Q 2600/13; A01H 6/28
See application file for complete search history.

(56) References Cited

U.S. PATENT DOCUMENTS

| 4,683,195 A | 7/1987 | Mullis et al. |
| 4,683,202 A | 7/1987 | Mullis |

FOREIGN PATENT DOCUMENTS

| WO | WO-2016197258 A1 * | 12/2016 | ............. C07H 21/04 |
| WO | WO-2022180532 A1 * | 9/2022 | |

OTHER PUBLICATIONS

Woods et al. G3. 2023. 13(2):jkac209. (Year: 2023).*
McKernan et al. "Sequence and annotation of 42 cannabis genomes reveals extensive copy number variation in cannabinoid synthesis and pathogen resistance genes". 2020. Retrieved on Jun. 5, 2023 from the internet: https://www.biorxiv.org/content/10.1101/2020.01.03.894428v1.full. (Year: 2020).*
Zhang et al. Frontiers in Genetics. 2020. 11:958. (Year: 2020).*
Henry et al. Journal of Cannabis Research. 2020. 2:26, pp. 11. (Year: 2020).*
Meijer et al. Genetics. 2003. 163:335-346. (Year: 2003).*
Welling et al. Euphytica. 2016. 208:466-475. (Year: 2016).*
Datwyler et al. J Forensic Sci. 2006. 51(2):371-375. (Year: 2006).*
Welling et al. Scientific Reports. 2020. 10:18643, pp. 14. (Year: 2020).*
Lynch et al. Critical Reviews in Plant Sciences. 2016. 35(5-6):349-363. (Year: 2016).*
Cascini, Fidelia et al 2019 "Highly Predictive Genetic markers distinguish Drug-Type from Fiber-Type *Cannabis sativa* L." Plants 8 , 496.
Welling et al 2016 "Characterisation of cannabinoid composition in a diverse *Cannabis sativa* L. germplasm collection" Euphytica 208:463-475.
El-Din El-Assal, S.J.L et al. 2004. "DISTORTED2 Encodes an ARPC2 Subunit of the Putative *Arabidopsis* ARP2/3 Complex." The Plant Journal 38(3):526-38. doi: 10.1111/j.1365-313X.2004.02065.x.
Guan, X., et al. 2020 "Dual-Localized Enzymatic Components Constitute the Fatty Acid Synthase Systems in Mitochondria and Plastids." Plant Physiology 183(2):517-29. doi: 10.1104/pp. 19.01564.
Hofmann, N.R. 2017. "The Who, What, and Where of Plant Polyprenol Biosynthesis Point to Thylakoid Membranes and Photosynthetic Performance." The Plant Cell 29(7):1552-53. doi: 10.1105/tpc.17.00559.
Hu, Z., et al. 2021. "*Escherichia coli* FabG 3-Ketoacyl-ACP Reductase Proteins Lacking the Assigned Catalytic Triad Residues Are Active Enzymes." Journal of Biological Chemistry 296:100365. doi: 10.1016/j.jbc.2021.100365.
Janßen, H., et al. 2014. "Fatty Acid Synthesis in *Escherichia coli* and Its Applications towards the Production of Fatty Acid Based Biofuels." Biotechnology for Biofuels 7(1):7. doi: 10.1186/1754-6834-7.
Jawed, K., et al. 2016. "Engineered Production of Short Chain Fatty Acid in *Escherichia coli* Using Fatty Acid Synthesis Pathway" edited by P. C. Cirino. PLOS ONE 11(7):e0160035. doi: 10.1371/journal.pone.0160035.
Livingston, S., et al. 2019. "Cannabis Glandular Trichomes Alter Morphology and Metabolite Content during Flower Maturation." The Plant Journal 20.
Moreno-Perez, A., et al . . . 2021. "Genome-Wide Mapping of Histone H3 Lysine 4 Trimethylation (H3K4me3) and Its Involvement in Fatty Acid Biosynthesis in Sunflower Developing Seeds." Plants 10(4):706. doi: 10.3390/plants10040706.
Nomura, C.T., et al. 2005. "Expression of 3-Ketoacyl-Acyl Carrier Protein Reductase ( FabG) Genes Enhances Production of Polyhydroxyalkanoate Copolymer from Glucose in Recombinant *Escherichia coli* JM109." Applied and Environmental Microbiology 71(8):4297-4306. doi: 10.1128/AEM.71.8.4297-4306.2005.
Price, A.C., et al. 2004. "Cofactor-Induced Conformational Rearrangements Establish a Catalytically Competent Active Site and a Proton Relay Conduit in FabG." Structure 12(3):417-28. doi: 10.1016/j.str.2004.02.008.

(Continued)

*Primary Examiner* — Joseph G. Dauner
(74) *Attorney, Agent, or Firm* — Klarquist Sparkman, LLP

(57) ABSTRACT

Provided herein is the identification of markers associated with THCV, THCVA, CBDV, CBDVA, CBGV, or CBGVA production in *Cannabis* plants and their use in selecting *Cannabis* plants having modified THCV, THCVA, CBDV, CBDVA, CBGV, or CBGVA activity. The markers are useful for breeding plants having modified varin activity, including elevated THCV levels, by obtaining nucleic acids, detecting one or more markers that indicate modified varin activity, and establishing plant lines having such characteristics.

10 Claims, 3 Drawing Sheets

Specification includes a Sequence Listing.

(56) References Cited

OTHER PUBLICATIONS

Tan, W. et al. 2018. "Diacylglycerol Acyltransferase and Diacylglycerol Kinase Modulate Triacylglycerol and Phosphatidic Acid Production in the Plant Response to Freezing Stress." Plant Physiology 177(3):1303-18. doi: 10.1104/pp.18.00402.
To, A., et al. 2013. "WRINKLED Transcription Factors Orchestrate Tissue-Specific Regulation of Fatty Acid Biosynthesis in *Arabidopsis*." The Plant Cell 24(12):5007-23. doi: 10.1105/tpc.112.106120.
Tominaga, R., et al. 2008. "*Arabidopsis* Caprice-Like MYB 3 ( CPL3 ) Controls Endoreduplication and Flowering Development in Addition to Trichome and Root Hair Formation." Development 135(7):1335-45. doi: 10.1242/dev.017947.
Welling, M. T., et al. 2019. "Complex Patterns of Cannabinoid Alkyl Side-Chain Inheritance in Cannabis." Scientific Reports 9(1):11421. doi: 10.1038/s41598-019-47812-2.
Welling, M. T., et al. 2020. "An Extreme-Phenotype Genome-wide Association Study Identifies Candidate Cannabinoid Pathway Genes in Cannabis." Scientific Reports 10(1):18643. doi: 10.1038/s41598-020-75271-7.
Yuan, L., et al. 1995. "Modification of the Substrate Specificity of an Acyl-Acyl Carrier Protein Thioesterase by Protein Engineering." Proceedings of the National Academy of Sciences 92(23):10639-43. doi: 10.1073/pnas.92.23.10639.
PCT International Search Report for PCT/US2021/044908; ISA/RU; dated Nov. 11, 2021.
PCT Written Opinion of the International Searching Authority for PCT/US2021/044908; ISA/RU; dated Nov. 11, 2021.
Wu and Wallace (1989) Genomics 4: 560.
Landegren et al. (1988) Science 241: 1077.
Barringer et al. (1990) Gene 89: 117.
Kwoh et al. (1989) Proc. Natl. Acad. Sci. USA 86: 1173.
Guatelli et al. (1990) Proc. Natl. Acad. Sci. USA 87: 1874.
Livingston et al. 2020, The Plant Journal 101: 37-56.
Potter et al. (2011), World Wide Weed: Global Trends in Cannabis Cultivation and Its Control.
Bakel et al., "The draft genome and transcriptome of *Cannabis sativa*" Genome Biology 12:R102.
Datwyler et al. (Genetic variation in hemp and marijuana (*Cannabis sativa* L.) according to amplified fragment length polymorphisms, J Forensic Sci. Mar. 2006; 51(2):371-5).
Pinarkara et al., (RAPD analysis of seized marijuana (*Cannabis sativa* L.) in Turkey, Electronic Journal of Biotechnology, 12(1), 2009).
Hakki et al., (Inter simple sequence repeats separate efficiently hemp from marijuana (*Cannabis sativa* L.), Electronic Journal of Biotechnology, 10(4), 2007).
Gilmore et al. (Isolation of microsatellite markers in *Cannabis sativa* L. (marijuana), Molecular Ecology Notes, 3(1):105-107, Mar. 2003).
Pacifico et al., (Genetics and marker-assisted selection of chemotype in *Cannabis sativa* L.), Molecular Breeding (2006) 17:257-268).
Mendoza et al., (Genetic individualization of *Cannabis sativa* by a short tandem repeat multiplex system, Anal Bioanal Chem (2009) 393:719-726).
Wan et al., Theor. Appl. Genet., 77:889-892, 1989.
Ching et al. (2002), BMC Genet. 3:19 pp.
Gupta et al. 2001, Rafalski (2002b), Plant Science 162:329-333).
Plink; Purcell et al. 2007, AJHG 81(3): 559-575.
Jones et al., EMBO J. 4:2411-2418 (1985).
De Almeida et al., Mol. Gen. Genetics 218:78-86 (1989).
Mullis et al., Methods Enzymol. 155:335-350 (1987).
Bakel et al., The draft genome and transcriptome of *Cannabis sativa*, Genome Biology, 12(10):R102, 2011).
Rudolf Brenneisen, 2007, Chemistry and Analysis of Phytocannabinoids (cannabinoids produced produced by Cannabis).
El-Alfy, Abir T, et al., 2010, "Antidepressant-like effect of delta-9-tetrahydrocannabinol and other cannabinoids isolated from *Cannabis sativa* L", Pharmacology Biochemistry and Behavior 95 (4): 434-42; incorporated herein by reference).
Innis and Gelfand, eds. (1995) PCR Strategies (Academic Press, New York).
Chen et al. (1994) PNAS 91:5695-5699.

\* cited by examiner

```
                        SEQUENCE LISTING

Sequence total quantity: 244
SEQ ID NO: 1           moltype = DNA   length = 51
FEATURE                Location/Qualifiers
source                 1..51
                       mol_type = genomic DNA
                       organism = Cannabis sativa
SEQUENCE: 1
aacaaatcaa tgaccaactc aacaacagca acaacggtat ttgagatgga g         51

SEQ ID NO: 2           moltype = DNA   length = 51
FEATURE                Location/Qualifiers
source                 1..51
                       mol_type = genomic DNA
                       organism = Cannabis sativa
SEQUENCE: 2
aagactaaaa cacagagaag aaagtaatag tcctaaagga gaagaagaaa a         51

SEQ ID NO: 3           moltype = DNA   length = 51
FEATURE                Location/Qualifiers
source                 1..51
                       mol_type = genomic DNA
                       organism = Cannabis sativa
SEQUENCE: 3
acaagtaggt gatgatataa ttgcattgct tcagcagggg agaaaatttg a         51

SEQ ID NO: 4           moltype = DNA   length = 51
FEATURE                Location/Qualifiers
source                 1..51
                       mol_type = genomic DNA
                       organism = Cannabis sativa
SEQUENCE: 4
ctgtggagct gcggttgtat ttggtgagta attctatgat tttgagtata a         51

SEQ ID NO: 5           moltype = DNA   length = 51
FEATURE                Location/Qualifiers
source                 1..51
                       mol_type = genomic DNA
                       organism = Cannabis sativa
SEQUENCE: 5
aagatttgaa ggagagattg gatagaaaaa caagaggtaa gccttagacc t         51

SEQ ID NO: 6           moltype = DNA   length = 51
FEATURE                Location/Qualifiers
source                 1..51
```

```
                            mol_type = genomic DNA
                            organism = Cannabis sativa
SEQUENCE: 6
ggatgacgat gccaccgttg atgaagactc tgtcgccgga gtccatggtg a            51

SEQ ID NO: 7               moltype = DNA   length = 51
FEATURE                    Location/Qualifiers
source                     1..51
                            mol_type = genomic DNA
                            organism = Cannabis sativa
SEQUENCE: 7
agagccttga ccatcaacaa caccattgcc ttgaatagtg aaattattga t            51

SEQ ID NO: 8               moltype = DNA   length = 51
FEATURE                    Location/Qualifiers
source                     1..51
                            mol_type = genomic DNA
                            organism = Cannabis sativa
SEQUENCE: 8
ggggaaaaca aaattggagg ccacgtggaa gccaaaatta aatttgtgga g            51

SEQ ID NO: 9               moltype = DNA   length = 51
FEATURE                    Location/Qualifiers
source                     1..51
                            mol_type = genomic DNA
                            organism = Cannabis sativa
SEQUENCE: 9
cacaccttaa atacaacaat cacacaaaga atcaaatttc accattggag c            51

SEQ ID NO: 10              moltype = DNA   length = 51
FEATURE                    Location/Qualifiers
source                     1..51
                            mol_type = genomic DNA
                            organism = Cannabis sativa
SEQUENCE: 10
aaaagatata tgtgtaatgt aatgtcacca gcttctcatc ttatatacgt a            51

SEQ ID NO: 11              moltype = DNA   length = 51
FEATURE                    Location/Qualifiers
source                     1..51
                            mol_type = genomic DNA
                            organism = Cannabis sativa
SEQUENCE: 11
acatgtgttt ggtttaaatt aaggggaaga taaccattag agaagaattg a            51

SEQ ID NO: 12              moltype = DNA   length = 51
FEATURE                    Location/Qualifiers
source                     1..51
                            mol_type = genomic DNA
                            organism = Cannabis sativa
SEQUENCE: 12
gctgctctac aaaattcagt accctgtcct gtccattaat ttggctttgg g            51

SEQ ID NO: 13              moltype = DNA   length = 51
FEATURE                    Location/Qualifiers
source                     1..51
                            mol_type = genomic DNA
                            organism = Cannabis sativa
SEQUENCE: 13
tagaggtaga gaatcataaa catgagacgg cattctctct tggtaaggac a            51

SEQ ID NO: 14              moltype = DNA   length = 51
FEATURE                    Location/Qualifiers
source                     1..51
                            mol_type = genomic DNA
                            organism = Cannabis sativa
SEQUENCE: 14
ttccaagcat cattggcatc atacagccaa taatagctgc cagacttaac t            51

SEQ ID NO: 15              moltype = DNA   length = 51
FEATURE                    Location/Qualifiers
source                     1..51
                            mol_type = genomic DNA
                            organism = Cannabis sativa
SEQUENCE: 15
ggcgccatgg gtgtgtggag ttcggcaact tccagaccag tggagcttcc a            51

SEQ ID NO: 16              moltype = DNA   length = 51
FEATURE                    Location/Qualifiers
```

```
source                  1..51
                        mol_type = genomic DNA
                        organism = Cannabis sativa
SEQUENCE: 16
caaaggaaaa caaagtcccc aacctggccc tcaatatctc tacacttcgt a        51

SEQ ID NO: 17           moltype = DNA   length = 51
FEATURE                 Location/Qualifiers
source                  1..51
                        mol_type = genomic DNA
                        organism = Cannabis sativa
SEQUENCE: 17
ttcaccaagc tgtgtgatag atctcatgtg atgaaactca caaataaat t          51

SEQ ID NO: 18           moltype = DNA   length = 51
FEATURE                 Location/Qualifiers
source                  1..51
                        mol_type = genomic DNA
                        organism = Cannabis sativa
SEQUENCE: 18
ggacttggtt aggatgtttt acggcgaatt gggtaagaag aaagatggaa g         51

SEQ ID NO: 19           moltype = DNA   length = 51
FEATURE                 Location/Qualifiers
source                  1..51
                        mol_type = genomic DNA
                        organism = Cannabis sativa
SEQUENCE: 19
aactactttt ctcaataaaa gaaactaaat actataatat tatagttgta t         51

SEQ ID NO: 20           moltype = DNA   length = 51
FEATURE                 Location/Qualifiers
source                  1..51
                        mol_type = genomic DNA
                        organism = Cannabis sativa
SEQUENCE: 20
atctaaattg tagtattttg ctaatggttg ctctatacat atgagaggtg a         51

SEQ ID NO: 21           moltype = DNA   length = 51
FEATURE                 Location/Qualifiers
source                  1..51
                        mol_type = genomic DNA
                        organism = Cannabis sativa
SEQUENCE: 21
accctaaaga agggacttac atgaaacttt tggttctcct tggaagatct g         51

SEQ ID NO: 22           moltype = DNA   length = 51
FEATURE                 Location/Qualifiers
source                  1..51
                        mol_type = genomic DNA
                        organism = Cannabis sativa
SEQUENCE: 22
ttgtagaagc acccaatatt attttggcct aatatggagat tgagttattc t        51

SEQ ID NO: 23           moltype = DNA   length = 51
FEATURE                 Location/Qualifiers
source                  1..51
                        mol_type = genomic DNA
                        organism = Cannabis sativa
SEQUENCE: 23
gttttacatt tggtagaaac caagacccca agaggtggtt tcttgaaagt a        51

SEQ ID NO: 24           moltype = DNA   length = 51
FEATURE                 Location/Qualifiers
source                  1..51
                        mol_type = genomic DNA
                        organism = Cannabis sativa
SEQUENCE: 24
gagctgtccc cgcttagtgg agcgcgaccc ccaaagttga catatgcaat g         51

SEQ ID NO: 25           moltype = DNA   length = 51
FEATURE                 Location/Qualifiers
source                  1..51
                        mol_type = genomic DNA
                        organism = Cannabis sativa
SEQUENCE: 25
aaatattctt actgctccaa cggttgggag gctaatgagt ttccctcgtc c         51

SEQ ID NO: 26           moltype = DNA   length = 51
```

| FEATURE | Location/Qualifiers |
|---|---|
| source | 1..51 |
| | mol_type = genomic DNA |
| | organism = Cannabis sativa |

SEQUENCE: 26 gtcgctcggg cattagctaa tccaaaggac atgactagga attcacagtg c　　　　　51

| SEQ ID NO: 27 | moltype = DNA   length = 51 |
|---|---|
| FEATURE | Location/Qualifiers |
| source | 1..51 |
| | mol_type = genomic DNA |
| | organism = Cannabis sativa |

SEQUENCE: 27 gcgaatttcc taaaagtttg gttcatcagg ttgtgtaatt ggctgaagct c　　　　　51

| SEQ ID NO: 28 | moltype = DNA   length = 51 |
|---|---|
| FEATURE | Location/Qualifiers |
| source | 1..51 |
| | mol_type = genomic DNA |
| | organism = Cannabis sativa |

SEQUENCE: 28 gagcttagtg aatccttgcc taaggccgat tttgattgag gagaattcct t　　　　　51

| SEQ ID NO: 29 | moltype = DNA   length = 51 |
|---|---|
| FEATURE | Location/Qualifiers |
| source | 1..51 |
| | mol_type = genomic DNA |
| | organism = Cannabis sativa |

SEQUENCE: 29 aaatttgaat aacatgttgg cttattggtg atggctctct tgttactagc a　　　　　51

| SEQ ID NO: 30 | moltype = DNA   length = 51 |
|---|---|
| FEATURE | Location/Qualifiers |
| source | 1..51 |
| | mol_type = genomic DNA |
| | organism = Cannabis sativa |

SEQUENCE: 30 ttaacctcat attcgtacac ttgagagaga ctggccgtgc atcaacttcg g　　　　　51

| SEQ ID NO: 31 | moltype = DNA   length = 51 |
|---|---|
| FEATURE | Location/Qualifiers |
| source | 1..51 |
| | mol_type = genomic DNA |
| | organism = Cannabis sativa |

SEQUENCE: 31 taaagacaaa cactgggaac gtgtagtaat tgagactgat agcatgatat c　　　　　51

| SEQ ID NO: 32 | moltype = DNA   length = 51 |
|---|---|
| FEATURE | Location/Qualifiers |
| source | 1..51 |
| | mol_type = genomic DNA |
| | organism = Cannabis sativa |

SEQUENCE: 32 attaatatag taatggttta cactaggtgc acaaccattc catcattctg a　　　　　51

| SEQ ID NO: 33 | moltype = DNA   length = 51 |
|---|---|
| FEATURE | Location/Qualifiers |
| source | 1..51 |
| | mol_type = genomic DNA |
| | organism = Cannabis sativa |

SEQUENCE: 33 aatccaagct agctaatgtt ttgcatgcca atgagctttc aagacgttta a　　　　　51

| SEQ ID NO: 34 | moltype = DNA   length = 51 |
|---|---|
| FEATURE | Location/Qualifiers |
| source | 1..51 |
| | mol_type = genomic DNA |
| | organism = Cannabis sativa |

SEQUENCE: 34 cccttttatt gggcctgatt atggattgag ctttttatat attttaatga a　　　　　51

| SEQ ID NO: 35 | moltype = DNA   length = 51 |
|---|---|
| FEATURE | Location/Qualifiers |
| source | 1..51 |
| | mol_type = genomic DNA |
| | organism = Cannabis sativa |

SEQUENCE: 35 actaatgatt cttctaggtc aatgaatcaa aattttatgc ccaaagattg t　　　　　51

| | | |
|---|---|---|
| SEQ ID NO: 36 | moltype = DNA length = 51 | |
| FEATURE | Location/Qualifiers | |
| source | 1..51<br>mol_type = genomic DNA<br>organism = Cannabis sativa | |
| SEQUENCE: 36 | | |
| actccaaaat tgcagaacta ggcagaggag atggagcaga tggatttcca a | | 51 |
| | | |
| SEQ ID NO: 37 | moltype = DNA length = 51 | |
| FEATURE | Location/Qualifiers | |
| source | 1..51<br>mol_type = genomic DNA<br>organism = Cannabis sativa | |
| SEQUENCE: 37 | | |
| ttttggagag gtgattaaac ttttcgagga gctgactgct gcaaacccct c | | 51 |
| | | |
| SEQ ID NO: 38 | moltype = DNA length = 51 | |
| FEATURE | Location/Qualifiers | |
| source | 1..51<br>mol_type = genomic DNA<br>organism = Cannabis sativa | |
| SEQUENCE: 38 | | |
| aagtttttaaa aaatttggtg tgcccgtgtg gggtctgtgg aagttatgga a | | 51 |
| | | |
| SEQ ID NO: 39 | moltype = DNA length = 51 | |
| FEATURE | Location/Qualifiers | |
| source | 1..51<br>mol_type = genomic DNA<br>organism = Cannabis sativa | |
| SEQUENCE: 39 | | |
| ttgctcacat ccttgtccat ggttcctgtc agccacttga agtctggctg a | | 51 |
| | | |
| SEQ ID NO: 40 | moltype = DNA length = 51 | |
| FEATURE | Location/Qualifiers | |
| source | 1..51<br>mol_type = genomic DNA<br>organism = Cannabis sativa | |
| SEQUENCE: 40 | | |
| ggtaagttaa ttgtatttcc catcagttct ttttttgcta tgtaacatgt t | | 51 |
| | | |
| SEQ ID NO: 41 | moltype = DNA length = 51 | |
| FEATURE | Location/Qualifiers | |
| source | 1..51<br>mol_type = genomic DNA<br>organism = Cannabis sativa | |
| SEQUENCE: 41 | | |
| tacttatttg gaaagtagca ccattgccga caaggcaaac ttggtgcgag t | | 51 |
| | | |
| SEQ ID NO: 42 | moltype = DNA length = 51 | |
| FEATURE | Location/Qualifiers | |
| source | 1..51<br>mol_type = genomic DNA<br>organism = Cannabis sativa | |
| SEQUENCE: 42 | | |
| tatcagatta cccctctatg ttggagaaga tccaactctg atggcacagt t | | 51 |
| | | |
| SEQ ID NO: 43 | moltype = DNA length = 51 | |
| FEATURE | Location/Qualifiers | |
| source | 1..51<br>mol_type = genomic DNA<br>organism = Cannabis sativa | |
| SEQUENCE: 43 | | |
| tgaaggccta tgccctcgac cgtccgaaga aggtgcagaa gataaatgca t | | 51 |
| | | |
| SEQ ID NO: 44 | moltype = DNA length = 51 | |
| FEATURE | Location/Qualifiers | |
| source | 1..51<br>mol_type = genomic DNA<br>organism = Cannabis sativa | |
| SEQUENCE: 44 | | |
| caagtgacag atcaaatgca tgtgactcac ctgacacctt ggctggcata g | | 51 |
| | | |
| SEQ ID NO: 45 | moltype = DNA length = 51 | |
| FEATURE | Location/Qualifiers | |
| source | 1..51<br>mol_type = genomic DNA<br>organism = Cannabis sativa | |
| SEQUENCE: 45 | | |
| acatacttgg tagtaaatct agatcctggt aaaatatttc caacagctaa a | | 51 |

```
SEQ ID NO: 46          moltype = DNA  length = 51
FEATURE                Location/Qualifiers
source                 1..51
                       mol_type = genomic DNA
                       organism = Cannabis sativa
SEQUENCE: 46
atttgatttc tatttattgt tatttgtagt atccaacatg actatgacca a          51

SEQ ID NO: 47          moltype = DNA  length = 51
FEATURE                Location/Qualifiers
source                 1..51
                       mol_type = genomic DNA
                       organism = Cannabis sativa
SEQUENCE: 47
aacaaatgaa gtctcctcta atctatatta atagctagct agttggtttt c          51

SEQ ID NO: 48          moltype = DNA  length = 51
FEATURE                Location/Qualifiers
source                 1..51
                       mol_type = genomic DNA
                       organism = Cannabis sativa
SEQUENCE: 48
gtttgtgcac ttttccattt aaaaagttgc tttgtttcag tttgtaagct t          51

SEQ ID NO: 49          moltype = DNA  length = 51
FEATURE                Location/Qualifiers
source                 1..51
                       mol_type = genomic DNA
                       organism = Cannabis sativa
SEQUENCE: 49
ataccagagc ttcttcttga aattggaagg tgccacaggc cacccggtca t          51

SEQ ID NO: 50          moltype = DNA  length = 51
FEATURE                Location/Qualifiers
source                 1..51
                       mol_type = genomic DNA
                       organism = Cannabis sativa
SEQUENCE: 50
tgttttctag tttaaatttc gattgtcgtt gccttctcct agcttgccta g          51

SEQ ID NO: 51          moltype = DNA  length = 51
FEATURE                Location/Qualifiers
source                 1..51
                       mol_type = genomic DNA
                       organism = Cannabis sativa
SEQUENCE: 51
gttgactaga gctcagtcta tgaattatca tatttataaa tatacataaa t          51

SEQ ID NO: 52          moltype = DNA  length = 51
FEATURE                Location/Qualifiers
source                 1..51
                       mol_type = genomic DNA
                       organism = Cannabis sativa
SEQUENCE: 52
ctggcctatt aagctgatgg acatcaagac cacaagatgc caattcggaa g          51

SEQ ID NO: 53          moltype = DNA  length = 51
FEATURE                Location/Qualifiers
source                 1..51
                       mol_type = genomic DNA
                       organism = Cannabis sativa
SEQUENCE: 53
cttgaccaag aatccacttt gccattctcc tatgtctttt atccactctt g          51

SEQ ID NO: 54          moltype = DNA  length = 51
FEATURE                Location/Qualifiers
source                 1..51
                       mol_type = genomic DNA
                       organism = Cannabis sativa
SEQUENCE: 54
ctagaagtgc actgaccaaa cccccaacac ttatctcaag tagccattgt t          51

SEQ ID NO: 55          moltype = DNA  length = 51
FEATURE                Location/Qualifiers
source                 1..51
                       mol_type = genomic DNA
                       organism = Cannabis sativa
SEQUENCE: 55
```

-continued

```
aacacatgaa tgtacgattc tatttgggtt gtggtagatc aatttacgaa t          51

SEQ ID NO: 56           moltype = DNA   length = 51
FEATURE                 Location/Qualifiers
source                  1..51
                        mol_type = genomic DNA
                        organism = Cannabis sativa
SEQUENCE: 56
ttgtgtctcg catgtatcat tggctcaggt ttgcaaaatg caaccctatg c          51

SEQ ID NO: 57           moltype = DNA   length = 51
FEATURE                 Location/Qualifiers
source                  1..51
                        mol_type = genomic DNA
                        organism = Cannabis sativa
SEQUENCE: 57
aaaggagagt gaaacagtga atgtgaaaaa ccttttctc tcagtttccg c            51

SEQ ID NO: 58           moltype = DNA   length = 51
FEATURE                 Location/Qualifiers
source                  1..51
                        mol_type = genomic DNA
                        organism = Cannabis sativa
SEQUENCE: 58
ggtgtcgatg taatttccat aatcaccaca atcaaaccaa agccttcctt t          51

SEQ ID NO: 59           moltype = DNA   length = 51
FEATURE                 Location/Qualifiers
source                  1..51
                        mol_type = genomic DNA
                        organism = Cannabis sativa
SEQUENCE: 59
agatgcagta gtcaccaaaa ttacaaagaa aacaatttgg ttatgtatat t          51

SEQ ID NO: 60           moltype = DNA   length = 51
FEATURE                 Location/Qualifiers
source                  1..51
                        mol_type = genomic DNA
                        organism = Cannabis sativa
SEQUENCE: 60
ttaatttcat taattattag aaaataaata aaataagttg actataatat t          51

SEQ ID NO: 61           moltype = DNA   length = 51
FEATURE                 Location/Qualifiers
source                  1..51
                        mol_type = genomic DNA
                        organism = Cannabis sativa
SEQUENCE: 61
gggtataaca atttcccctt aaaatgtctt tattaataaa aagtgctttt a          51

SEQ ID NO: 62           moltype = DNA   length = 51
FEATURE                 Location/Qualifiers
source                  1..51
                        mol_type = genomic DNA
                        organism = Cannabis sativa
SEQUENCE: 62
tccagttatg taacttgcag caggaccaag tgccaaaaat tccactagcc c          51

SEQ ID NO: 63           moltype = DNA   length = 51
FEATURE                 Location/Qualifiers
source                  1..51
                        mol_type = genomic DNA
                        organism = Cannabis sativa
SEQUENCE: 63
caggaatacc ttgccatttg atatgctctt gaggcttaca ggaagtcttg a          51

SEQ ID NO: 64           moltype = DNA   length = 51
FEATURE                 Location/Qualifiers
source                  1..51
                        mol_type = genomic DNA
                        organism = Cannabis sativa
SEQUENCE: 64
ataaattatg aggttgactt tggattgggt caacctattt atgttggacc t          51

SEQ ID NO: 65           moltype = DNA   length = 51
FEATURE                 Location/Qualifiers
source                  1..51
                        mol_type = genomic DNA
                        organism = Cannabis sativa
```

-continued

```
SEQUENCE: 65
aagaaggcca tttataattc actactggga caacaaaagc aacacctgat a          51

SEQ ID NO: 66           moltype = DNA   length = 51
FEATURE                 Location/Qualifiers
source                  1..51
                        mol_type = genomic DNA
                        organism = Cannabis sativa
SEQUENCE: 66
atgctactag gaatatttga ttcaaccca aactaatata agatagtagt a            51

SEQ ID NO: 67           moltype = DNA   length = 51
FEATURE                 Location/Qualifiers
source                  1..51
                        mol_type = genomic DNA
                        organism = Cannabis sativa
SEQUENCE: 67
cagcttgttc ctcaacaaac ttcacaagct tctccagata ccgatctccg g          51

SEQ ID NO: 68           moltype = DNA   length = 51
FEATURE                 Location/Qualifiers
source                  1..51
                        mol_type = genomic DNA
                        organism = Cannabis sativa
SEQUENCE: 68
tgtgtacatt caggtttata tatgtgcatg cctctcatac tgctaaactt c          51

SEQ ID NO: 69           moltype = DNA   length = 51
FEATURE                 Location/Qualifiers
source                  1..51
                        mol_type = genomic DNA
                        organism = Cannabis sativa
SEQUENCE: 69
tgtggtggat aaagacaggc ccccatctca tcaatctgtt cgccgatttt t          51

SEQ ID NO: 70           moltype = DNA   length = 51
FEATURE                 Location/Qualifiers
source                  1..51
                        mol_type = genomic DNA
                        organism = Cannabis sativa
SEQUENCE: 70
ggaacacttt attggctaaa aaaggtccct acttgagaaa atactttacc t          51

SEQ ID NO: 71           moltype = DNA   length = 51
FEATURE                 Location/Qualifiers
source                  1..51
                        mol_type = genomic DNA
                        organism = Cannabis sativa
SEQUENCE: 71
tgacccataa gatttcaagt cagccgtgtc gataataaat tatattaagg a          51

SEQ ID NO: 72           moltype = DNA   length = 51
FEATURE                 Location/Qualifiers
source                  1..51
                        mol_type = genomic DNA
                        organism = Cannabis sativa
SEQUENCE: 72
actcaattat ttatagtatc ctatttccaa tttccactta gaacactccc a          51

SEQ ID NO: 73           moltype = DNA   length = 51
FEATURE                 Location/Qualifiers
source                  1..51
                        mol_type = genomic DNA
                        organism = Cannabis sativa
SEQUENCE: 73
ttcacaattg gattctactc atcgtcgttg tggtgctttt cggtgctgtt g          51

SEQ ID NO: 74           moltype = DNA   length = 51
FEATURE                 Location/Qualifiers
source                  1..51
                        mol_type = genomic DNA
                        organism = Cannabis sativa
SEQUENCE: 74
taaacgactt ttaagactta atcttccatt tgattggaca atacaaacaa a          51

SEQ ID NO: 75           moltype = DNA   length = 51
FEATURE                 Location/Qualifiers
source                  1..51
                        mol_type = genomic DNA
```

```
                        organism = Cannabis sativa
SEQUENCE: 75
aatttgataa aaccatccac ctattctttt aacataatta attatatctt t            51

SEQ ID NO: 76           moltype = DNA   length = 51
FEATURE                 Location/Qualifiers
source                  1..51
                        mol_type = genomic DNA
                        organism = Cannabis sativa
SEQUENCE: 76
atttatctgg cgcccctaag agagtctctg gtaatttaga atctatggga t            51

SEQ ID NO: 77           moltype = DNA   length = 51
FEATURE                 Location/Qualifiers
source                  1..51
                        mol_type = genomic DNA
                        organism = Cannabis sativa
SEQUENCE: 77
ttctacagaa tacataattg gactgctttt tttgttatac aaacttggat c            51

SEQ ID NO: 78           moltype = DNA   length = 51
FEATURE                 Location/Qualifiers
source                  1..51
                        mol_type = genomic DNA
                        organism = Cannabis sativa
SEQUENCE: 78
tttgcttata atcggagtta ttgttctgtt tcagggcctg aaaatatggg g            51

SEQ ID NO: 79           moltype = DNA   length = 51
FEATURE                 Location/Qualifiers
source                  1..51
                        mol_type = genomic DNA
                        organism = Cannabis sativa
SEQUENCE: 79
cacgacatga aaaatgtgtt cttaagcacg acacgttacg agaagtacaa a            51

SEQ ID NO: 80           moltype = DNA   length = 51
FEATURE                 Location/Qualifiers
source                  1..51
                        mol_type = genomic DNA
                        organism = Cannabis sativa
SEQUENCE: 80
tacttcttct gtcttatgtg aaactttctt taactgcatt tcatttgac a             51

SEQ ID NO: 81           moltype = DNA   length = 51
FEATURE                 Location/Qualifiers
source                  1..51
                        mol_type = genomic DNA
                        organism = Cannabis sativa
SEQUENCE: 81
ttgcaaataa gatgatatat taagtcttga acttggaaat aacaagttag a            51

SEQ ID NO: 82           moltype = DNA   length = 51
FEATURE                 Location/Qualifiers
source                  1..51
                        mol_type = genomic DNA
                        organism = Cannabis sativa
SEQUENCE: 82
gatgattgct gatcctatga caaaaggctt gctacctcat aaattcaagg a            51

SEQ ID NO: 83           moltype = DNA   length = 51
FEATURE                 Location/Qualifiers
source                  1..51
                        mol_type = genomic DNA
                        organism = Cannabis sativa
SEQUENCE: 83
aaaaaagacg aattttagca cgacacacgg tataatgcta caaattagca c            51

SEQ ID NO: 84           moltype = DNA   length = 51
FEATURE                 Location/Qualifiers
source                  1..51
                        mol_type = genomic DNA
                        organism = Cannabis sativa
SEQUENCE: 84
catctaaaaa ctcttgtact actttgatat cttcaggtag aattgactca g            51

SEQ ID NO: 85           moltype = DNA   length = 51
FEATURE                 Location/Qualifiers
source                  1..51
```

```
                        mol_type = genomic DNA
                        organism = Cannabis sativa
SEQUENCE: 85
agaaagtcat ggttctcatt tagtaaacat gatgtcacaa taatccagag a          51

SEQ ID NO: 86           moltype = DNA  length = 51
FEATURE                 Location/Qualifiers
source                  1..51
                        mol_type = genomic DNA
                        organism = Cannabis sativa
SEQUENCE: 86
agatgtttca tgaagcattt ggttgcgtca tctacctatc agctagagaa g          51

SEQ ID NO: 87           moltype = DNA  length = 51
FEATURE                 Location/Qualifiers
source                  1..51
                        mol_type = genomic DNA
                        organism = Cannabis sativa
SEQUENCE: 87
cacatgatat tgatgtttca atttgataat catgttttat atactgcact g          51

SEQ ID NO: 88           moltype = DNA  length = 51
FEATURE                 Location/Qualifiers
source                  1..51
                        mol_type = genomic DNA
                        organism = Cannabis sativa
SEQUENCE: 88
agtgcaacac taaagaaagc ccaatagaga ggttcaaagc agttcttgca t          51

SEQ ID NO: 89           moltype = DNA  length = 51
FEATURE                 Location/Qualifiers
source                  1..51
                        mol_type = genomic DNA
                        organism = Cannabis sativa
SEQUENCE: 89
taagagaaac cattctatgt aattaacccc tataaaatgg tggttgcatc t          51

SEQ ID NO: 90           moltype = DNA  length = 51
FEATURE                 Location/Qualifiers
source                  1..51
                        mol_type = genomic DNA
                        organism = Cannabis sativa
SEQUENCE: 90
ggcctgccag cccctagaa gtggcatgtt catcatttca ttgtccctcc t           51

SEQ ID NO: 91           moltype = DNA  length = 51
FEATURE                 Location/Qualifiers
source                  1..51
                        mol_type = genomic DNA
                        organism = Cannabis sativa
SEQUENCE: 91
aaagcacccc tggccaagga cttttttttct atgcaacctg ctttgaccct c         51

SEQ ID NO: 92           moltype = DNA  length = 51
FEATURE                 Location/Qualifiers
source                  1..51
                        mol_type = genomic DNA
                        organism = Cannabis sativa
SEQUENCE: 92
ccaaatcaag catgcaaaac atcattttct tcccaaaatt tccaagaaac t          51

SEQ ID NO: 93           moltype = DNA  length = 51
FEATURE                 Location/Qualifiers
source                  1..51
                        mol_type = genomic DNA
                        organism = Cannabis sativa
SEQUENCE: 93
agtgttgcat gaaatatgtt atttgagcat ctattaatgg ttagtaatcc t          51

SEQ ID NO: 94           moltype = DNA  length = 51
FEATURE                 Location/Qualifiers
source                  1..51
                        mol_type = genomic DNA
                        organism = Cannabis sativa
SEQUENCE: 94
catagttgct caaccttaac tttgcattta cctacacatg caaacaataa c          51

SEQ ID NO: 95           moltype = DNA  length = 51
FEATURE                 Location/Qualifiers
```

```
source                  1..51
                        mol_type = genomic DNA
                        organism = Cannabis sativa
SEQUENCE: 95
ctcaataaaa attcaatctt tcttctacag ctcactcttc ccataaccag a            51

SEQ ID NO: 96           moltype = DNA   length = 51
FEATURE                 Location/Qualifiers
source                  1..51
                        mol_type = genomic DNA
                        organism = Cannabis sativa
SEQUENCE: 96
tagttaggct aattatagtt tttggtttcg aactttaata tgtattagat c            51

SEQ ID NO: 97           moltype = DNA   length = 51
FEATURE                 Location/Qualifiers
source                  1..51
                        mol_type = genomic DNA
                        organism = Cannabis sativa
SEQUENCE: 97
taataatatg agttaacaca ataaagaact atctaatcaa tctcaagttt t            51

SEQ ID NO: 98           moltype = DNA   length = 51
FEATURE                 Location/Qualifiers
source                  1..51
                        mol_type = genomic DNA
                        organism = Cannabis sativa
SEQUENCE: 98
ccagttcagt cataaaggca cttataaggg cagaatttga gactttaatc t            51

SEQ ID NO: 99           moltype = DNA   length = 51
FEATURE                 Location/Qualifiers
source                  1..51
                        mol_type = genomic DNA
                        organism = Cannabis sativa
SEQUENCE: 99
ggttgttatg acttgtatat gttgtatatt atgtgttgta tgctaacgtg t            51

SEQ ID NO: 100          moltype = DNA   length = 51
FEATURE                 Location/Qualifiers
source                  1..51
                        mol_type = genomic DNA
                        organism = Cannabis sativa
SEQUENCE: 100
gtgtttgaaa gagtactcat accacgtata atttttgtg tcaagtttta a             51

SEQ ID NO: 101          moltype = DNA   length = 51
FEATURE                 Location/Qualifiers
source                  1..51
                        mol_type = genomic DNA
                        organism = Cannabis sativa
SEQUENCE: 101
ttgacaagtg caactgagat tcatactctc tatgaaactc ggcttgctcg a            51

SEQ ID NO: 102          moltype = DNA   length = 51
FEATURE                 Location/Qualifiers
source                  1..51
                        mol_type = genomic DNA
                        organism = Cannabis sativa
SEQUENCE: 102
aactagacaa aacttgcaat gtaatatcag tcctccacat tagtaataaa c            51

SEQ ID NO: 103          moltype = DNA   length = 51
FEATURE                 Location/Qualifiers
source                  1..51
                        mol_type = genomic DNA
                        organism = Cannabis sativa
SEQUENCE: 103
tagtgggtaa ttatatatgt tatgagattt atcgtcttac catgtaaagg a            51

SEQ ID NO: 104          moltype = DNA   length = 51
FEATURE                 Location/Qualifiers
source                  1..51
                        mol_type = genomic DNA
                        organism = Cannabis sativa
SEQUENCE: 104
gccctataat ataaaatgat gacctgaaat ggatatgaaa gaagaatggc a            51

SEQ ID NO: 105          moltype = DNA   length = 51
```

```
FEATURE              Location/Qualifiers
source               1..51
                     mol_type = genomic DNA
                     organism = Cannabis sativa
SEQUENCE: 105
tgttgtcaat attaaccatg atcccgaccc aggtttcttg aggtatgact c          51

SEQ ID NO: 106       moltype = DNA   length = 51
FEATURE              Location/Qualifiers
source               1..51
                     mol_type = genomic DNA
                     organism = Cannabis sativa
SEQUENCE: 106
ggtcactcac tgtgaacgcc acgttaaaaa ttgaagttaa tgcatctagc t          51

SEQ ID NO: 107       moltype = DNA   length = 51
FEATURE              Location/Qualifiers
source               1..51
                     mol_type = genomic DNA
                     organism = Cannabis sativa
SEQUENCE: 107
gcgcaccact aaataacttt agaagtccaa atcgtatttt cccaacacag a          51

SEQ ID NO: 108       moltype = DNA   length = 51
FEATURE              Location/Qualifiers
source               1..51
                     mol_type = genomic DNA
                     organism = Cannabis sativa
SEQUENCE: 108
ttcaagttgt atctcttgtg catactgagt tgttggcatt cgatctcgca a          51

SEQ ID NO: 109       moltype = DNA   length = 51
FEATURE              Location/Qualifiers
source               1..51
                     mol_type = genomic DNA
                     organism = Cannabis sativa
SEQUENCE: 109
agtatggcaa aataagccaa ccaatgcctc gtatctttat gcatttgcgg t          51

SEQ ID NO: 110       moltype = DNA   length = 51
FEATURE              Location/Qualifiers
source               1..51
                     mol_type = genomic DNA
                     organism = Cannabis sativa
SEQUENCE: 110
ttgagaaaat atcaacttag acactgggtc cccttctag ccctttggaa a           51

SEQ ID NO: 111       moltype = DNA   length = 51
FEATURE              Location/Qualifiers
source               1..51
                     mol_type = genomic DNA
                     organism = Cannabis sativa
SEQUENCE: 111
gaaaaatac atttgccatt gctcaacaca agcatcatca cagtatctat g           51

SEQ ID NO: 112       moltype = DNA   length = 51
FEATURE              Location/Qualifiers
source               1..51
                     mol_type = genomic DNA
                     organism = Cannabis sativa
SEQUENCE: 112
ggtgcaatat tagctgggtt aacaattata tggtttcttt tcgaagtagc t          51

SEQ ID NO: 113       moltype = DNA   length = 51
FEATURE              Location/Qualifiers
source               1..51
                     mol_type = genomic DNA
                     organism = Cannabis sativa
SEQUENCE: 113
tctgtttggt tcctgagaaa atttgtcagg gtttgatttt ttaggtatta a          51

SEQ ID NO: 114       moltype = DNA   length = 51
FEATURE              Location/Qualifiers
source               1..51
                     mol_type = genomic DNA
                     organism = Cannabis sativa
SEQUENCE: 114
gattgataaa gagacaaatt aaacaaaaat attaaagact attaaatagt a          51
```

```
SEQ ID NO: 115              moltype = DNA   length = 51
FEATURE                     Location/Qualifiers
source                      1..51
                            mol_type = genomic DNA
                            organism = Cannabis sativa
SEQUENCE: 115
gcactaagtt ttgaagtgtt atttgaagca tggtagaaag attatctttt t            51

SEQ ID NO: 116              moltype = DNA   length = 51
FEATURE                     Location/Qualifiers
source                      1..51
                            mol_type = genomic DNA
                            organism = Cannabis sativa
SEQUENCE: 116
aataaatctg aaaaagtgga aaaaatctga gttagtagag tagatttctg g            51

SEQ ID NO: 117              moltype = DNA   length = 51
FEATURE                     Location/Qualifiers
source                      1..51
                            mol_type = genomic DNA
                            organism = Cannabis sativa
SEQUENCE: 117
tctcattaca atcgatgaaa gcaattgatt ctcttaggat ggagttctat t            51

SEQ ID NO: 118              moltype = DNA   length = 51
FEATURE                     Location/Qualifiers
source                      1..51
                            mol_type = genomic DNA
                            organism = Cannabis sativa
SEQUENCE: 118
gggcttaagt agaggcctag ctcgttttat ctcaaacacg atctcatgac a            51

SEQ ID NO: 119              moltype = DNA   length = 51
FEATURE                     Location/Qualifiers
source                      1..51
                            mol_type = genomic DNA
                            organism = Cannabis sativa
SEQUENCE: 119
tccggatctt ggtgttggta atgcagttta ggcattttgg catttttat t             51

SEQ ID NO: 120              moltype = DNA   length = 51
FEATURE                     Location/Qualifiers
source                      1..51
                            mol_type = genomic DNA
                            organism = Cannabis sativa
SEQUENCE: 120
gcaatggacg gaagtgccta agaaaatttg agtaaagaaa gatattttat g            51

SEQ ID NO: 121              moltype = DNA   length = 51
FEATURE                     Location/Qualifiers
source                      1..51
                            mol_type = genomic DNA
                            organism = Cannabis sativa
SEQUENCE: 121
ccattagaaa aaaagggaaa aacaccctaa accctaaagc aggcatgaaa a            51

SEQ ID NO: 122              moltype = DNA   length = 51
FEATURE                     Location/Qualifiers
source                      1..51
                            mol_type = genomic DNA
                            organism = Cannabis sativa
SEQUENCE: 122
aaagtagaat tgggagtttt gactcaaaat gtaaatttgt gagttgacag t            51

SEQ ID NO: 123              moltype = DNA   length = 51
FEATURE                     Location/Qualifiers
source                      1..51
                            mol_type = genomic DNA
                            organism = Cannabis sativa
SEQUENCE: 123
cacgacatga aaaatgtgtt cttaagcacg acacgttacg agaagtacaa a            51

SEQ ID NO: 124              moltype = DNA   length = 51
FEATURE                     Location/Qualifiers
source                      1..51
                            mol_type = genomic DNA
                            organism = Cannabis sativa
SEQUENCE: 124
taaaatttta ttctgaatgc caaaacagat acatgtgtat cgatataccc a            51
```

```
SEQ ID NO: 125          moltype = DNA   length = 51
FEATURE                 Location/Qualifiers
source                  1..51
                        mol_type = genomic DNA
                        organism = Cannabis sativa
SEQUENCE: 125
caccctagaa agcctccacg attctcttgc agtcgtagaa gaaggcgcaa t           51

SEQ ID NO: 126          moltype = DNA   length = 51
FEATURE                 Location/Qualifiers
source                  1..51
                        mol_type = genomic DNA
                        organism = Cannabis sativa
SEQUENCE: 126
atagatagaa aggggtgaat gagaaactca aatgaaaaat aataatatt t            51

SEQ ID NO: 127          moltype = DNA   length = 51
FEATURE                 Location/Qualifiers
source                  1..51
                        mol_type = genomic DNA
                        organism = Cannabis sativa
SEQUENCE: 127
aactatatat aaaacacaaa tataaggaat tatatttagt ttcaaatttt t           51

SEQ ID NO: 128          moltype = DNA   length = 51
FEATURE                 Location/Qualifiers
source                  1..51
                        mol_type = genomic DNA
                        organism = Cannabis sativa
SEQUENCE: 128
agatttata aatgctccaa atgggttgtc taaggtgtct gcagcagtaa a            51

SEQ ID NO: 129          moltype = DNA   length = 51
FEATURE                 Location/Qualifiers
source                  1..51
                        mol_type = genomic DNA
                        organism = Cannabis sativa
SEQUENCE: 129
gcatcttttt tcccttatgg atacacaagc aattcaacga aggaaaagat a           51

SEQ ID NO: 130          moltype = DNA   length = 51
FEATURE                 Location/Qualifiers
source                  1..51
                        mol_type = genomic DNA
                        organism = Cannabis sativa
SEQUENCE: 130
acttgggccc ttcattgttt ctatataaaa ttgctcgacc tattttgcat t           51

SEQ ID NO: 131          moltype = DNA   length = 51
FEATURE                 Location/Qualifiers
source                  1..51
                        mol_type = genomic DNA
                        organism = Cannabis sativa
SEQUENCE: 131
catgtagagg cacctacggc aggatccgtc atcttggcag gaattccatc a           51

SEQ ID NO: 132          moltype = DNA   length = 51
FEATURE                 Location/Qualifiers
source                  1..51
                        mol_type = genomic DNA
                        organism = Cannabis sativa
SEQUENCE: 132
caactgccca aatggaaggg actgaagttc gagagtattc atcaacctaa a           51

SEQ ID NO: 133          moltype = DNA   length = 51
FEATURE                 Location/Qualifiers
source                  1..51
                        mol_type = genomic DNA
                        organism = Cannabis sativa
SEQUENCE: 133
aagaaagggg gaaagaaagt catacgtgac cactaacact cccctagtgt g           51

SEQ ID NO: 134          moltype = DNA   length = 51
FEATURE                 Location/Qualifiers
source                  1..51
                        mol_type = genomic DNA
                        organism = Cannabis sativa
SEQUENCE: 134
```

```
aggcaagaca acccctccaac atagcgagta tccaaaagac cttagtcaga g                51

SEQ ID NO: 135          moltype = DNA   length = 51
FEATURE                 Location/Qualifiers
source                  1..51
                        mol_type = genomic DNA
                        organism = Cannabis sativa
SEQUENCE: 135
acaaaacata ttaaaaagaa gtgaggtgaa gagatgacct aagaagtgaa a                 51

SEQ ID NO: 136          moltype = DNA   length = 51
FEATURE                 Location/Qualifiers
source                  1..51
                        mol_type = genomic DNA
                        organism = Cannabis sativa
SEQUENCE: 136
accaagaaat tagtgataag aaaacagctt cggaatttat tttccagtaa c                 51

SEQ ID NO: 137          moltype = DNA   length = 51
FEATURE                 Location/Qualifiers
source                  1..51
                        mol_type = genomic DNA
                        organism = Cannabis sativa
SEQUENCE: 137
tcttctccaa actaaaagca aaatactgag gaaactcctt aacctcttcc a                 51

SEQ ID NO: 138          moltype = DNA   length = 51
FEATURE                 Location/Qualifiers
source                  1..51
                        mol_type = genomic DNA
                        organism = Cannabis sativa
SEQUENCE: 138
tactgccaac atttgttgga acagccggag atgacgcccc agcagagctg a                 51

SEQ ID NO: 139          moltype = DNA   length = 51
FEATURE                 Location/Qualifiers
source                  1..51
                        mol_type = genomic DNA
                        organism = Cannabis sativa
SEQUENCE: 139
ccccgaagct gtatatgttg taattattca ttagtttcac taccacaaca t                 51

SEQ ID NO: 140          moltype = DNA   length = 51
FEATURE                 Location/Qualifiers
source                  1..51
                        mol_type = genomic DNA
                        organism = Cannabis sativa
SEQUENCE: 140
cattttagtt caactgcagc attagctaat gctctgaact cactttctgt a                 51

SEQ ID NO: 141          moltype = DNA   length = 51
FEATURE                 Location/Qualifiers
source                  1..51
                        mol_type = genomic DNA
                        organism = Cannabis sativa
SEQUENCE: 141
atgaaattta ttattttgtc ttttgttgta aaagtatcac aaataatgaa c                 51

SEQ ID NO: 142          moltype = DNA   length = 51
FEATURE                 Location/Qualifiers
source                  1..51
                        mol_type = genomic DNA
                        organism = Cannabis sativa
SEQUENCE: 142
cttatcaaaa ttttggtaaa caactacatt aatttagagt cttatgaaaa t                 51

SEQ ID NO: 143          moltype = DNA   length = 51
FEATURE                 Location/Qualifiers
source                  1..51
                        mol_type = genomic DNA
                        organism = Cannabis sativa
SEQUENCE: 143
tttggcaatt aatgatattt agttaaagca cctaatccat gacagaattg a                 51

SEQ ID NO: 144          moltype = DNA   length = 51
FEATURE                 Location/Qualifiers
source                  1..51
                        mol_type = genomic DNA
                        organism = Cannabis sativa
```

-continued

```
SEQUENCE: 144
atatttctttt ccttctaagg atagagtaag cttttgacta cgtgggccaa t                    51

SEQ ID NO: 145         moltype = DNA   length = 51
FEATURE                Location/Qualifiers
source                 1..51
                       mol_type = genomic DNA
                       organism = Cannabis sativa
SEQUENCE: 145
ccacgtgtat tagagatcaa aagatgatga acttttgtgg gaattgtgtt c                     51

SEQ ID NO: 146         moltype = DNA   length = 51
FEATURE                Location/Qualifiers
source                 1..51
                       mol_type = genomic DNA
                       organism = Cannabis sativa
SEQUENCE: 146
tcgtgctaaa tgggttagta gtctaattag tgaactctgg cctaaagtag a                     51

SEQ ID NO: 147         moltype = DNA   length = 51
FEATURE                Location/Qualifiers
source                 1..51
                       mol_type = genomic DNA
                       organism = Cannabis sativa
SEQUENCE: 147
gtgcttctca aggcttttc ttcaggaatt ttgatgctct tgctagtcgt t                      51

SEQ ID NO: 148         moltype = DNA   length = 51
FEATURE                Location/Qualifiers
source                 1..51
                       mol_type = genomic DNA
                       organism = Cannabis sativa
SEQUENCE: 148
tatataacta ctattcttcc tctaccattc tacttatttt cttttgata t                      51

SEQ ID NO: 149         moltype = DNA   length = 51
FEATURE                Location/Qualifiers
source                 1..51
                       mol_type = genomic DNA
                       organism = Cannabis sativa
SEQUENCE: 149
taaactatct caagccgatc actgcaaaca caaaatacca tgtcacaaaa c                     51

SEQ ID NO: 150         moltype = DNA   length = 51
FEATURE                Location/Qualifiers
source                 1..51
                       mol_type = genomic DNA
                       organism = Cannabis sativa
SEQUENCE: 150
ttgctaacat gggagcaaat atggcttctt atgatgctgc agttctcaac g                     51

SEQ ID NO: 151         moltype = DNA   length = 51
FEATURE                Location/Qualifiers
source                 1..51
                       mol_type = genomic DNA
                       organism = Cannabis sativa
SEQUENCE: 151
tccaaggtac attaaatggg tttcagggta cattagatgg atttcaaggt a                     51

SEQ ID NO: 152         moltype = DNA   length = 51
FEATURE                Location/Qualifiers
source                 1..51
                       mol_type = genomic DNA
                       organism = Cannabis sativa
SEQUENCE: 152
tgagtttggt ttgcaaccat ggagccctaa taagcttccc taccoctcag g                     51

SEQ ID NO: 153         moltype = DNA   length = 51
FEATURE                Location/Qualifiers
source                 1..51
                       mol_type = genomic DNA
                       organism = Cannabis sativa
SEQUENCE: 153
gaaaatattt acaaatttgc cacaacgttt cgttgacttg gaaaacaac c                      51

SEQ ID NO: 154         moltype = DNA   length = 51
FEATURE                Location/Qualifiers
source                 1..51
                       mol_type = genomic DNA
```

```
                        organism = Cannabis sativa
SEQUENCE: 154
tgtccgtgcc acctgcgtcg cagacgatag atcttcagac tttgtacaac g            51

SEQ ID NO: 155         moltype = DNA   length = 51
FEATURE                Location/Qualifiers
source                 1..51
                       mol_type = genomic DNA
                       organism = Cannabis sativa
SEQUENCE: 155
agacttacac cgtcctcgag gaacgtcatg agctcccgct tgtgagccgc c            51

SEQ ID NO: 156         moltype = DNA   length = 51
FEATURE                Location/Qualifiers
source                 1..51
                       mol_type = genomic DNA
                       organism = Cannabis sativa
SEQUENCE: 156
cccattatca tcaccactgc ataaagtcaa tgcaaccatt caaatagcaa t            51

SEQ ID NO: 157         moltype = DNA   length = 51
FEATURE                Location/Qualifiers
source                 1..51
                       mol_type = genomic DNA
                       organism = Cannabis sativa
SEQUENCE: 157
aacaaattgc tgctatgatt aggccgaaaa ccaagtaaaa tgaggcaaca a            51

SEQ ID NO: 158         moltype = DNA   length = 51
FEATURE                Location/Qualifiers
source                 1..51
                       mol_type = genomic DNA
                       organism = Cannabis sativa
SEQUENCE: 158
tctaatcata caaaatgtca ccccagtcac tgcataaacc acattttctc c            51

SEQ ID NO: 159         moltype = DNA   length = 51
FEATURE                Location/Qualifiers
source                 1..51
                       mol_type = genomic DNA
                       organism = Cannabis sativa
SEQUENCE: 159
aagattcacg caagaaaatt atatgtagta tcactattca ttcgaatggt a            51

SEQ ID NO: 160         moltype = DNA   length = 51
FEATURE                Location/Qualifiers
source                 1..51
                       mol_type = genomic DNA
                       organism = Cannabis sativa
SEQUENCE: 160
atccttaaac ttggagttga gcataaggat gcattattct cttcacttca t            51

SEQ ID NO: 161         moltype = DNA   length = 51
FEATURE                Location/Qualifiers
source                 1..51
                       mol_type = genomic DNA
                       organism = Cannabis sativa
SEQUENCE: 161
tcacagcact cattttctca tactttccgg ctttgccata agaatccaag a            51

SEQ ID NO: 162         moltype = DNA   length = 51
FEATURE                Location/Qualifiers
source                 1..51
                       mol_type = genomic DNA
                       organism = Cannabis sativa
SEQUENCE: 162
ggtgtcgctt tgtcttaatg atcttttggc tataatagat tgcttatctg t            51

SEQ ID NO: 163         moltype = DNA   length = 51
FEATURE                Location/Qualifiers
source                 1..51
                       mol_type = genomic DNA
                       organism = Cannabis sativa
SEQUENCE: 163
tattggacaa tttttgttgt caatatggtc atagtgtcaa ctaaccatt g             51

SEQ ID NO: 164         moltype = DNA   length = 51
FEATURE                Location/Qualifiers
source                 1..51
```

```
                        mol_type = genomic DNA
                        organism = Cannabis sativa
SEQUENCE: 164
ttaaaataaa agataagttg gacaatattc taaattaatt aggtgtcaaa t           51

SEQ ID NO: 165          moltype = DNA  length = 51
FEATURE                 Location/Qualifiers
source                  1..51
                        mol_type = genomic DNA
                        organism = Cannabis sativa
SEQUENCE: 165
cacttcattg ttagaaatcg gtctttgatg tcaccctgat tcaagaaaag a           51

SEQ ID NO: 166          moltype = DNA  length = 51
FEATURE                 Location/Qualifiers
source                  1..51
                        mol_type = genomic DNA
                        organism = Cannabis sativa
SEQUENCE: 166
tacatcaccc aagcaaatta gctccagggg cgactttcat tgcttcaaat t           51

SEQ ID NO: 167          moltype = DNA  length = 51
FEATURE                 Location/Qualifiers
source                  1..51
                        mol_type = genomic DNA
                        organism = Cannabis sativa
SEQUENCE: 167
ctataatttt gaacacgtca tagccttaca cgtggcacca aaacgtctta c           51

SEQ ID NO: 168          moltype = DNA  length = 51
FEATURE                 Location/Qualifiers
source                  1..51
                        mol_type = genomic DNA
                        organism = Cannabis sativa
SEQUENCE: 168
ttaacaagaa atgtaactcc aatgctcacg gaatagtgaa tgaccgagtc a           51

SEQ ID NO: 169          moltype = DNA  length = 51
FEATURE                 Location/Qualifiers
source                  1..51
                        mol_type = genomic DNA
                        organism = Cannabis sativa
SEQUENCE: 169
aacaagagta taactcagga tactcaaaaa gggaagaaga tgattttcaa a           51

SEQ ID NO: 170          moltype = DNA  length = 51
FEATURE                 Location/Qualifiers
source                  1..51
                        mol_type = genomic DNA
                        organism = Cannabis sativa
SEQUENCE: 170
cggtgtggcg actattagcc tcgtatgcca tggcaagcca tatttgaatc t           51

SEQ ID NO: 171          moltype = DNA  length = 51
FEATURE                 Location/Qualifiers
source                  1..51
                        mol_type = genomic DNA
                        organism = Cannabis sativa
SEQUENCE: 171
gttgtctcgg gctgaatcgg ccggccaacg cgccgcctgg attggacgaa a           51

SEQ ID NO: 172          moltype = DNA  length = 51
FEATURE                 Location/Qualifiers
source                  1..51
                        mol_type = genomic DNA
                        organism = Cannabis sativa
SEQUENCE: 172
gcttcttaaa tttttgtggg gtttttgtga caaggaagga ggtggagaaa t           51

SEQ ID NO: 173          moltype = DNA  length = 51
FEATURE                 Location/Qualifiers
source                  1..51
                        mol_type = genomic DNA
                        organism = Cannabis sativa
SEQUENCE: 173
gagttcatgg acagtattgg tgtaagttgt gatgcaattg ctcgtacagg a           51

SEQ ID NO: 174          moltype = DNA  length = 51
FEATURE                 Location/Qualifiers
```

```
source                  1..51
                        mol_type = genomic DNA
                        organism = Cannabis sativa
SEQUENCE: 174
cccaaacaaa caaataataa gtaatattaa ttaatcctaa cagagtgggt t            51

SEQ ID NO: 175          moltype = DNA   length = 51
FEATURE                 Location/Qualifiers
source                  1..51
                        mol_type = genomic DNA
                        organism = Cannabis sativa
SEQUENCE: 175
taggacggtt acctaatttt catacaatta attataaaag gagaagtttg t            51

SEQ ID NO: 176          moltype = DNA   length = 51
FEATURE                 Location/Qualifiers
source                  1..51
                        mol_type = genomic DNA
                        organism = Cannabis sativa
SEQUENCE: 176
tatttgaggg aggcatagac ccagtggtgg ctgaagagtg gatgagttgc a            51

SEQ ID NO: 177          moltype = DNA   length = 51
FEATURE                 Location/Qualifiers
source                  1..51
                        mol_type = genomic DNA
                        organism = Cannabis sativa
SEQUENCE: 177
aacatagtat ttagtcacaa gttgttacta atttaatttt agtcacaaca a            51

SEQ ID NO: 178          moltype = DNA   length = 51
FEATURE                 Location/Qualifiers
source                  1..51
                        mol_type = genomic DNA
                        organism = Cannabis sativa
SEQUENCE: 178
ggcgagctgg tgataatttg attgccaaaa tgaaagagag atctttaaat t            51

SEQ ID NO: 179          moltype = DNA   length = 51
FEATURE                 Location/Qualifiers
source                  1..51
                        mol_type = genomic DNA
                        organism = Cannabis sativa
SEQUENCE: 179
tttgtgctcg atcttcatca atgtcgctag cagtggttgc aaaaggatga t            51

SEQ ID NO: 180          moltype = DNA   length = 51
FEATURE                 Location/Qualifiers
source                  1..51
                        mol_type = genomic DNA
                        organism = Cannabis sativa
SEQUENCE: 180
ttcttgaatt gtgatcccaa atttggatcc acaagctcca ttatatctcc c            51

SEQ ID NO: 181          moltype = DNA   length = 51
FEATURE                 Location/Qualifiers
source                  1..51
                        mol_type = genomic DNA
                        organism = Cannabis sativa
SEQUENCE: 181
tatttgcaag gctattgttt tccatgtact cataaaccag caacaattgc t            51

SEQ ID NO: 182          moltype = DNA   length = 51
FEATURE                 Location/Qualifiers
source                  1..51
                        mol_type = genomic DNA
                        organism = Cannabis sativa
SEQUENCE: 182
cataacaaag ctactttaat cattcgaaat acttcttcgt ggttgaactc g            51

SEQ ID NO: 183          moltype = DNA   length = 51
FEATURE                 Location/Qualifiers
source                  1..51
                        mol_type = genomic DNA
                        organism = Cannabis sativa
SEQUENCE: 183
atttccatgc aaagaagaag tagtaagaat acaattacat catggagtat a            51

SEQ ID NO: 184          moltype = DNA   length = 51
```

```
FEATURE                 Location/Qualifiers
source                  1..51
                        mol_type = genomic DNA
                        organism = Cannabis sativa
SEQUENCE: 184
tttctgttca tgctagttta ggtaagtggt gggagtgtct taagcttttt g          51

SEQ ID NO: 185          moltype = DNA   length = 51
FEATURE                 Location/Qualifiers
source                  1..51
                        mol_type = genomic DNA
                        organism = Cannabis sativa
SEQUENCE: 185
cgtcgattat gggctgacgc gtttctctcc atgggcccta ctaccctcca a          51

SEQ ID NO: 186          moltype = DNA   length = 51
FEATURE                 Location/Qualifiers
source                  1..51
                        mol_type = genomic DNA
                        organism = Cannabis sativa
SEQUENCE: 186
tatacagact atagtcaata ttaaatcatt attattaatt tcatatataa t          51

SEQ ID NO: 187          moltype = DNA   length = 51
FEATURE                 Location/Qualifiers
source                  1..51
                        mol_type = genomic DNA
                        organism = Cannabis sativa
SEQUENCE: 187
atccagcttc tactaacaat ggtaagtttt ataccaaata tcataatttc t          51

SEQ ID NO: 188          moltype = DNA   length = 51
FEATURE                 Location/Qualifiers
source                  1..51
                        mol_type = genomic DNA
                        organism = Cannabis sativa
SEQUENCE: 188
agttgatggc gttcatggcg tcgtcgattc gattcctctg gaattggtag t          51

SEQ ID NO: 189          moltype = DNA   length = 51
FEATURE                 Location/Qualifiers
source                  1..51
                        mol_type = genomic DNA
                        organism = Cannabis sativa
SEQUENCE: 189
ccttctgaca gctcggagga aggatgctcg ttcggtgaag attaagagaa g          51

SEQ ID NO: 190          moltype = DNA   length = 51
FEATURE                 Location/Qualifiers
source                  1..51
                        mol_type = genomic DNA
                        organism = Cannabis sativa
SEQUENCE: 190
ttttattatt ttttcacaca attaacaatg agactcttta ataacaacaa c          51

SEQ ID NO: 191          moltype = DNA   length = 51
FEATURE                 Location/Qualifiers
source                  1..51
                        mol_type = genomic DNA
                        organism = Cannabis sativa
SEQUENCE: 191
atctgggttg ttctgttcct tctcatggaa atcttgaaaa atgggctgtt c          51

SEQ ID NO: 192          moltype = DNA   length = 51
FEATURE                 Location/Qualifiers
source                  1..51
                        mol_type = genomic DNA
                        organism = Cannabis sativa
SEQUENCE: 192
ttgggttggt cccaaaaccg gatttgagaa tgtgggtgtg gagcagaggt g          51

SEQ ID NO: 193          moltype = DNA   length = 51
FEATURE                 Location/Qualifiers
source                  1..51
                        mol_type = genomic DNA
                        organism = Cannabis sativa
SEQUENCE: 193
ataaatgaaa ttctctattt ccctcaatac aatttgatta tttgatccat a          51
```

| | | |
|---|---|---|
| SEQ ID NO: 194 | moltype = DNA length = 51 | |
| FEATURE | Location/Qualifiers | |
| source | 1..51 | |
| | mol_type = genomic DNA | |
| | organism = Cannabis sativa | |
| SEQUENCE: 194 | | |
| tagcaagaga atcagttgca gcgttcgtaa gacgctcttt caaggtgttc t | | 51 |
| | | |
| SEQ ID NO: 195 | moltype = DNA length = 51 | |
| FEATURE | Location/Qualifiers | |
| source | 1..51 | |
| | mol_type = genomic DNA | |
| | organism = Cannabis sativa | |
| SEQUENCE: 195 | | |
| ggttcaggac aaggagaaag agactgagta agattaggca tagcaaagaa a | | 51 |
| | | |
| SEQ ID NO: 196 | moltype = DNA length = 51 | |
| FEATURE | Location/Qualifiers | |
| source | 1..51 | |
| | mol_type = genomic DNA | |
| | organism = Cannabis sativa | |
| SEQUENCE: 196 | | |
| ggtgtaaaat tgttaccatt ttgttgtttt tattttcagt gtgagttgtt t | | 51 |
| | | |
| SEQ ID NO: 197 | moltype = DNA length = 51 | |
| FEATURE | Location/Qualifiers | |
| source | 1..51 | |
| | mol_type = genomic DNA | |
| | organism = Cannabis sativa | |
| SEQUENCE: 197 | | |
| aaatagcagt agctatagct agcttgttat tatattaggc atgtgcattg c | | 51 |
| | | |
| SEQ ID NO: 198 | moltype = DNA length = 51 | |
| FEATURE | Location/Qualifiers | |
| source | 1..51 | |
| | mol_type = genomic DNA | |
| | organism = Cannabis sativa | |
| SEQUENCE: 198 | | |
| acactgctcc caatccaaag gtagaggatc tttcagttga agatcaacgc t | | 51 |
| | | |
| SEQ ID NO: 199 | moltype = DNA length = 51 | |
| FEATURE | Location/Qualifiers | |
| source | 1..51 | |
| | mol_type = genomic DNA | |
| | organism = Cannabis sativa | |
| SEQUENCE: 199 | | |
| attggaatag taagtcttta gccttcgtta acagcatatt ggcaaacact a | | 51 |
| | | |
| SEQ ID NO: 200 | moltype = DNA length = 51 | |
| FEATURE | Location/Qualifiers | |
| source | 1..51 | |
| | mol_type = genomic DNA | |
| | organism = Cannabis sativa | |
| SEQUENCE: 200 | | |
| gtgtgattat gtcaaagaaa aagacaaaca tgttggatat attttaccag g | | 51 |
| | | |
| SEQ ID NO: 201 | moltype = DNA length = 51 | |
| FEATURE | Location/Qualifiers | |
| source | 1..51 | |
| | mol_type = genomic DNA | |
| | organism = Cannabis sativa | |
| SEQUENCE: 201 | | |
| atttgtattg tcctttccaa ctacccttta ggtacctatg atgatgatgg g | | 51 |
| | | |
| SEQ ID NO: 202 | moltype = DNA length = 51 | |
| FEATURE | Location/Qualifiers | |
| source | 1..51 | |
| | mol_type = genomic DNA | |
| | organism = Cannabis sativa | |
| SEQUENCE: 202 | | |
| aataattgtt ggaattattt taccaggatc ttagatctac tcacaagtat g | | 51 |
| | | |
| SEQ ID NO: 203 | moltype = DNA length = 51 | |
| FEATURE | Location/Qualifiers | |
| source | 1..51 | |
| | mol_type = genomic DNA | |
| | organism = Cannabis sativa | |
| SEQUENCE: 203 | | |
| gtcatgattg tatattaaaa tctctcataa taaaaattaa agatatatgt a | | 51 |

```
SEQ ID NO: 204         moltype = DNA  length = 51
FEATURE                Location/Qualifiers
source                 1..51
                       mol_type = genomic DNA
                       organism = Cannabis sativa
SEQUENCE: 204
catcagaccg agaaaacttg gacaccaggc ttgttcgaag ccgcacgcac c            51

SEQ ID NO: 205         moltype = DNA  length = 51
FEATURE                Location/Qualifiers
source                 1..51
                       mol_type = genomic DNA
                       organism = Cannabis sativa
SEQUENCE: 205
aaatttaatt aattttctaa tatttaaaat aattaaatta tgtacccaat a            51

SEQ ID NO: 206         moltype = DNA  length = 51
FEATURE                Location/Qualifiers
source                 1..51
                       mol_type = genomic DNA
                       organism = Cannabis sativa
SEQUENCE: 206
tctttaaata tttgataatg agaatcccat tttgttttag cacgtcatac g            51

SEQ ID NO: 207         moltype = DNA  length = 51
FEATURE                Location/Qualifiers
source                 1..51
                       mol_type = genomic DNA
                       organism = Cannabis sativa
SEQUENCE: 207
gtgcttaaaa tcccatccaa actcaagacc cacaattttt atataatata t            51

SEQ ID NO: 208         moltype = DNA  length = 51
FEATURE                Location/Qualifiers
source                 1..51
                       mol_type = genomic DNA
                       organism = Cannabis sativa
SEQUENCE: 208
gagtttcttg tgagatggcg gcgttgattg aagtttggat agtagaaagt g            51

SEQ ID NO: 209         moltype = DNA  length = 51
FEATURE                Location/Qualifiers
source                 1..51
                       mol_type = genomic DNA
                       organism = Cannabis sativa
SEQUENCE: 209
ttgttgttgg tgaatctaat cagtggttat ttagtttgag aaaataaaaa t            51

SEQ ID NO: 210         moltype = DNA  length = 51
FEATURE                Location/Qualifiers
source                 1..51
                       mol_type = genomic DNA
                       organism = Cannabis sativa
SEQUENCE: 210
ttagtttaaa agggatgaaa atatagaatg aagtcttatt atccatgcat t            51

SEQ ID NO: 211         moltype = DNA  length = 51
FEATURE                Location/Qualifiers
source                 1..51
                       mol_type = genomic DNA
                       organism = Cannabis sativa
SEQUENCE: 211
catcattctc atattattac taaaaggctc atggctaaag atactagtca c            51

SEQ ID NO: 212         moltype = DNA  length = 51
FEATURE                Location/Qualifiers
source                 1..51
                       mol_type = genomic DNA
                       organism = Cannabis sativa
SEQUENCE: 212
ttttaaaata caaggtacta aataagcatt attaaaaata cagggtacaa a            51

SEQ ID NO: 213         moltype = DNA  length = 51
FEATURE                Location/Qualifiers
source                 1..51
                       mol_type = genomic DNA
                       organism = Cannabis sativa
SEQUENCE: 213
```

```
aatgtgcgac cgagacaagg tgtagtcgcg cactatgcat ggcatagcaa a          51

SEQ ID NO: 214         moltype = DNA   length = 51
FEATURE                Location/Qualifiers
source                 1..51
                       mol_type = genomic DNA
                       organism = Cannabis sativa
SEQUENCE: 214
aaaatcagca agctgctcat ttacttcttt gtaagagtgt gtgtgttgtg t          51

SEQ ID NO: 215         moltype = DNA   length = 51
FEATURE                Location/Qualifiers
source                 1..51
                       mol_type = genomic DNA
                       organism = Cannabis sativa
SEQUENCE: 215
tggttttat ttatttattt ttttgagaaa aaaacttcaa aacccacctt t           51

SEQ ID NO: 216         moltype = DNA   length = 51
FEATURE                Location/Qualifiers
source                 1..51
                       mol_type = genomic DNA
                       organism = Cannabis sativa
SEQUENCE: 216
acaaaaactt aacctgcaga gatgggtacc cacaagtacc caccccaaat g          51

SEQ ID NO: 217         moltype = DNA   length = 51
FEATURE                Location/Qualifiers
source                 1..51
                       mol_type = genomic DNA
                       organism = Cannabis sativa
SEQUENCE: 217
gtggaggaaa tttcttggct ttctcaagtg aggccccaaa gaagtgtgtg t          51

SEQ ID NO: 218         moltype = DNA   length = 51
FEATURE                Location/Qualifiers
source                 1..51
                       mol_type = genomic DNA
                       organism = Cannabis sativa
SEQUENCE: 218
ggagagctag ctatagctaa ttaaaatttt aaattatgaa ataataaaca a          51

SEQ ID NO: 219         moltype = DNA   length = 51
FEATURE                Location/Qualifiers
source                 1..51
                       mol_type = genomic DNA
                       organism = Cannabis sativa
SEQUENCE: 219
tggtataatc tattttgaac aaatgagatg atctagcata aacgttttat t          51

SEQ ID NO: 220         moltype = DNA   length = 51
FEATURE                Location/Qualifiers
source                 1..51
                       mol_type = genomic DNA
                       organism = Cannabis sativa
SEQUENCE: 220
catgaacacg tagataagta atcaacagtt aagattagac aagaaaatgt g          51

SEQ ID NO: 221         moltype = DNA   length = 51
FEATURE                Location/Qualifiers
source                 1..51
                       mol_type = genomic DNA
                       organism = Cannabis sativa
SEQUENCE: 221
ctctaagaga tggaattgaa gaaaacctca aggactgaga atggagctgc t          51

SEQ ID NO: 222         moltype = DNA   length = 51
FEATURE                Location/Qualifiers
source                 1..51
                       mol_type = genomic DNA
                       organism = Cannabis sativa
SEQUENCE: 222
atggatcttg gtttagtata gagtaaaatc tcaagtaact tgtgcttggt a          51

SEQ ID NO: 223         moltype = DNA   length = 51
FEATURE                Location/Qualifiers
source                 1..51
                       mol_type = genomic DNA
                       organism = Cannabis sativa
```

```
SEQUENCE: 223
aatggtgcag tgcagagggt ggtgtggcat gtgctacagt aacaggccca g            51

SEQ ID NO: 224          moltype = DNA   length = 51
FEATURE                 Location/Qualifiers
source                  1..51
                        mol_type = genomic DNA
                        organism = Cannabis sativa
SEQUENCE: 224
atatcaggca ttgtggtaga gaaaacgttc aatcataata gaaaacaaca a            51

SEQ ID NO: 225          moltype = DNA   length = 51
FEATURE                 Location/Qualifiers
source                  1..51
                        mol_type = genomic DNA
                        organism = Cannabis sativa
SEQUENCE: 225
tgcatcgagg ctgcaaagtt tgttttctt gatcgaacaa ggggggttgtt g            51

SEQ ID NO: 226          moltype = DNA   length = 51
FEATURE                 Location/Qualifiers
source                  1..51
                        mol_type = genomic DNA
                        organism = Cannabis sativa
SEQUENCE: 226
ctcgcattct caatctcctc tccattcatg gtagatctcc aacttctctg a            51

SEQ ID NO: 227          moltype = DNA   length = 51
FEATURE                 Location/Qualifiers
source                  1..51
                        mol_type = genomic DNA
                        organism = Cannabis sativa
SEQUENCE: 227
cccgagccat atgccacaga gaacaacttt ttgtctcttc aaggtacacg c            51

SEQ ID NO: 228          moltype = DNA   length = 51
FEATURE                 Location/Qualifiers
source                  1..51
                        mol_type = genomic DNA
                        organism = Cannabis sativa
SEQUENCE: 228
tctctctctc ttcagacata taccttagc tccctatta tttctactat c              51

SEQ ID NO: 229          moltype = DNA   length = 51
FEATURE                 Location/Qualifiers
source                  1..51
                        mol_type = genomic DNA
                        organism = Cannabis sativa
SEQUENCE: 229
gaaatccagt ccaaaggcac aaaactgttt cttcaagaat gtaccaccta a            51

SEQ ID NO: 230          moltype = DNA   length = 51
FEATURE                 Location/Qualifiers
source                  1..51
                        mol_type = genomic DNA
                        organism = Cannabis sativa
SEQUENCE: 230
acgtaccggg aaagaatttt ccgatgatac gaaggatctt gcgaccttgt t            51

SEQ ID NO: 231          moltype = DNA   length = 51
FEATURE                 Location/Qualifiers
source                  1..51
                        mol_type = genomic DNA
                        organism = Cannabis sativa
SEQUENCE: 231
atcaatgaag aagaagggtc atccaaaaca agggggtttca actgagctaa c           51

SEQ ID NO: 232          moltype = DNA   length = 51
FEATURE                 Location/Qualifiers
source                  1..51
                        mol_type = genomic DNA
                        organism = Cannabis sativa
SEQUENCE: 232
tcatgggaaa agtgatggaa gttttttaaac ccggggctgt ggttcttcag t           51

SEQ ID NO: 233          moltype = DNA   length = 51
FEATURE                 Location/Qualifiers
source                  1..51
                        mol_type = genomic DNA
```

```
                        organism = Cannabis sativa
SEQUENCE: 233
tggctggcta gacaaggatg ccattgttat aaattaatga tgttgatcaa t            51

SEQ ID NO: 234          moltype = DNA   length = 51
FEATURE                 Location/Qualifiers
source                  1..51
                        mol_type = genomic DNA
                        organism = Cannabis sativa
SEQUENCE: 234
cgtaaaattt atttttaaaa tattaaaaat catttcttac aggctgacct a            51

SEQ ID NO: 235          moltype = DNA   length = 51
FEATURE                 Location/Qualifiers
source                  1..51
                        mol_type = genomic DNA
                        organism = Cannabis sativa
SEQUENCE: 235
gtggagagaa aagcataagc aaatttacaa atttacaagt cagcaaattt t            51

SEQ ID NO: 236          moltype = DNA   length = 51
FEATURE                 Location/Qualifiers
source                  1..51
                        mol_type = genomic DNA
                        organism = Cannabis sativa
SEQUENCE: 236
ttaaatatac taataagaaa atgacacttg gataataact tgaaacttaa c            51

SEQ ID NO: 237          moltype = DNA   length = 51
FEATURE                 Location/Qualifiers
source                  1..51
                        mol_type = genomic DNA
                        organism = Cannabis sativa
SEQUENCE: 237
attttgagag aaagagatag agagaggggg gcgggtttga ggcaaatgaa c            51

SEQ ID NO: 238          moltype = DNA   length = 51
FEATURE                 Location/Qualifiers
source                  1..51
                        mol_type = genomic DNA
                        organism = Cannabis sativa
SEQUENCE: 238
ctttcggaga gaaaaagaag aagttccaga ctccccaact aaagattttt t            51

SEQ ID NO: 239          moltype = DNA   length = 51
FEATURE                 Location/Qualifiers
source                  1..51
                        mol_type = genomic DNA
                        organism = Cannabis sativa
SEQUENCE: 239
ggacccgaaa gccctgtcat ccctctagga cctagagaag accaaatcaa c            51

SEQ ID NO: 240          moltype = DNA   length = 51
FEATURE                 Location/Qualifiers
source                  1..51
                        mol_type = genomic DNA
                        organism = Cannabis sativa
SEQUENCE: 240
cacttcttat tcggtgtcat tcgatcaagc tttgtaaaaa actttggtgg t            51

SEQ ID NO: 241          moltype = DNA   length = 51
FEATURE                 Location/Qualifiers
source                  1..51
                        mol_type = genomic DNA
                        organism = Cannabis sativa
SEQUENCE: 241
gaaatgaatt ataaaagtag tgagtaagca aaactttcac agcagccaca t            51

SEQ ID NO: 242          moltype = DNA   length = 51
FEATURE                 Location/Qualifiers
source                  1..51
                        mol_type = genomic DNA
                        organism = Cannabis sativa
SEQUENCE: 242
tataatcaat agaataagat aggacctact attgtttgtt tgttcaacca a            51

SEQ ID NO: 243          moltype = DNA   length = 5123
FEATURE                 Location/Qualifiers
source                  1..5123
```

```
                    mol_type = genomic DNA
                    organism = Cannabis sativa
SEQUENCE: 243
tataaagtaa ttttacaagt attattatta ttatgctcac cataacaaca acactcacaa    60
aataaataat tcctttgtca caattactac ttacttccta agcattatac acatgctaga   120
gtaattcatc tccataaaaa aaatattcgt cactataaaa taaaatttat ttgtcattaa   180
aatccttaat tcacaatatt caaaatacta aatgaaaaa aaaaataaat ggaagtaaaa    240
atagaattaa attcttattt tttttttcct taaaaaatg gatattacac cattctcatt    300
gctttgttat tggtggtagt ttagaggctc ctcaattatg cagggagggt ggcctacatt   360
accatccctc catcaatggt gagaacctac aaaacatgtt acagaaagtt cattcaagta   420
tgagaagtta aaattgttca agaaaaaaa aaaaagaaag tatgagaagt taaaatcaat    480
taactcttca aaacccaatt catagtaggt gaaagtgaaa cctgtccagt tatgtaactt   540
gcagcaggac caagtgccaa aaattccact agcccagcaa cttcttctgg ttgaccatat   600
cttcctgaag aacaatagaa atcacactaa tcttcacata tttttctcaa caattcagag   660
gagtcagagc caagtcgata tgaagaaaga acaggattgt ctcagcctca ctcacctaag   720
gggatgccct ccaagttttt cttctcaata tcatctccta gcttggcagt catgtcagat   780
gcaataaagc ctgagcaat agcattaacc tgacaacaac aattcaatat tagtcatatt   840
gaaatatcta attatttgaa aaaaaaact ttggaataac tcacagtgat gtttctgctg    900
gaatactcct tagcaatagc ttttgtgaag ccaattactc ctgcttttgc agcactataa   960
ttggcttgcc cggcattgcc gactagaccg aagactgatg ctacattgat tatccttccc  1020
tacaaaatta ttatttgggg actaagaaaa taaacaaaaa aacgagacac aaagtaaact  1080
tcggcaaatc attctcaaaa gactaagcct gtgagaaaat aatgcccaag tggttataaa  1140
agtagtcaat cccatactcg ataaaggatc ctaacagtaa accattttta gagaggatgt  1200
ccatgacagc aaccctcttt gggtttctcc acaggtcatc ctttccatga catggtcccc  1260
gagagggtgc tcattttgat attgaaatta tatgtcgaaa tattcaatat aaaaatagtt  1320
ttgactgtaa atggagagat aaaacggtgt atataccttt ttcttcttca tcataatttt  1380
ggctgcagcc tgcaaataaa gaattaattt tagtttcgag aaaaagtcaa gtttgaagga  1440
ccttaagaag tgaaagcttt agatgcacac ctgtgtacat agaaatacac cagtaagatt  1500
caaatcaatg acatcctgcc actgggattt cttcattctc ataattaagt tgtcccttgt  1560
gattcctgaa aacaccgaaa aagcatcagg agatcgatg tggaatgaaa acaacataag  1620
aaaatgaaag tttcaaacaa cctgcattat ttactaatac atcaatagtt ccccaagcat  1680
caactgcctg caggtttatg agatggaata ttacaaacca ttccacggtt taacatacaa  1740
tgtgaaaaaa caatatgaag aacattttct cactgttttg atcattaatt caacatcagc  1800
ttcttttgaa acatctcctc caaaagtaat agcttggcca ccagatgctt cgatctgtaa  1860
gaactcagtc aaaattattt ttgatggtgg ttgaactaca taagaaaat aaatacaaaa  1920
gtctagaatc tactaaatca ggaaaggaaa ggcatttgac caattaaaaa ttatggaaga  1980
taattcttgc actgctgtaa ctgaaactat tagtaatcaa atcatcacag aattgaggtt  2040
tgaattgatg tcaagtattg ttatagagaa ggaaaaagaa ctaatataca agttagaaaa  2100
cataaacata agaaaaaaat gacgctctta tattcatttt gaatcacatt ataagtataa  2160
ataatacact gcgtttggtt ggaggtaatg aaatagaata aaaaggaaac aatatttatt  2220
ctattctttt gtttggttgc atattaaagt attgaaatat cattccaatg gaattgtcgt  2280
tccaccattt tggtagagtg actattctat tttgaaataa aaggaaagac tattccaata  2340
cacgatgaa aaatatttaa taattttttt tatcaatttt tttatgcatt ttaatttttat  2400
tccattctat tcctattctt atttccattc ccattcttat tcctatgttt ccattcttcc  2460
caaccaaacg ctaccttaaa ttcaaaacat tgaaaggggc taccccctctc ctcaaattgt  2520
atgcaatgtg ctcttagata atctgagtta tctacattgt atataatttt ctggtcccaa  2580
ataatattgc aggatataag gcaaggagcc taagtttaaa aaagggtagc aaaaaacatga  2640
atttaggact tctacaattg ctaaagtttc ccacaattgt aattccaata gttctgggc   2700
gctagtttca aaatatgcag ggccggttca gaaacaaagt gggtcacaag aaaaaaattt  2760
aggggtaagt tggaaaatac cactttatt aatcaattaa tcaaatttac ctctaatttt  2820
atatttaatt gaaacatacc tctttttata tgtattgtac ctaaaataacc ctgacataag  2880
agagtcgcat ggagagtatc ttgaagtgac aagggcaaaa tgtggtacaa tgtttaaaaa  2940
aaaaagaggt aaaaatgata gactttaaaa aagagggtaa aaatgaaaga ggacaatata  3000
aaaagggtat tgagtgtagt ttcctcaaaa atttattttt tggcccttat gttagaaaaa  3060
ttatggtatt tttcaaattc agtaaaaaaa ctatataatt ttaaaaggggg aaaaaaaat  3120
ttggccctag gcctaacccg catatctatt ctatataaag tgtgcctata taaccgaatt  3180
cttggtttat gagaaattca tgggtgactt tttatttata ttaaaaataa aatgatttat  3240
tattaaaaat aaatttatat taagaagcga gaagtataaa acgatgacgt gtcactctaa  3300
atttattcta aatgtaactt tctattctct ctttaattct ctcattata tattttttt   3360
aatcataact aaaattactaa ttattttca aaaaaataaa acaaataaaa ataatggtat  3420
acttcaaaat atcacaaact taatactaaa tttattgttt tcataaaact aaatcatccg  3480
tagcttattt ttaatgattt tttaatgttt tattttaaaa aatatccgta gctttttta   3540
atgattttt aatgttttat tttaaaataa taaaattaaa ttatccatca ctaacaattc  3600
atttttttt ttgaaattac taacaattct tttttaaatg tgcatcatta tatactttt   3660
ttcttagcac atatccgtag ttttttttt aatgattttt tatgtttat tttttttctt  3720
acatttatat tatctttaca gattaacaat aatttttttt ttttgtaagg agattaacaa  3780
taaactttga ttctcgattc aaatattatt tttcaatttt attttcatat attcaaaatt  3840
ctcattctat aaatttttca tcaatatttt gtaatcaatg aaacaaaaat gcaaactta   3900
attcccgtat gaaaaatcaa actctcaatc ccaataatta atagaaacaa catccaagttt  3960
caagttttca aaatttataa aaataaatac ataaataaat aaaaacatat ctcataaaca  4020
caaactcaaa tattagaacc ccagtaaaac actaaaacta aaacattaaa aacacacata  4080
ttagaataaa aattaaaacca taaatgaaaa tttatgctac tattttttcaa atttcgtat  4140
ttattagcaa caaatttaat attttaaggt cacaaatttt ttaatagtaa attcaaaatt  4200
ttaataat tttaaataagt aattatttt aagtaaaata tacaatttat tttttatata  4260
taatttaaaa tacttatac atccgcccgc cggcgaaccg cgaagcacag tatatatata  4320
tttatatttt atattgaaag ggataacaca aacatgaata gaacttgatg gaactcacct  4380
ctttggaaac ttcctcagcc tcctttgatg atctagcata attaacaagg acctatagta  4440
atagtatagc actatatcag aaaaagaaaa aacaaattac acacaacaaa gatcatcaat  4500
attgctaata aaaaaaaaaa acaaagatca tctcaatgaa ttggtaaaag ggaaaaccac  4560
```

```
aaaccttaca  accagctttt  cccaaagcca  atgcagtagc  ttttccaata  cctctagagg   4620
caccagtcac  aatgaccacc  ggagcctcca  cattttggcc  tactccggcg  cttgtttctt   4680
caagacttgc  tccctgagct  ttaacaacac  ctgaagaaga  agaagaagaa  gaggaactac   4740
catcatcgaa  atcccaaacc  cattaagaaa  aacaagtaat  cgtaccaccg  gaggaactct   4800
tggatttgca  ctgaagggag  atggattggc  ggagtgattg  gccaccggaa  atgggggacc   4860
actgccgaaa  atgtggggct  ttccggtcaa  agaatgagct  ggaaattctg  gttgatttgg   4920
aaactacaac  gtttgatcca  gcaatggcag  ccatgggata  tatagttccg  aagattgttg   4980
tgggctttgt  acaaagaaaa  aggcagagtt  tttagaaaac  ccagataaga  aattgaactg   5040
ttccttttcg  tgtttacgtt  ggtttttata  tattgggact  ttggaaactc  cgaagagtgt   5100
tcgtacatct  ttgacgacgg  aac                                             5123

SEQ ID NO: 244          moltype = AA  length = 322
FEATURE                 Location/Qualifiers
source                  1..322
                        mol_type = protein
                        organism = Cannabis sativa
SEQUENCE: 244
MAAIAGSNVV  VSKSTRISSS  FFDRKAPHFR  QWSPISGGQS  LRHSISLQCK  SKSSSGGVVK   60
AQGASLEETS  AGVGQNVEAP  VVIVTGASRG  IGKATALALG  KAGCKVLVNY  ARSSKEAEEV  120
SKEIEASGGQ  AITFGGDVSK  EADVELMIKT  AVDAWGTIDV  LVNNAGITRD  NLIMRMKKSQ  180
WQDVIDLNLT  GVFLCTQAAA  KIMMKKKKGR  IINVASVFGL  VGNAGQANYS  AAKAGVIGFT  240
KAIAKEYSSR  NITVNAIAPG  FIASDMTAKL  GDDIEKKNLE  GIPLGRYGQP  EEVAGLVEFL  300
ALGPAASYIT  GQVLTIDGGM  VM                                              322
```

VARIN MARKERS

CROSS REFERENCE TO RELATED APPLICATIONS

This application is a continuation under 35 USC §365(c) of International Application No. PCT/US2021/44908, filed Aug. 06, 2021, which claims priority benefit to U.S. provisional application No. 63/064,874, filed Aug. 12, 2020, the entire contents each of which are hereby incorporated by reference.

SEQUENCE LISTING REFERENCE

Pursuant to 37 CFR §§ 1.821-1.825, a Sequence Listing in the form of an ASCII-compliant text file (entitled "2004-US1_ST26_Sequence_listing.xml" created on Aug. 22, 2022 and 222,900 bytes in size), which will serve as both the paper copy required by 37 CFR § 1.821(c) and the computer readable form (CRF) required by 37 CFR § 1.821(e), is submitted concurrently with the instant application. The entire contents of the Sequence Listing are incorporated herein by reference.

BACKGROUND OF THE INVENTION

*Cannabis* plants contain over a hundred known cannabinoids, which bind to endogenous endocannabinoid receptors. Varinolic cannabinoids, as known as varins, are a type of cannabinoid compounds having three carbon atoms in their alkyl side chain instead of the five carbon atom alkyl side chains more commonly associated with cannabinoids. Two such varins are tetrahydrocannabivarin (THCV) and cannabidivarin (CBDV), which are homologues of tetrahydrocannabinol (THC) and cannabidiol (CBD), respectively. Each varin has a unique pharmacological profile and distinct molecular targets.

Tetrahydrocannabivarin (THCV) is a homologue of tetrahydrocannabinol (THC) with a unique pharmacological profile and distinct molecular targets. THCV is a cannabinoid receptor type 1 antagonist and cannabinoid receptor type 2 partial agonist. Δ8-THCV has also been shown to be a CB1 antagonist, an agonist of GPR55 and I-α-lysophosphatidylinositol (LPI), and activator of 5HT1A receptors. THCV promises potential benefits across a broad set of applications.

Tetrahydrocannabivarinic acid (THCVA) is the carboxylated precursor to THCV, and the compound present in *Cannabis* varieties. As mentioned herein, phytocannabinoids such as THCV are synthesized in the plant as acid forms (e.g., THCVA), and while some decarboxylation does occur in the plant, it increases significantly post-harvest and the kinetics increase at high temperatures.

THCV and CBDV have potential benefits across a broad set of applications. *Cannabis* strains or extracts with high THCV levels, for example, can be used as an agent for anticonvulsant activity, obesity-associated glucose intolerance, appetite suppression, anxiety management for PTSD, diabetic neuropathy, and major neuropathic and pain related pathologies. Another THCV application is that of an appetite suppressing compound. CBDV has been shown to have anti-epileptic and anticonvulsant activity. Cannabigerivarin (CBGV) is a non-psychoactive cannabinoid that is a homolog of CBG, and may have analgesic and anti-inflammatory properties.

Research and development as well as the sale of varin products has been limited due to low commonly occurring levels of varins, such as THCV, in *Cannabis* flower. The ability to produce *Cannabis* with high varin levels will create a platform for a new Cannabinoid category with differentiated, high margin products in both medical and recreational markets.

The most common way to create *Cannabis* varieties having modified varin activity is the use of traditional methods of breeding that select for segregated traits over multiple generations. However, traditional breeding methods are laborious and time-consuming. The invention described herein utilizes discovered markers that closely segregate with the KR/FABG/FabG1 gene for selecting varin attributes.

KR (β ketoacyl-acyl carrier protein (ACP) reductase, At1g24360) is also referred to as 3-oxoacyl-[acyl-carrier-protein] reductase. KR functions together with enoyl-ACP reductase (pt/mtER) to catalyze two of the reactions that constitute the core four-reaction cycle of the fatty acid biosynthesis (FAS) system, which iteratively elongates the THC acyl-chain by two carbon atoms per cycle (Guan et al. 2020, Plant Physiology 183(2): 517-529). In *Cannabis*, plastid fatty acid biosynthesis forms the precursor for the acyl chain in THC and THCV (Welling et al. 2019, Scientific Reports 9(1): 1-13). Allelic variation of KR likely produces a KR variant that results in a shorter propyl (3-carbon) side chain found in THCV instead of a pentyl (5-carbon) group found in THC.

The invention described herein solves the laborious and time-consuming issues of traditional breeding methods by providing *Cannabis* breeders with a specific and efficient method for creating *Cannabis* plants having modified varin activity, including increased THCV, CBDV, or CBGV activity.

SUMMARY OF THE INVENTION

The present teachings relate to the identification of markers associated with THCV, THCVA, CBDV, CBDVA, CBGV, or CBGVA production in *Cannabis* plants and their use in selecting *Cannabis* plants having modified THCV, THCVA, CBDV, CBDVA, CBGV, or CBGVA activity. In an embodiment, a method for selecting one or more plants having modified varin activity is provided. The method comprises i) obtaining nucleic acids from a sample plant or its germplasm; (ii) detecting one or more markers that indicate modified varin activity, and (iii) indicating modified varin activity. In an embodiment, the method further comprises selecting the one or more plants indicating modified varin activity. In an embodiment, the modified varin activity correlates to modified tetrahydrocannabivarin (THCV), tetrahydrocannabivarinic acid (THCVA), cannabidivarin (CBDV), cannabidivarinic acid (CBDVA), cannabigerivarin (CBGV), or cannabigerivarinic acid (CBGVA) levels. In an embodiment, the selecting comprises marker assisted selection. In an embodiment, the detecting comprises an oligonucleotide probe In an embodiment, the marker comprises as described in Table 2: (a) a polymorphism in the reference allele of the Abacus *Cannabis* reference genome on chromosome 1 relative to position 1,306,106; 1,408,650; 13,708, 867; 21,374,553; 33,426,602; 57,945,889; or 74,769,414; or (b) a polymorphism in the reference allele of the Abacus *Cannabis* reference genome on chromosome 2 relative to position 96,902,576; 5,078,822; 6,291,492; 68,155,237; or 82,116,647; or (c) a polymorphism in the reference allele of the Abacus *Cannabis* reference genome on chromosome 3 relative to position 601,392; 1,053,571; or 78,793,988; or (d) a polymorphism in the reference allele of the Abacus

*Cannabis* reference genome on chromosome 4 relative to position 72,717,623; 72,413,830; 72,330,901; 73,591,604; 69,742,048; 69,610,062; 76,062,454; 66,562,042; 72,070,492; 74,886,331; 72,386,361; 68,871,783; 72,500,945; 70,313,071; 68,551,901; 42,457,670; 75,695,688; 69,860,635; 65,944,497; 44,409,131; 59,679,717; 74,889,638; 42,260,741; 42,424,601; 42,459,658; 70,616,713; 70,604,032; 26,454,266; 70,623,580; 70,611,260; 62,122,798; 60,918,190; 65,379,561; 39,110,266; 44,819,952; 50,680,227; 44,601,335; 44,623,676; 44,629,900; 44,759,390; 44,867,872; 27,064,107; 44,672,313; 40,776,686; 61,163,234; 43,942,890; 28,202,114; 28,499,186; 28,655,285; 28,563,750; or 72,692,194; 35,933,381; 80,090,345; 80,115,357; 80,199,302; 80,229,056; 80,348,481; 80,353,319; 80,361,168; 80,365,496; 80,429,514; 80,467,768; 80,500,846; 80,554,549; 80,599,233; 79,698,853; 79,824,851; 79,972,170; 80,011,567; 80,012,804; 80,017,161; 80,028,174; 80,051,232; 80,072,595; 80,182,837; 80,299,232; 80,500,846; 80,543,937; or 80,591,401; or (e) a polymorphism in the reference allele of the Abacus *Cannabis* reference genome on chromosome 5 relative to position 42,019,510; or (f) a polymorphism in the reference allele of the Abacus *Cannabis* reference genome on chromosome 6 relative to position 1,477,638; 1,547,216; 9,352,336; 21,255,914; 21,288,458; 25,701,639; 46,375,436; 53,088,610; 54,422,975; 56,278,544; 63,262,835; 64,641,858; 82,769,380; 84,428,826; 54,569,276; 78,245,587; 78,551,191; 80,899,443; 83,711,056; or 20,354,173; or (g) a polymorphism in the reference allele of the Abacus *Cannabis* reference genome on chromosome 7 relative to position 60,682,036; 61,014,416; 60,842,314; 60,836,917; 60,726,211; 60,865,034; 61,689,496; 61,315,097; 61,384,518; 61,543,623; 61,391,296; 11,220,411; 41,986,329; 47,794,758; 58,418,614; 58,467,957; 58,607,780; 58,767,876; 58,788,342; 58,900,646; 58,949,513; 58,995,137; 59,119,856; 59,285,985; 59,294,013; 59,305,086; 59,349,246; 59,400,111; 59,457,070; 59,740,097; 59,769,614; 60,004,461; 60,246,243; 60,300,000; 60,405,904; 60,527,155; 60,730,565; 60,753,532; 60,943,279; 60,976,341; 60,994,423; 61,007,064; 61,258,755; 61,282,508; 61,305,861; 61,328,967; 61,504,547; 61,599,429; 61,645,795; 61,651,527; 61,658,656; 61,715,027; 61,989,002; 61,999,104; 62,019,912; 62,034,938; 62,231,000; 62,387,493; 62,647,527; 62,737,982; 62,742,884; 62,747,249; 62,761,203; 62,767,237; 62,792,364; 62,815,617; 62,850,589; 62,866,162; 62,870,580; 62,941,027; 62,971,551; 62,979,814; 62,993,205; 5,460,790; 27,884,762; 34,997,619; 45,591,259; 52,454,110; 57,247,955; or 58,720,667; or (h) a polymorphism in the reference allele of the Abacus *Cannabis* reference genome on chromosome 8 relative to position 23,016,846; or (i) a polymorphism in the reference allele of the Abacus *Cannabis* reference genome on chromosome 9 relative to position 12,654,209; 18,343,719; 27,937,504; 51,967,498; 58,316,394; 1,348,101; 16,113,998; 17,302,948; 17,687,309; 17,980,798; 20,457,181; 28,057,298; 34,290,160; 36,400,585; 45,840,334; 51,591,130; 51,751,347; 52,869,819; 57,745,083; 58,014,320; or 59,868,248; or (j) a polymorphism in the reference allele of the Abacus *Cannabis* reference genome on chromosome X relative to position 8,651,218; 12,403,249; 54,956,182; 56,498,195; 56,966,336; 66,516,851; 71,142,905; 71,618,503; 73,281,407; 73,399,713; 74,496,234; 74,627,738; 74,636,685; 74,863,601; 75,185,443; 75,920,615; 76,189,966; 78,539,112; 80,362,725; 80,424,310; 80,521,410; 80,551,750; 80,610,117; 81,555,347; or 81,636,223. In an embodiment, the polymorphism comprises the alternative nucleotide described in Table 2. In an embodiment, the marker comprises a polymorphism at position 26 of any one or more of SEQ ID NO:1; SEQ ID NO:2; SEQ ID NO:3; SEQ ID NO:4; SEQ ID NO:5; SEQ ID NO:6; SEQ ID NO:7; SEQ ID NO:8; SEQ ID NO:9; SEQ ID NO:10; SEQ ID NO:11; SEQ ID NO:12; SEQ ID NO:13; SEQ ID NO:14; SEQ ID NO:15; SEQ ID NO:16; SEQ ID NO:17; SEQ ID NO:18; SEQ ID NO:19; SEQ ID NO:20; SEQ ID NO:21; SEQ ID NO:22; SEQ ID NO:23; SEQ ID NO:24; SEQ ID NO:25; SEQ ID NO:26; SEQ ID NO:27; SEQ ID NO:28; SEQ ID NO:29; SEQ ID NO:30; SEQ ID NO:31; SEQ ID NO:32; SEQ ID NO:33; SEQ ID NO:34; SEQ ID NO:35; SEQ ID NO:36; SEQ ID NO:37; SEQ ID NO:38; SEQ ID NO:39; SEQ ID NO:40; SEQ ID NO:41; SEQ ID NO:42; SEQ ID NO:43; SEQ ID NO:44; SEQ ID NO:45; SEQ ID NO:46; SEQ ID NO:47; SEQ ID NO:48; SEQ ID NO:49; SEQ ID NO:50; SEQ ID NO:51; SEQ ID NO:52; SEQ ID NO:53; SEQ ID NO:54; SEQ ID NO:55; SEQ ID NO:56; SEQ ID NO:57; SEQ ID NO:58; SEQ ID NO:59; SEQ ID NO:60; SEQ ID NO:61; SEQ ID NO:62; SEQ ID NO:63; SEQ ID NO:64; SEQ ID NO:65; SEQ ID NO:66; SEQ ID NO:67; SEQ ID NO:68; SEQ ID NO:69; SEQ ID NO:70; SEQ ID NO:71; SEQ ID NO:72; SEQ ID NO:73; SEQ ID NO:74; SEQ ID NO:75; SEQ ID NO:76; SEQ ID NO:77; SEQ ID NO:78; SEQ ID NO:79; SEQ ID NO:80; SEQ ID NO:81; SEQ ID NO:82; SEQ ID NO:83; SEQ ID NO:84; SEQ ID NO:85; SEQ ID NO:86; SEQ ID NO:87; SEQ ID NO:88; SEQ ID NO:89; SEQ ID NO:90; SEQ ID NO:91; SEQ ID NO:92; SEQ ID NO:93; SEQ ID NO:94; SEQ ID NO:95; SEQ ID NO:96; SEQ ID NO:97; SEQ ID NO:98; SEQ ID NO:99; SEQ ID NO:100; SEQ ID NO:101; SEQ ID NO:102; SEQ ID NO:103; SEQ ID NO:104; SEQ ID NO:105; SEQ ID NO:106; SEQ ID NO:107; SEQ ID NO:108; SEQ ID NO:109; SEQ ID NO:110; SEQ ID NO:111; SEQ ID NO:112; SEQ ID NO:113; SEQ ID NO:114; SEQ ID NO:115; SEQ ID NO:116; SEQ ID NO:117; SEQ ID NO:118; SEQ ID NO:119; SEQ ID NO:120; SEQ ID NO:121; SEQ ID NO:122; SEQ ID NO:123; SEQ ID NO:124; SEQ ID NO:125; SEQ ID NO:126; SEQ ID NO:127; SEQ ID NO:128; SEQ ID NO:129; SEQ ID NO:130; SEQ ID NO:131; SEQ ID NO:132; SEQ ID NO:133; SEQ ID NO:134; SEQ ID NO:135; SEQ ID NO:136; SEQ ID NO:137; SEQ ID NO:138; SEQ ID NO:139; SEQ ID NO:140; SEQ ID NO:141; SEQ ID NO:142; SEQ ID NO:143; SEQ ID NO:144; SEQ ID NO:145; SEQ ID NO:146; SEQ ID NO:147; SEQ ID NO:148; SEQ ID NO:149; SEQ ID NO:150; SEQ ID NO:151; SEQ ID NO:152; SEQ ID NO:153; SEQ ID NO:154; SEQ ID NO:155; SEQ ID NO:156; SEQ ID NO:157; SEQ ID NO:158; SEQ ID NO:159; SEQ ID NO:160; SEQ ID NO:161; SEQ ID NO:162; SEQ ID NO:163; SEQ ID NO:164; SEQ ID NO:165; SEQ ID NO:166; SEQ ID NO:167; SEQ ID NO:168; SEQ ID NO:169; SEQ ID NO:170; SEQ ID NO:171; SEQ ID NO:172; SEQ ID NO:173; SEQ ID NO:174; SEQ ID NO:175; SEQ ID NO:176; SEQ ID NO:177; SEQ ID NO:178; SEQ ID NO:179; SEQ ID NO:180; SEQ ID NO:181; SEQ ID NO:182; SEQ ID NO:183; SEQ ID NO:184; SEQ ID NO:185; SEQ ID NO:186; SEQ ID NO:187; SEQ ID NO:188; SEQ ID NO:189; SEQ ID NO:190; SEQ ID NO:191; SEQ ID NO:192; SEQ ID NO:193; SEQ ID NO:194; SEQ ID NO:195; SEQ ID NO:196; SEQ ID NO:197; SEQ ID NO:198; SEQ ID NO:199; SEQ ID NO:200; SEQ ID NO:201; SEQ ID NO:202; SEQ ID NO:203; SEQ ID NO:204; SEQ ID NO:205; SEQ ID NO:206; SEQ ID NO:207; SEQ ID NO:208; SEQ ID NO:209; SEQ ID NO:210; SEQ ID NO:211; SEQ ID NO:212; SEQ ID NO:213; SEQ ID NO:214; SEQ ID NO:215; SEQ ID NO:216; SEQ ID NO:217; SEQ ID NO218; SEQ ID NO:219; SEQ ID NO:220; SEQ ID NO:221; SEQ ID NO:222; SEQ ID NO:223; SEQ ID NO:224; SEQ ID NO:225; SEQ ID NO:226; SEQ ID NO:227; SEQ ID NO:228; SEQ ID NO:229; SEQ ID NO:230; SEQ ID NO:231; SEQ ID NO:232; SEQ ID NO:233; SEQ ID NO:234; SEQ ID NO:235; SEQ ID NO:236; SEQ ID NO:237; SEQ ID NO:238; SEQ ID NO:239; SEQ ID NO:240; SEQ ID NO:241; or SEQ ID NO:242. In an embodiment, the polymorphism comprises the alternative nucleotide call described in Table 2. In an embodiment, the one or more markers comprise a polymorphism in the reference allele of the Abacus *Cannabis* reference genome within any one or more haplotypes described in Table 2. In an embodiment, the haplotype is defined as: (a) chromosome 4 anywhere between positions 69,222,980 and 74,594,736; or (b) chromosome 7 anywhere between positions 56,158,064 and 61,821,470 of the Abacus *Cannabis* reference genome. In an embodiment, the method further comprises crossing the one or more plants comprising the indicated modified varin activity to produce one or more F1 or additional progeny plants, wherein at least one of the F1 or additional progeny plants comprises the indicated modified varin activity activity. In an embodiment, the crossing comprises selfing, sibling crossing, or backcrossing. In an embodiment, the at least one additional progeny plant comprising the indicated modified varin activity is an F2-F7 progeny plant. In an embodiment, the selfing, sibling crossing, or backcrossing comprises marker-assisted selection. In an embodiment, the selfing, sibling crossing, or backcrossing comprises marker-assisted selection for at least two generations. In an embodiment, the modified varin activity is an increase in THCV and/or CBDV levels. In an embodiment, the plant is a *Cannabis* plant.

BRIEF DESCRIPTION OF THE DRAWINGS

The skilled artisan will understand that the drawings, described below, are for illustration purposes only. The drawings are not intended to limit the scope of the present teachings in any way.

DETAILED DESCRIPTION OF THE INVENTION

Figure 1:
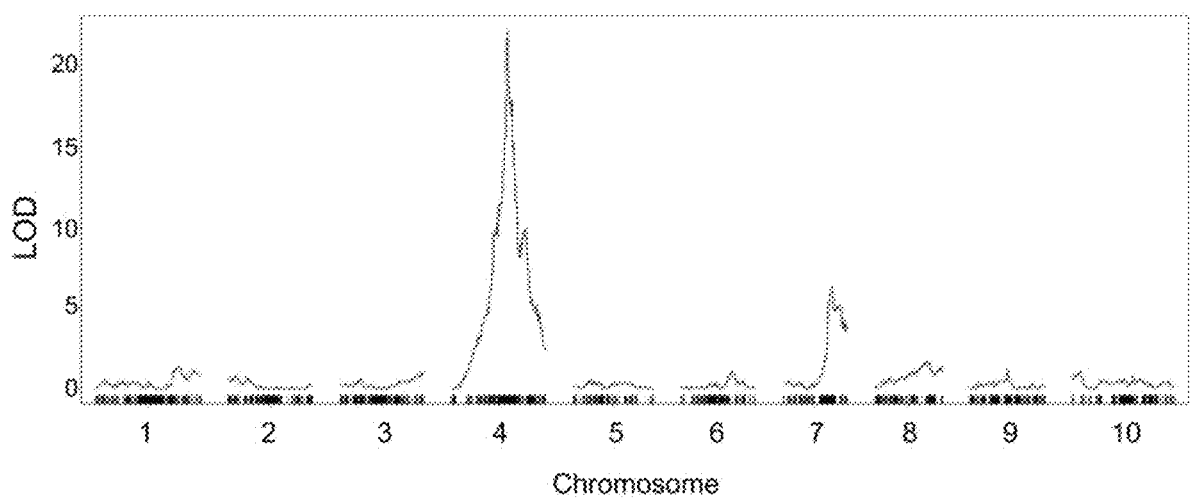
FIG. 1 illustrates LOD scores from Total Varin F2 QTL mapping (x-axis: positions on the Abacus reference genome version CsaAba2; chromosome 10 is the X chromosome).

These and other features of the present teachings will become more apparent from the description herein. While the present teachings are described in conjunction with various embodiments, it is not intended that the present teachings be limited to such embodiments. On the contrary, the present teachings encompass various alternatives, modifications, and equivalents, as will be appreciated by those of skill in the art.

The present teachings relate generally to methods of producing *Cannabis* varieties having modified varin activity, including high THCV concentrations.

The terminology used in the disclosure herein is for the purpose of describing particular embodiments only and is not intended to limit the disclosure. As used in the description of the embodiments of the disclosure and the appended claims, the singular forms "a", "an" and "the" are intended to include the plural forms as well, unless the context clearly indicates otherwise. Also, as used herein, "and/or" refers to and encompasses any and all possible combinations of one or more of the associated listed items. Furthermore, the term "about," as used herein when referring to a measurable value such as an amount of a compound, amount, dose, time, temperature, for example, is meant to encompass variations of 20%, 10%, 5%, 1%, 0.5%, or even 0.1% of the specified amount. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Unless otherwise defined, all terms, including technical and scientific terms used in the description, have the same meaning as commonly understood by one of ordinary skill in the art to which this disclosure belongs.

Definitions

The term "Abacus" or the phrase "Abacus *Cannabis* reference genome" as used herein refers to the *Cannabis* reference genome known as the Abacus reference genome (version CsaAba2).

The term "acidic cannabinoid" refers to a cannabinoid having one or more carboxylic acid functional groups. Examples of acidic cannabinoids include, but are not limited to, tetrahydrocannabinolic acid (THCA), cannabidiolic acid (CBDA), tetrahydrocannabivarinic acid (TCHVA), and cannabichromenic acid (CBC). Acidic cannabinoids are frequently the predominant cannabinoids found in raw (i.e., unprocessed) *Cannabis* plant material.

The term "alternative nucleotide call" is a nucleotide polymorphism relative to a reference nucleotide for a SNP marker that is significantly associated with the causative SNP(s) that confer(s) a desired phenotype.

The term "backcrossing" or "to backcross" refers to the crossing of an F1 hybrid with one of the original parents. A backcross is used to maintain the identity of one parent (species) and to incorporate a particular trait from a second parent (species). The best strategy is to cross the F1 hybrid back to the parent possessing the most desirable traits. Two or more generations of backcrossing may be necessary, but this is practical only if the desired characteristic or trait is present in the F1.

The term "beneficial" as used herein refers to an allele conferring a modified varin activity phenotype.

The term "CBDV" means cannabidivarin.

The term "CBDVA" means cannabidivarinic acid.

The term "CBGV" means cannabigerivarin.

The term "CBGVA" means cannabigerivarinic acid.

The term "*Cannabis*" refers to plants of the genus *Cannabis*, including *Cannabis sativa*, and subspecies, *Cannabis sativa* indica, and *Cannabis sativa ruderalis*. Hemp is a type of *Cannabis* having low levels of tetrahydrocannabinol.

The term "cell" refers to a prokaryotic or eukaryotic cell, including plant cells, capable of replicating DNA, transcribing RNA, translating polypeptides, and secreting proteins.

The term "coding sequence" refers to a DNA sequence which codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences.

The terms "construct," "plasmid," "vector," and "cassette" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. The term "recombinant DNA construct" or "recombinant expression construct" is used interchangeably and refers to a discrete polynucleotide into which a nucleic acid sequence or fragment can be moved. Preferably, it is a plasmid vector or a fragment thereof comprising the promoters of the present invention. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., EMBO J. 4:2411-2418 (1985); De Almeida et al., Mol. Gen. Genetics 218:78-86 (1989)), and thus that multiple events must be screened in order to obtain lines displaying the desired expression level and pattern. Such screening may be accomplished by PCR and Southern analysis of DNA, RT-PCR and Northern analysis of mRNA expression, Western analysis of protein expression, or phenotypic analysis.

The term "cross", "crossing", "cross pollination" or "cross-breeding" refer to the process by which the pollen of one flower on one plant is applied (artificially or naturally) to the ovule (stigma) of a flower on another plant. Backcrossing is a process in which a breeder repeatedly crosses hybrid progeny, for example a first generation hybrid (F1), back to one of the parents of the hybrid progeny. Backcrossing can be used to introduce one or more single locus conversions from one genetic background into another.

The term "cultivar" means a group of similar plants that by structural features and performance (e.g., morphological and physiological characteristics) can be identified from other varieties within the same species. Furthermore, the term "cultivar" variously refers to a variety, strain or race of plant that has been produced by horticultural or agronomic techniques and is not normally found in wild populations. The terms cultivar, variety, strain, plant and race are often used interchangeably by plant breeders, agronomists and farmers.

The term "detect" or "detecting" refers to any of a variety of methods for determining the presence of a nucleic acid.

The term "donor plants" refers to the parents of a variety which contains the gene or trait of interest which is desired to be introduced into a second variety (e.g., "recipient plants").

The term "expression" or "gene expression" relates to the process by which the coded information of a nucleic acid transcriptional unit (including, e.g., genomic DNA) is converted into an operational, non-operational, or structural part of a cell, often including the synthesis of a protein. Gene expression can be influenced by external signals; for example, exposure of a cell, tissue, or organism to an agent that increases or decreases gene expression. Expression of a gene can also be regulated anywhere in the pathway from DNA to RNA to protein. Regulation of gene expression occurs, for example, through controls acting on transcription, translation, RNA transport and processing, degradation of intermediary molecules such as mRNA, or through activation, inactivation, compartmentalization, or degradation of specific protein molecules after they have been made, or by combinations thereof. Gene expression can be measured at the RNA level or the protein level by any method known in the art, including, without limitation, Northern blot, RT-PCR, Western blot, or in vitro, in situ, or in vivo protein activity assay(s). Elevated levels refers to higher than average levels of gene expression in comparison to a reference genome, e.g., the Abacus reference genome.

The term "functional" as used herein refers to DNA or amino acid sequences which are of sufficient size and sequence to have the desired function (i.e. the ability to cause expression of a gene resulting in gene activity expected of the gene found in a reference genome, e.g., the Abacus reference genome.)

The term "gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" or "recombinant expression construct", which are used interchangeably, refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

The term "genetic modification" or "genetic alteration" as used herein refers to a change from the wild-type or reference sequence of one or more nucleic acid molecules. Genetic modifications or alterations include without limitation, base pair substitutions, additions and deletions of at least one nucleotide from a nucleic acid molecule of known sequence. One type of gene modification may be gene silencing, which is a reduction or complete absence of gene expression.

The term "genome" as it applies to plant cells encompasses not only chromosomal DNA found within the nucleus, but organelle DNA found within subcellular components (e.g., mitochondrial, plastid) of the cell.

The term "genotype" refers to the genetic makeup of an individual cell, cell culture, tissue, organism (e.g., a plant), or group of organisms.

The term "germplasm" refers to genetic material of or from an individual (e.g., a plant), a group of individuals (e.g., a plant line, variety, or family), or a clone derived from a line, variety, species, or culture. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants can be grown, as well as plant parts, such as leaves, stems, pollen, or cells that can be cultured into a whole plant.

The term "haplotype" refers to the genotype of a plant at a plurality of genetic loci, e.g., a combination of alleles or markers. Haplotype can refer to sequence polymorphisms at a particular locus, such as a single marker locus, or sequence polymorphisms at multiple loci along a chromosomal segment in a given genome. As used herein, a haplotype can be a nucleic acid region spanning two markers.

A plant is "homozygous" if the individual has only one type of allele at a given locus (e.g., a diploid individual has a copy of the same allele at a locus for each of two homologous chromosomes). An individual is "heterozygous" if more than one allele type is present at a given locus (e.g., a diploid individual with one copy each of two different alleles). The term "homogeneity" indicates that members of a group have the same genotype at one or more specific loci. In contrast, the term "heterogeneity" is used to indicate that individuals within the group differ in genotype at one or more specific loci.

The terms "hybridizing specifically to," "specific hybridization," and "selectively hybridize to" as used herein refer to the binding, duplexing, or hybridizing of a nucleic acid molecule preferentially to a particular nucleotide sequence under stringent conditions. The term "stringent conditions" refers to conditions under which a probe will hybridize preferentially to its target subsequence, and to a lesser extent to, or not at all to, other sequences. A "stringent hybridization" and "stringent hybridization wash conditions" in the context of nucleic acid hybridization (e.g., as in array, Southern or Northern hybridizations) are sequence dependent, and are different under different environmental parameters. An extensive guide to the hybridization of nucleic acids is found in, e.g., Tijssen (1993) Laboratory Techniques in Biochemistry and Molecular Biology—Hybridization with Nucleic Acid Probes part I, Ch. 2, "Overview of principles of hybridization and the strategy of nucleic acid probe assays," Elsevier, N.Y. ("Tijssen"). Generally, highly stringent hybridization and wash conditions are selected to be about 5.degree. C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on an array or on a filter in a Southern or northern blot is 42.degree. C. using standard hybridization solutions (see, e.g., Sambrook and Russell (2001) Molecular Cloning: A Laboratory Manual (3rd ed.) Vol. 1-3, Cold Spring Harbor Laboratory, Cold Spring Harbor Press, NY, and detailed discussion, below).

The term "hybrid" refers to a variety or cultivar that is the result of a cross of plants of two different varieties. "F1 hybrid" refers to the first generation hybrid, "F2 hybrid" the second generation hybrid, "F3 hybrid" the third generation, and so on. A hybrid refers to any progeny that is either produced or developed.

As used herein, the term "inbreeding" refers to the production of offspring via the mating between relatives. The plants resulting from the inbreeding process are referred to herein as "inbred plants" or "inbreds."

The term "isolated" as used herein means having been removed from its natural environment, or removed from other compounds present when the compound is first formed. The term "isolated" embraces materials isolated from natural sources as well as materials (e.g., nucleic acids and proteins) recovered after preparation by recombinant expression in a host cell, or chemically-synthesized compounds such as nucleic acid molecules, proteins, and peptides.

The terms "initiate transcription," "initiate expression," "drive transcription," and "drive expression" are used interchangeably herein and all refer to the primary function of a promoter. As detailed throughout this disclosure, a promoter is a non-coding genomic DNA sequence, usually upstream (5') to the relevant coding sequence, and its primary function is to act as a binding site for RNA polymerase and initiate transcription by the RNA polymerase. Additionally, there is "expression" of RNA, including functional RNA, or the expression of polypeptide for operably linked encoding nucleotide sequences, as the transcribed RNA ultimately is translated into the corresponding polypeptide.

The term "introduced" refers to a nucleic acid (e.g., expression construct) or protein into a cell. Introduced includes reference to the incorporation of a nucleic acid into a eukaryotic or prokaryotic cell where the nucleic acid may be incorporated into the genome of the cell, and includes reference to the transient provision of a nucleic acid or protein to the cell. Introduced includes reference to stable or transient transformation methods, as well as sexually crossing. Thus, "introduced" in the context of inserting a nucleic acid fragment (e.g., a recombinant DNA construct/expression construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

The term "intron" refers to an intervening sequence in a gene that is transcribed into RNA but is then excised in the process of generating the mature mRNA. The term is also used for the excised RNA sequences. An "exon" is a portion of the sequence of a gene that is transcribed and is found in the mature messenger RNA derived from the gene, but is not necessarily a part of the sequence that encodes the final gene product.

The term "isolated" as used herein means having been removed from its natural environment, or removed from other compounds present when the compound is first formed. The term "isolated" embraces materials isolated from natural sources as well as materials (e.g., nucleic acids and proteins) recovered after preparation by recombinant expression in a host cell, or chemically-synthesized compounds such as nucleic acid molecules, proteins, and peptides.

The term "line" is used broadly to include, but is not limited to, a group of plants vegetatively propagated from a single parent plant, via tissue culture techniques or a group of inbred plants which are genetically very similar due to descent from a common parent(s). A plant is said to "belong" to a particular line if it (a) is a primary transformant (TO) plant regenerated from material of that line; (b) has a pedigree comprised of a TO plant of that line; or (c) is genetically very similar due to common ancestry (e.g., via inbreeding or selfing). In this context, the term "pedigree" denotes the lineage of a plant, e.g. in terms of the sexual crosses affected such that a gene or a combination of genes, in heterozygous (hemizygous) or homozygous condition, imparts a desired trait to the plant.

The term "KR/FABG/FabG1" or "KR/FABG/FabG1 gene" or "KR/FABG/FabG1 protein" refers to Cannabis gene/gene product/protein known as β ketoacyl-acyl carrier protein (ACP) reductase, At1g24360, or 3-oxoacyl-[acyl-carrier-protein] reductase.

The term "marker," "genetic marker," "molecular marker," "marker nucleic acid," and "marker locus" refer to a nucleotide sequence or encoded product thereof (e.g., a protein) used as a point of reference when identifying a linked locus. A marker can be derived from genomic nucleotide sequence or from expressed nucleotide sequences (e.g., from a spliced RNA, a cDNA, etc.), or from an encoded polypeptide, and can be represented by one or more particular variant sequences, or by a consensus sequence. In another sense, a marker is an isolated variant or consensus of such a sequence. The term also refers to nucleic acid sequences complementary to or flanking the marker sequences, such as nucleic acids used as probes or primer pairs capable of amplifying the marker sequence. A "marker probe" is a nucleic acid sequence or molecule that can be used to identify the presence of a marker locus, e.g., a nucleic acid probe that is complementary to a marker locus sequence. Alternatively, in some aspects, a marker probe refers to a probe of any type that is able to distinguish (i.e., genotype) the particular allele that is present at a marker locus. A "marker locus" is a locus that can be used to track the presence of a second linked locus, e.g., a linked locus that encodes or contributes to expression of a phenotypic trait. For example, a marker locus can be used to monitor segregation of alleles at a locus, such as a QTL, that are genetically or physically linked to the marker locus. Thus, a "marker allele," alternatively an "allele of a marker locus" is one of a plurality of polymorphic nucleotide sequences found at a marker locus in a population that is polymorphic for the marker locus. Other examples of such markers are restriction fragment length polymorphism (RFLP) markers, amplified fragment length polymorphism (AFLP) markers, single nucleotide polymorphisms (SNPs), microsatellite markers (e.g. SSRs), sequence-characterized amplified region (SCAR) markers, cleaved amplified polymorphic sequence (CAPS) markers or isozyme markers or combinations of the markers described herein which defines a specific genetic and chromosomal location.

The term "marker assisted selection" refers to the diagnostic process of identifying, optionally followed by selecting a plant from a group of plants using the presence of a molecular marker as the diagnostic characteristic or selection criterion. The process usually involves detecting the presence of a certain nucleic acid sequence or polymorphism in the genome of a plant.

The phrase "modified activity" or "modified expression" or "altered activity" or "altering expression" refers to the production of gene product(s) in organisms in amounts or proportions that differ from the amount of the gene product(s) produced by the corresponding wild-type organisms (i.e., expression is increased or decreased). The modified expression or activity can result in increases or decreases in amounts or levels of different compounds, including cannabinoids such as TCHV or CBDV.

The term "neutral cannabinoid" refers to a cannabinoid without carboxylic acid functional groups. Examples of neutral cannabinoids include, but are not limited to, THC, THCV, CBD, CBG, CBC, and CBN.

The term "offspring" refers to any plant resulting as progeny from a vegetative or sexual reproduction from one or more parent plants or descendants thereof. For instance an offspring plant may be obtained by cloning or selfing of a parent plant or by crossing two parent plants and includes selfings as well as the F1 or F2 or still further generations. An F1 is a first-generation offspring produced from parents at least one of which is used for the first time as donor of a trait, while offspring of second generation (F2) or subsequent generations (F3, F4, etc.) are specimens produced from selfings of F1's, F2's etc. An F1 may thus be (and usually is) a hybrid resulting from a cross between two true breeding parents (true-breeding is homozygous for a trait), while an F2 may be (and usually is) an offspring resulting from self-pollination of said F1 hybrids.

The term "oligonucleotide probe" refers to any kind of nucleotide molecule synthesized to match (i.e., be complementary to) a nucleotide sequence of interest which can be used to detect, analyse, and/or visualize said nucleotide sequence on a molecular level. An oligonucleotide probe according to the present disclosure generally refers to a molecule comprising several nucleotides, in general at least 10, 15, and even at least 20 nucleotides, for example, and having at least one label. Optionally, the oligonucleotide probe may also comprise any suitable non-nucleotide units and/or linking reagent which may be suitable to incorporate the label. It should be understood that the oligonucleotide probe has a length suitable to provide the required specificity. In general, the probe may be a DNA oligonucleotide probe or a RNA oligonucleotide probe. Further, it should also be understood that a nucleotide includes all kind of structures composed of a nucleobase (i.e. a nitrogenous base), a five carbon sugar which may be either a ribose, a 2'-deoxyribose, or any derivative thereof, and a phosphate group. The nucleobase and the sugar constitute a unit referred to as a nucleoside.

The terms "percent sequence identity" or "percent identity" or "identity" are used interchangeably to refer to a sequence comparison based on identical matches between correspondingly identical positions in the sequences being compared between two or more amino acid or nucleotide sequences. The percent identity refers to the extent to which two optimally aligned polynucleotide or peptide sequences are invariant throughout a window of alignment of components, e.g., nucleotides or amino acids. Hybridization experiments and mathematical algorithms known in the art may be used to determine percent identity. Many mathematical algorithms exist as sequence alignment computer programs known in the art that calculate percent identity. These programs may be categorized as either global sequence alignment programs or local sequence alignment programs.

The term "plant" refers to a whole plant and any descendant, cell, tissue, or part of a plant. A class of plant that can be used in the present invention is generally as broad as the class of higher and lower plants amenable to mutagenesis including angiosperms (monocotyledonous and dicotyledonous plants), gymnosperms, ferns and multicellular algae. Thus, "plant" includes dicot and monocot plants. The term "plant parts" include any part(s) of a plant, including, for example and without limitation: seed (including mature seed and immature seed); a plant cutting; a plant cell; a plant cell culture; a plant organ (e.g., pollen, embryos, flowers, fruits, shoots, leaves, roots, stems, and explants). A plant tissue or plant organ may be a seed, protoplast, callus, or any other group of plant cells that is organized into a structural or functional unit. A plant cell or tissue culture may be capable of regenerating a plant having the physiological and morphological characteristics of the plant from which the cell or tissue was obtained, and of regenerating a plant having substantially the same genotype as the plant. In contrast, some plant cells are not capable of being regenerated to produce plants. Regenerable cells in a plant cell or tissue culture may be embryos, protoplasts, meristematic cells, callus, pollen, leaves, anthers, roots, root tips, silk, flowers, kernels, ears, cobs, husks, or stalks. Plant parts include harvestable parts and parts useful for propagation of progeny plants. Plant parts useful for propagation include, for example and without limitation: seed; fruit; a cutting; a seedling; a tuber; and a rootstock. A harvestable part of a plant may be any useful part of a plant, including, for example and without limitation: flower; pollen; seedling; tuber; leaf; stem; fruit; seed; and root. A plant cell is the structural and physiological unit of the plant, comprising a protoplast and a cell wall. A plant cell may be in the form of an isolated single cell, or an aggregate of cells (e.g., a friable callus and a cultured cell), and may be part of a higher organized unit (e.g., a plant tissue, plant organ, and plant). Thus, a plant cell may be a protoplast, a gamete producing cell, or a cell or collection of cells that can regenerate into a whole plant. As such, a seed, which comprises multiple plant cells and is capable of regenerating into a whole plant, is considered a "plant cell" in embodiments herein. In an embodiment described herein are plants in the genus of Cannabis and plants derived thereof, which can be produced asexual or sexual reproduction.

The term "plant part" or "plant tissue" refers to any part of a plant including but not limited to, an embryo, shoot, root, stem, seed, stipule, leaf, petal, flower bud, flower, ovule, bract, trichome, branch, petiole, internode, bark, pubescence, tiller, rhizome, frond, blade, ovule, pollen, stamen. Plant part may also include certain extracts such as kief, oil, or hash which includes Cannabis trichomes or glands.

The terms "polynucleotide," "polynucleotide sequence," "nucleotide," "nucleotide sequence," "nucleic acid sequence," "nucleic acid fragment," and "isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA comprises one or more segments of cDNA, genomic DNA, synthetic DNA, or mixtures thereof. Nucleotides (usually found in their 5'-monophosphate form) are referred to by a single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide. An "isolated polynucleotide" refers to a polymer of ribonucleotides (RNA) or deoxyribonucleotides (DNA) that is single- or double-stranded, optionally containing synthetic, non-natural or altered nucleotide bases. An isolated polynucleotide in the form of DNA may be comprised of one or more segments of cDNA, genomic DNA or synthetic DNA.

The term "polymorphism" refers to a difference in the nucleotide or amino acid sequence of a given region as compared to a nucleotide or amino acid sequence in a homologous-region of another individual, in particular, a difference in the nucleotide of amino acid sequence of a given region which differs between individuals of the same species. A polymorphism is generally defined in relation to a reference sequence. Polymorphisms include single nucleotide differences, differences in sequence of more than one nucleotide, and single or multiple nucleotide insertions, inversions and deletions; as well as single amino acid differences, differences in sequence of more than one amino acid, and single or multiple amino acid insertions, inversions, and deletions.

The term "probe" or "nucleic acid probe," as used herein, is defined to be a collection of one or more nucleic acid fragments whose specific hybridization to a nucleic acid sample comprising a region of interest can be detected. The probe may be unlabeled or labeled as described below so that its binding to the target nucleic acid of interest can be detected. What "probe" refers to specifically is clear from the context in which the word is used. The probe may also be isolated nucleic acids immobilized on a solid surface (e.g., nitrocellulose, glass, quartz, fused silica slides), as in an array. In some embodiments, the probe may be a member of an array of nucleic acids as described, for instance, in WO 96/17958. Techniques capable of producing high density arrays can also be used for this purpose (see, e.g., Fodor (1991) Science 767-773; Johnston (1998) Curr. Biol. 8: R171-R174; Schummer (1997) Biotechniques 23: 1087-1092; Kern (1997) Biotechniques 23: 120-124; U.S. Pat. No. 5,143,854). One of skill will recognize that the precise sequence of the particular probes described herein can be modified to a certain degree to produce probes that are "substantially identical" to the disclosed probes, but retain the ability to specifically bind to (i.e., hybridize specifically to) the same targets or samples as the probe from which they were derived (see discussion above). Such modifications are specifically covered by reference to the individual probes described herein.

The term "progeny" refers to any subsequent generation of a plant. Progeny is measured using the following nomenclature: F1 refers to the first generation progeny, F2 refers to the second generation progeny, F3 refers to the third generation progeny, and so on.

The term "promoter" refers to a nucleic acid fragment capable of controlling transcription of another nucleic acid fragment. A promoter is capable of controlling the expression of a coding sequence or functional RNA. Functional RNA includes, but is not limited to, transfer RNA (tRNA) and ribosomal RNA (rRNA). The promoter sequence consists of proximal and more distal upstream elements, the latter elements often referred to as enhancers. Accordingly, an "enhancer" is a DNA sequence that can stimulate promoter activity, and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. New promoters of various types useful in plant cells are constantly being discovered; numerous examples may be found in the compilation by Okamuro and Goldberg (Biochemistry of Plants 15:1-82 (1989)). It is further recognized that since in most cases the exact boundaries of regulatory sequences have not been completely defined, DNA fragments of some variation may have identical promoter activity.

The terms "PCR" or "Polymerase Chain Reaction" refers to a technique for the synthesis of large quantities of specific DNA segments, consisting of a series of repetitive cycles (Perkin Elmer Cetus Instruments, Norwalk, Conn.). Typically, the double stranded DNA is heat denatured, the two primers complementary to the 3' boundaries of the target segment are annealed at low temperature and then extended at an intermediate temperature. One set of these three consecutive steps comprises a cycle.

The term "protein" refers to amino acid polymers that contain at least five constituent amino acids that are covalently joined by peptide bonds. The constituent amino acids can be from the group of amino acids that are encoded by the genetic code, which include: alanine, valine, leucine, isoleucine, methionine, phenylalanine, tyrosine, tryptophan, serine, threonine, asparagine, glutamine, cysteine, glycine, proline, arginine, histidine, lysine, aspartic acid, and glutamic acid. As used herein, the term "protein" is synonymous with the related terms "peptide" and "polypeptide."

The term "quantitative trait loci" or "QTL" refers to the genetic elements controlling a quantitative trait.

The term "reference plant" or "reference genome" refers to a wild-type or reference sequence that SNPs or other markers in a test sample can be compared to in order to detect a modification of the sequence in the test sample.

The terms "similar," "substantially similar" and "corresponding substantially" as used herein refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences. A "substantially homologous sequence" refers to variants of the disclosed sequences such as those that result from site-directed mutagenesis, as well as synthetically derived sequences. A substantially homologous sequence of the present invention also refers to those fragments of a particular promoter nucleotide sequence disclosed herein that operate to promote the constitutive expression of an operably linked heterologous nucleic acid fragment. These promoter fragments will comprise at least about 20 contiguous nucleotides, preferably at least about 50 contiguous nucleotides, more preferably at least about 75 contiguous nucleotides, even more preferably at least about 100 contiguous nucleotides of the particular promoter nucleotide sequence disclosed herein. The nucleotides of such fragments will usually comprise the TATA recognition sequence of the particular promoter sequence. Such fragments may be obtained by use of restriction enzymes to cleave the naturally occurring promoter nucleotide sequences disclosed herein; by synthesizing a nucleotide sequence from the naturally occurring promoter DNA sequence; or may be obtained through the use of PCR technology. See particularly, Mullis et al., Methods Enzymol. 155:335-350 (1987), and Higuchi, R. In PCR Technology: Principles and Applications for DNA Amplifications; Erlich, H. A., Ed.; Stockton Press Inc.: New York, 1989. Again, variants of these promoter fragments, such as those resulting from site-directed mutagenesis, are encompassed by the compositions of the present invention.

The term "target region" or "nucleic acid target" refers to a nucleotide sequence that resides at a specific chromosomal location. The "target region" or "nucleic acid target" is specifically recognized by a probe.

The term "transition" as used herein refers to the transition of a nucleotide at any specific genomic position with that of a different nucleotide.

The term "transgenic" refers to any cell, cell line, callus, tissue, plant part or plant, the genome of which has been altered by the presence of a heterologous nucleic acid, such as a recombinant DNA construct, including those initial transgenic events as well as those created by sexual crosses or asexual propagation from the initial transgenic event. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation. The term "transgenic plant" refers to a plant which comprises within its genome a heterologous polynucleotide. For example, the heterologous polynucleotide is stably integrated within the genome such that the polynucleotide is passed on to successive generations. The heterologous polynucleotide may be integrated into the genome alone or as part of a recombinant DNA construct.

The term "transformant" refers to a cell, tissue or organism that has undergone transformation. The original transformant is designated as "TO" or "T0." Selfing the T0 produces a first transformed generation designated as "T1" or "T1."

The term "transformation" refers to the transfer of nucleic acid (i.e., a nucleotide polymer) into a cell. As used herein, the term "genetic transformation" refers to the transfer and incorporation of DNA, especially recombinant DNA, into a cell.

The term "transition" as used herein refers to the transition of a nucleotide at any specific genomic position with that of a different nucleotide.

The term "THCV" means tetrahydrocannabivarin.

The term "THCVA" mean tetrahydrocannabivarinic acid.

The term "variety" as used herein has identical meaning to the corresponding definition in the International Convention for the Protection of New Varieties of Plants (UPOV treaty), of Dec. 2, 1961, as Revised at Geneva on Nov. 10, 1972, on Oct. 23, 1978, and on Mar. 19, 1991. Thus, "variety" means a plant grouping within a single botanical taxon of the lowest known rank, which grouping, irrespective of whether the conditions for the grant of a breeder's right are fully met, can be i) defined by the expression of the characteristics resulting from a given genotype or combination of genotypes, ii) distinguished from any other plant grouping by the expression of at least one of the said characteristics and iii) considered as a unit with regard to its suitability for being propagated unchanged.

Cannabis

Cannabis has long been used for drug and industrial purposes, fiber (hemp), for seed and seed oils, for medicinal purposes, and for recreational purposes. Industrial hemp products are made from Cannabis plants selected to produce an abundance of fiber. Some Cannabis varieties have been bred to produce minimal levels of THC, the principal psychoactive constituent responsible for the psychoactivity associated with marijuana. Marijuana has historically consisted of the dried flowers of Cannabis plants selectively bred to produce high levels of THC and other psychoactive cannabinoids. Various extracts including hashish and hash oil are also produced from the plant.

*Cannabis* is an annual, dioecious, flowering herb. The leaves are palmately compound or digitate, with serrate leaflets. *Cannabis* normally has imperfect flowers, with staminate "male" and pistillate "female" flowers occurring on separate plants. It is not unusual, however, for individual plants to separately bear both male and female flowers (i.e., have monoecious plants). Although monoecious plants are often referred to as "hermaphrodites," true hermaphrodites (which are less common in *Cannabis*) bear staminate and pistillate structures on individual flowers, whereas monoecious plants bear male and female flowers at different locations on the same plant.

The life cycle of *Cannabis* varies with each variety but can be generally summarized into germination, vegetative growth, and reproductive stages. Because of heavy breeding and selection by humans, most *Cannabis* seeds have lost dormancy mechanisms and do not require any pre-treatments or winterization to induce germination (See Clarke, R C et al. "*Cannabis*: Evolution and Ethnobotany" University of California Press 2013). Seeds placed in viable growth conditions are expected to germinate in about 3 to 7 days. The first true leaves of a *Cannabis* plant contain a single leaflet, with subsequent leaves developing in opposite formation with increasing number of leaflets. Leaflets can be narrow or broad depending on the morphology of the plant grown. *Cannabis* plants are normally allowed to grow vegetatively for the first 4 to 8 weeks. During this period, the plant responds to increasing light with faster and faster growth. Under ideal conditions, *Cannabis* plants can grow up to 2.5 inches a day, and are capable of reaching heights of up to 20 feet. Indoor growth pruning techniques tend to limit *Cannabis* size through careful pruning of apical or side shoots.

*Cannabis* is diploid, having a chromosome complement of 2n=20, although polyploid individuals have been artificially produced. The first genome sequence of *Cannabis*, which is estimated to be 820 Mb in size, was published in 2011 by a team of Canadian scientists (Bakel et al, "The draft genome and transcriptome of *Cannabis sativa*" Genome Biology 12:R102).

All known varieties of *Cannabis* are wind-pollinated and the fruit is an achene. Most varieties of *Cannabis* are short day plants, with the possible exception of *C. sativa* subsp. *sativa* var. *spontanea* (=*C. ruderalis*), which is commonly described as "auto-flowering" and may be day-neutral.

The genus *Cannabis* was formerly placed in the Nettle (Urticaceae) or Mulberry (Moraceae) family, and later, along with the *Humulus* genus (hops), in a separate family, the Hemp family (Cannabaceae sensu stricto). Recent phylogenetic studies based on cpDNA restriction site analysis and gene sequencing strongly suggest that the Cannabaceae sensu stricto arose from within the former Celtidaceae family, and that the two families should be merged to form a single monophyletic family, the Cannabaceae sensu lato.

*Cannabis* plants produce a unique family of terpenophenolic compounds called cannabinoids. Cannabinoids, terpenoids, and other compounds are secreted by glandular trichomes that occur most abundantly on the floral calyxes and bracts of female plants. As a drug it usually comes in the form of dried flower buds (marijuana), resin (hashish), or various extracts collectively known as hashish oil. There are at least 483 identifiable chemical constituents known to exist in the *Cannabis* plant (Rudolf Brenneisen, 2007, Chemistry and Analysis of Phytocannabinoids (cannabinoids produced by *Cannabis*) and other *Cannabis* Constituents, In Marijuana and the Cannabinoids, ElSohly, ed.; incorporated herein by reference) and at least 85 different cannabinoids have been isolated from the plant (El-Alfy, Abir T, et al., 2010, "Antidepressant-like effect of delta-9-tetrahydrocannabinol and other cannabinoids isolated from *Cannabis sativa* L", Pharmacology Biochemistry and Behavior 95 (4): 434-42; incorporated herein by reference). The two cannabinoids usually produced in greatest abundance are cannabidiol (CBD) and/or $\Delta$9-tetrahydrocannabinol (THC). THC is psychoactive while CBD is not. See, ElSohly, ed. (Marijuana and the Cannabinoids, Humana Press Inc., 321 papers, 2007), which is incorporated herein by reference in its entirety, for a detailed description and literature review on the cannabinoids found in marijuana.

Cannabinoids are the most studied group of secondary metabolites in *Cannabis*. Most exist in two forms, as acids and in neutral (decarboxylated) forms. The acid form is designated by an "A" at the end of its acronym (i.e. THCA). The phytocannabinoids are synthesized in the plant as acid forms, and while some decarboxylation does occur in the plant, it increases significantly post-harvest and the kinetics increase at high temperatures. (Sanchez and Verpoorte 2008). The biologically active forms for human consumption are the neutral forms. Decarboxylation is usually achieved by thorough drying of the plant material followed by heating it, often by either combustion, vaporization, or heating or baking in an oven. Unless otherwise noted, references to cannabinoids in a plant include both the acidic and decarboxylated versions (e.g., CBD and CBDA).

Detection of neutral and acidic forms of cannabinoids are dependent on the detection method utilized. Two popular detection methods are high-performance liquid chromatography (HPLC) and gas chromatography (GC). HPLC separates, identifies, and quantifies different components in a mixture, and passes a pressurized liquid solvent containing the sample mixture through a column filled with a solid adsorbent material. Each molecular component in a sample mixture interacts differentially with the adsorbent material, thus causing different flow rates for the different components and therefore leading to separation of the components. In contrast, GC separates components of a sample through vaporization. The vaporization required for such separation occurs at high temperature. Thus, the main difference between GC and HPLC is that GC involves thermal stress and mainly resolves analytes by boiling points while HPLC does not involve heat and mainly resolves analytes by polarity. The consequence of utilizing different methods for cannabinoid detection therefore is that HPLC is more likely to detect acidic cannabinoid precursors, whereas GC is more likely to detect decarboxylated neutral cannabinoids.

The cannabinoids in *Cannabis* plants include, but are not limited to, $\Delta$9-Tetrahydrocannabinol ($\Delta$9-THC), $\Delta$8-Tetrahydrocannabinol ($\Delta$8-THC), Cannabichromene (CBC), Cannabicyclol (CBL), Cannabidiol (CBD), Cannabielsoin (CBE), Cannabigerol (CBG), Cannabinidiol (CBND), Cannabinol (CBN), Cannabitriol (CBT), and their propyl homologs, including, but are not limited to cannabidivarin (CBDV), $\Delta$9-Tetrahydrocannabivarin (THCV), cannabichromevarin (CBCV), and cannabigerovarin (CBGV). See Holley et al. (Constituents of *Cannabis sativa* L. XI Cannabidiol and cannabichromene in samples of known geographical origin, J. Pharm. Sci. 64:892-894, 1975) and De Zeeuw et al. (Cannabinoids with a propyl side chain in *Cannabis*, Occurrence and chromatographic behavior, Science 175:778-779), each of which is herein incorporated by reference in its entirety for all purposes. Non-THC cannabinoids can be collectively referred to as "CBs", wherein CBs can be one of THCV, CBDV, CBGV, CBCV, CBD, CBC, CBE, CBG, CBN, CBND, and CBT cannabinoids.

Varin Markers and Haplotypes

Varins are a type of cannabinoid compounds having three carbon atoms in their alkyl side chain instead of the five carbon atom alkyl side chains more commonly associated with cannabinoids. Two such varins are tetrahydrocannabivarin (THCV) and cannabidivarin (CBDV), which are homologues of tetrahydrocannabinol (THC) and cannabidiol (CBD), respectively.

The present invention describes the discovery of novel markers indicating modified varin activity for plants, including *Cannabis*. Thus, the markers described herein allow for screening of plants exhibiting modified varin activity. Accordingly, the present invention describes a method for selecting one or more plants having modified varin activity, the method comprising i) obtaining nucleic acids from a sample plant or its germplasm; (ii) detecting one or more markers that indicate modified varin activity, and (iii) indicating modified varin activity. An embodiment further describes selecting the one or more plants indicating modified varin activity. The use of marker-assisted selection in breeding activities is described below.

In an embodiment, the markers described in Table 2 can be used to select one or more plants having modified varin activity. Table 2 describes 242 markers having high significance to plants exhibiting modified varin activity, and lists the marker name, the respective p-value, the respective type indicative of the modified varin activity phenotype (i.e., homozygous for the reference or alternative allele), the reference allele call, and the alternative allele call. In an embodiment, the one or more marker position comprises a polymorphism in the reference allele of the Abacus *Cannabis* reference genome on chromosome 1 relative to position 1,306,106; 1,408,650; 13,708,867; 21,374,553; 33,426,602; 57,945,889; or 74,769,414; or on chromosome 2 relative to position 96,902,576; 5,078,822; 6,291,492; 68,155,237; or 82,116,647; or on chromosome 3 relative to position 601,392; 1,053,571; or 78,793,988; or on chromosome 4 relative to position 72,717,623; 72,413,830; 72,330,901; 73,591,604; 69,742,048; 69,610,062; 76,062,454; 66,562,042; 72,070,492; 74,886,331; 72,386,361; 68,871,783; 72,500,945; 70,313,071; 68,551,901; 42,457,670; 75,695,688; 69,860,635; 65,944,497; 44,409,131; 59,679,717; 74,889,638; 42,260,741; 42,424,601; 42,459,658; 70,616,713; 70,604,032; 26,454,266; 70,623,580; 70,611,260; 62,122,798; 60,918,190; 65,379,561; 39,110,266; 44,819,952; 50,680,227; 44,601,335; 44,623,676; 44,629,900; 44,759,390; 44,867,872; 27,064,107; 44,672,313; 40,776,686; 61,163,234; 43,942,890; 28,202,114; 28,499,186; 28,655,285; 28,563,750; or 72,692,194; 35,933,381; 80,090,345; 80,115,357; 80,199,302; 80,229,056; 80,348,481; 80,353,319; 80,361,168; 80,365,496; 80,429,514; 80,467,768; 80,500,846; 80,554,549; 80,599,233; 79,698,853; 79,824,851; 79,972,170; 80,011,567; 80,012,804; 80,017,161; 80,028,174; 80,051,232; 80,072,595; 80,182,837; 80,299,232; 80,500,846; 80,543,937; or 80,591,401; or on chromosome 5 relative to position 42,019,510; or on chromosome 6 relative to position 1,477,638; 1,547,216; 9,352,336; 21,255,914; 21,288,458; 25,701,639; 46,375,436; 53,088,610; 54,422,975; 56,278,544; 63,262,835; 64,641,858; 82,769,380; 84,428,826; 54,569,276; 78,245,587; 78,551,191; 80,899,443; 83,711,056; or 20,354,173; or on chromosome 7 relative to position 60,682,036; 61,014,416; 60,842,314; 60,836,917; 60,726,211; 60,865,034; 61,689,496; 61,315,097; 61,384,518; 61,543,623; 61,391,296; 11,220,411; 41,986,329; 47,794,758; 58,418,614; 58,467,957; 58,607,780; 58,767,876; 58,788,342; 58,900,646; 58,949,513; 58,995,137; 59,119,856; 59,285,985; 59,294,013; 59,305,086; 59,349,246; 59,400,111; 59,457,070; 59,740,097; 59,769,614; 60,004,461; 60,246,243; 60,300,000; 60,405,904; 60,527,155; 60,730,565; 60,753,532; 60,943,279; 60,976,341; 60,994,423; 61,007,064; 61,258,755; 61,282,508; 61,305,861; 61,328,967; 61,504,547; 61,599,429; 61,645,795; 61,651,527; 61,658,656; 61,715,027; 61,989,002; 61,999,104; 62,019,912; 62,034,938; 62,231,000; 62,387,493; 62,647,527; 62,737,982; 62,742,884; 62,747,249; 62,761,203; 62,767,237; 62,792,364; 62,815,617; 62,850,589; 62,866,162; 62,870,580; 62,941,027; 62,971,551; 62,979,814; 62,993,205; 5,460,790; 27,884,762; 34,997,619; 45,591,259; 52,454,110; 57,247,955; or 58,720,667; or on chromosome 8 relative to position 23,016,846; or on chromosome 9 relative to position 12,654,209; 18,343,719; 27,937,504; 51,967,498; 58,316,394; 1,348,101; 16,113,998; 17,302,948; 17,687,309; 17,980,798; 20,457,181; 28,057,298; 34,290,160; 36,400,585; 45,840,334; 51,591,130; 51,751,347; 52,869,819; 57,745,083; 58,014,320; or 59,868,248; or on chromosome X relative to position 8,651,218; 12,403,249; 54,956,182; 56,498,195; 56,966,336; 66,516,851; 71,142,905; 71,618,503; 73,281,407; 73,399,713; 74,496,234; 74,627,738; 74,636,685; 74,863,601; 75,185,443; 75,920,615; 76,189,966; 78,539,112; 80,362,725; 80,424,310; 80,521,410; 80,551,750; 80,610,117; 81,555,347; or 81,636,223, as described in Table 2

In an embodiment, the markers described in Table 2 can be used to select one or more plants having modified varin activity, the markers described as being position 26 in the 50 nucleotide sequences as described in Table 9. Table 9 assigns sequence identifiers to the markers described in Table 2. The present invention thus describes markers signifying a modified varin activity phenotype wherein the marker comprises a polymorphism at position 26 of any one or more of SEQ ID NOs:1-242, and Table 2 can be used to associate which polymorphisms at position 26 of SEQ ID NOs:1-242 are significantly correlating with a modified varin phenotype. The present invention accordingly provides that the marker comprises a polymorphism at position 26 of any one or more of SEQ ID NO:1; SEQ ID NO:2; SEQ ID NO:3; SEQ ID NO:4; SEQ ID NO:5; SEQ ID NO:6; SEQ ID NO:7; SEQ ID NO:8; SEQ ID NO:9; SEQ ID NO:10; SEQ ID NO:11; SEQ ID NO:12; SEQ ID NO:13; SEQ ID NO:14; SEQ ID NO:15; SEQ ID NO:16; SEQ ID NO:17; SEQ ID NO:18; SEQ ID NO:19; SEQ ID NO:20; SEQ ID NO:21; SEQ ID NO:22; SEQ ID NO:23; SEQ ID NO:24; SEQ ID NO:25; SEQ ID NO:26; SEQ ID NO:27; SEQ ID NO:28; SEQ ID NO:29; SEQ ID NO:30; SEQ ID NO:31; SEQ ID NO:32; SEQ ID NO:33; SEQ ID NO:34; SEQ ID NO:35; SEQ ID NO:36; SEQ ID NO:37; SEQ ID NO:38; SEQ ID NO:39; SEQ ID NO:40; SEQ ID NO:41; SEQ ID NO:42; SEQ ID NO:43; SEQ ID NO:44; SEQ ID NO:45; SEQ ID NO:46; SEQ ID NO:47; SEQ ID NO:48; SEQ ID NO:49; SEQ ID NO:50; SEQ ID NO:51; SEQ ID NO:52; SEQ ID NO:53; SEQ ID NO:54; SEQ ID NO:55; SEQ ID NO:56; SEQ ID NO:57; SEQ ID NO:58; SEQ ID NO:59; SEQ ID NO:60; SEQ ID NO:61; SEQ ID NO:62; SEQ ID NO:63; SEQ ID NO:64; SEQ ID NO:65; SEQ ID NO:66; SEQ ID NO:67; SEQ ID NO:68; SEQ ID NO:69; SEQ ID NO:70; SEQ ID NO:71; SEQ ID NO:72; SEQ ID NO:73; SEQ ID NO:74; SEQ ID NO:75; SEQ ID NO:76; SEQ ID NO:77; SEQ ID NO:78; SEQ ID NO:79; SEQ ID NO:80; SEQ ID NO:81; SEQ ID NO:82; SEQ ID NO:83; SEQ ID NO:84; SEQ ID NO:85; SEQ ID NO:86; SEQ ID NO:87; SEQ ID NO:88;

SEQ ID NO:89; SEQ ID NO:90; SEQ ID NO:91; SEQ ID NO:92; SEQ ID NO:93; SEQ ID NO:94; SEQ ID NO:95; SEQ ID NO:96; SEQ ID NO:97; SEQ ID NO:98; SEQ ID NO:99; SEQ ID NO:100; SEQ ID NO:101; SEQ ID NO:102; SEQ ID NO:103; SEQ ID NO:104; SEQ ID NO:105; SEQ ID NO:106; SEQ ID NO:107; SEQ ID NO:108; SEQ ID NO:109; SEQ ID NO:110; SEQ ID NO:111; SEQ ID NO:112; SEQ ID NO:113; SEQ ID NO:114; SEQ ID NO:115; SEQ ID NO:116; SEQ ID NO:117; SEQ ID NO:118; SEQ ID NO:119; SEQ ID NO:120; SEQ ID NO:121; SEQ ID NO:122; SEQ ID NO:123; SEQ ID NO:124; SEQ ID NO:125; SEQ ID NO:126; SEQ ID NO:127; SEQ ID NO:128; SEQ ID NO:129; SEQ ID NO:130; SEQ ID NO:131; SEQ ID NO:132; SEQ ID NO:133; SEQ ID NO:134; SEQ ID NO:135; SEQ ID NO:136; SEQ ID NO:137; SEQ ID NO:138; SEQ ID NO:139; SEQ ID NO:140; SEQ ID NO:141; SEQ ID NO:142; SEQ ID NO:143; SEQ ID NO:144; SEQ ID NO:145; SEQ ID NO:146; SEQ ID NO:147; SEQ ID NO:148; SEQ ID NO:149; SEQ ID NO:150; SEQ ID NO:151; SEQ ID NO:152; SEQ ID NO:153; SEQ ID NO:154; SEQ ID NO:155; SEQ ID NO:156; SEQ ID NO:157; SEQ ID NO:158; SEQ ID NO:159; SEQ ID NO:160; SEQ ID NO:161; SEQ ID NO:162; SEQ ID NO:163; SEQ ID NO:164; SEQ ID NO:165; SEQ ID NO:166; SEQ ID NO:167; SEQ ID NO:168; SEQ ID NO:169; SEQ ID NO:170; SEQ ID NO:171; SEQ ID NO:172; SEQ ID NO:173; SEQ ID NO:174; SEQ ID NO:175; SEQ ID NO:176; SEQ ID NO:177; SEQ ID NO:178; SEQ ID NO:179; SEQ ID NO:180; SEQ ID NO:181; SEQ ID NO:182; SEQ ID NO:183; SEQ ID NO:184; SEQ ID NO:185; SEQ ID NO:186; SEQ ID NO:187; SEQ ID NO:188; SEQ ID NO:189; SEQ ID NO:190; SEQ ID NO:191; SEQ ID NO:192; SEQ ID NO:193; SEQ ID NO:194; SEQ ID NO:195; SEQ ID NO:196; SEQ ID NO:197; SEQ ID NO:198; SEQ ID NO:199; SEQ ID NO:200; SEQ ID NO:201; SEQ ID NO:202; SEQ ID NO:203; SEQ ID NO:204; SEQ ID NO:205; SEQ ID NO:206; SEQ ID NO:207; SEQ ID NO:208; SEQ ID NO:209; SEQ ID NO:210; SEQ ID NO:211; SEQ ID NO:212; SEQ ID NO:213; SEQ ID NO:214; SEQ ID NO:215; SEQ ID NO:216; SEQ ID NO:217; SEQ ID NO218; SEQ ID NO:219; SEQ ID NO:220; SEQ ID NO:221; SEQ ID NO:222; SEQ ID NO:223; SEQ ID NO:224; SEQ ID NO:225; SEQ ID NO:226; SEQ ID NO:227; SEQ ID NO:228; SEQ ID NO:229; SEQ ID NO:230; SEQ ID NO:231; SEQ ID NO:232; SEQ ID NO:233; SEQ ID NO:234; SEQ ID NO:235; SEQ ID NO:236; SEQ ID NO:237; SEQ ID NO:238; SEQ ID NO:239; SEQ ID NO:240; SEQ ID NO:241; or SEQ ID NO:242.

The present invention further describes the discovery of novel haplotype markers for plants, including *Cannabis*. Haplotypes refer to the genotype of a plant at a plurality of genetic loci, e.g., a combination of alleles or markers. Haplotype can refer to sequence polymorphisms at a particular locus, such as a single marker locus, or sequence polymorphisms at multiple loci along a chromosomal segment in a given genome. Markers of the present invention and within the haplotypes described are significantly correlated to plants having modified varin activity, which thus can be used to screen plants exhibiting modified varin activity. In an embodiment, markers present within the haplotypes described in Table 2 can be used to screen for plants having modified varin activity as Table 2 describes the left and right flanking markers of the haplotype regions, as well as the left and right flanking marker position within the respective chromosome.

Accordingly, as a non-limiting example for illustrative and teaching how to make and use purposes, Table 2 describes the marker identified as 142078_3920202, which is located at position 72,717,623 on chromosome 4 of the Abacus *Cannabis* reference genome (or position 26 of SEQ ID NO:1), as a marker within a haplotype defined as being positioned between markers 142078_3860187 and 142078_3932846, or between positions 69,222,980 and 74,594,736 on chromosome 4 of the Abacus *Cannabis* reference genome. Thus any other marker that exists between markers 142078_3860187 and 142078_3932846, or between positions 56,158,064 and 61,821,470 on chromosome 4 of the Abacus *Cannabis* reference genome is a marker imparting the modified varin activity phenotype, which can be used to select for plants having modified varin activity.

Thus, any marker existing within each haplotype described in Table 2 is a marker imparting the modified varin phenotype, which can be used to select for plants having modified varin activity.

Quantitative Trait Loci

The term chromosome interval designates a contiguous linear span of genomic DNA that resides on a single chromosome. A chromosome interval may comprise a quantitative trait locus ("QTL") linked with a genetic trait and the QTL may comprise a single gene or multiple genes associated with the genetic trait. The boundaries of a chromosome interval comprising a QTL are drawn such that a marker that lies within the chromosome interval can be used as a marker for the genetic trait, as well as markers genetically linked thereto. Each interval comprising a QTL comprises at least one gene conferring a given trait, however knowledge of how many genes are in a particular interval is not necessary to make or practice the invention, as such an interval will segregate at meiosis as a linkage block. In accordance with the invention, a chromosomal interval comprising a QTL may therefore be readily introgressed and tracked in a given genetic background using the methods and compositions provided herein.

Identification of chromosomal intervals and QTL is therefore beneficial for detecting and tracking a genetic trait, such as modified varin activity, in plant populations. In some embodiments, this is accomplished by identification of markers linked to a particular QTL. The principles of QTL analysis and statistical methods for calculating linkage between markers and useful QTL include penalized regression analysis, ridge regression, single point marker analysis, complex pedigree analysis, Bayesian MCMC, identity-by-descent analysis, interval mapping, composite interval mapping (CIM), and Haseman-Elston regression. QTL analyses may be performed with the help of a computer and specialized software available from a variety of public and commercial sources known to those of skill in the art.

Detection of Markers

Marker detection is well known in the art. For example, amplification of a target polynucleotide (e.g., by PCR) using a particular amplification primer pair that permit the primer pair to hybridize to the target polynucleotide to which a primer having the corresponding sequence (or its complement) would bind and preferably to produce an identifiable amplification product (the amplicon) having a marker is well known in the art.

Methods for designing PCR primers and PCR cloning are generally known in the art and are disclosed in Sambrook et al. (1989) Molecular Cloning: A Laboratory Manual (2d ed., Cold Spring Harbor Laboratory Press, Plainview, N.Y.). See also Innis et al., eds. (1990) PCR Protocols: A Guide to Methods and Applications (Academic Press, New York); Innis and Gelfand, eds. (1995) PCR Strategies (Academic Press, New York); and Innis and Gelfand, eds. (1999) PCR Methods Manual (Academic Press, New York). Methods of amplification are further described in U.S. Pat. Nos. 4,683,195, 4,683,202 and Chen et al. (1994) PNAS 91:5695-5699. These methods as well as other methods known in the art of DNA amplification may be used in the practice of the embodiments of the present invention. It will be appreciated that suitable primers to be used with the invention can be designed using any suitable method. It is not intended that the invention be limited to any particular primer or primer pair. It is not intended that the primers of the invention be limited to generating an amplicon of any particular size. For example, the primers used to amplify the marker loci and alleles herein are not limited to amplifying the entire region of the relevant locus. The primers can generate an amplicon of any suitable length that is longer or shorter than those disclosed herein. In some embodiments, marker amplification produces an amplicon at least 20 nucleotides in length, or alternatively, at least 50 nucleotides in length, or alternatively, at least 100 nucleotides in length, or alternatively, at least 200 nucleotides in length. It is understood that a number of parameters in a specific PCR protocol may need to be adjusted to specific laboratory conditions and may be slightly modified and yet allow for the collection of similar results. The primers of the invention may be radiolabeled, or labeled by any suitable means (e.g., using a non-radioactive fluorescent tag), to allow for rapid visualization of the different size amplicons following an amplification reaction without any additional labeling step or visualization step. The known nucleic acid sequences for the genes described herein are sufficient to enable one of skill in the art to routinely select primers for amplification of the gene of interest.

Other suitable amplification methods include, but are not limited to, ligase chain reaction (LCR) (see, Wu and Wallace (1989) Genomics 4: 560, Landegren et al. (1988) Science 241: 1077, and Barringer et al. (1990) Gene 89: 117), transcription amplification (Kwoh et al. (1989) Proc. Natl. Acad. Sci. USA 86: 1173), self-sustained sequence replication (Guatelli et al. (1990) Proc. Natl. Acad. Sci. USA 87: 1874), dot PCR, and linker adapter PCR, etc.

An amplicon is an amplified nucleic acid, e.g., a nucleic acid that is produced by amplifying a template nucleic acid by any available amplification method (e.g., PCR, LCR, transcription, or the like). A genomic nucleic acid is a nucleic acid that corresponds in sequence to a heritable nucleic acid in a cell. Common examples include nuclear genomic DNA and amplicons thereof. A genomic nucleic acid is, in some cases, different from a spliced RNA, or a corresponding cDNA, in that the spliced RNA or cDNA is processed, e.g., by the splicing machinery, to remove introns. Genomic nucleic acids optionally comprise non-transcribed (e.g., chromosome structural sequences, promoter regions, enhancer regions, etc.) and/or non-translated sequences (e.g., introns), whereas spliced RNA/cDNA typically do not have non-transcribed sequences or introns. A template nucleic acid is a nucleic acid that serves as a template in an amplification reaction (e.g., a polymerase based amplification reaction such as PCR, a ligase mediated amplification reaction such as LCR, a transcription reaction, or the like). A template nucleic acid can be genomic in origin, or alternatively, can be derived from expressed sequences, e.g., a cDNA or an EST. Details regarding the use of these and other amplification methods can be found in any of a variety of standard texts. Many available biology texts also have extended discussions regarding PCR and related amplification methods and one of skill will appreciate that essentially any RNA can be converted into a double stranded DNA suitable for restriction digestion, PCR expansion and sequencing using reverse transcriptase and a polymerase.

PCR detection and quantification using dual-labeled fluorogenic oligonucleotide probes, commonly referred to as "TaqMan™" probes, can also be performed according to the present invention. These probes are composed of short (e.g., 20-25 base) oligodeoxynucleotides that are labeled with two different fluorescent dyes. On the 5' terminus of each probe is a reporter dye, and on the 3' terminus of each probe a quenching dye is found. The oligonucleotide probe sequence is complementary to an internal target sequence present in a PCR amplicon. When the probe is intact, energy transfer occurs between the two fluorophores and emission from the reporter is quenched by the quencher by FRET. During the extension phase of PCR, the probe is cleaved by 5' nuclease activity of the polymerase used in the reaction, thereby releasing the reporter from the oligonucleotide-quencher and producing an increase in reporter emission intensity. TaqMan™ probes are oligonucleotides that have a label and a quencher, where the label is released during amplification by the exonuclease action of the polymerase used in amplification, providing a real time measure of amplification during synthesis. A variety of TaqMan™ reagents are commercially available, e.g., from Applied Biosystems as well as from a variety of specialty vendors such as Biosearch Technologies.

In general, synthetic methods for making oligonucleotides, including probes, primers, molecular beacons, PNAs, LNAs (locked nucleic acids), etc., are well known. For example, oligonucleotides can be synthesized chemically according to the solid phase phosphoramidite triester method described. Oligonucleotides, including modified oligonucleotides, can also be ordered from a variety of commercial sources.

Nucleic acid probes to the marker loci can be cloned and/or synthesized. Any suitable label can be used with a probe of the invention. Detectable labels suitable for use with nucleic acid probes include, for example, any composition detectable by spectroscopic, radioisotopic, photochemical, biochemical, immunochemical, electrical, optical or chemical means. Useful labels include biotin for staining with labeled streptavidin conjugate, magnetic beads, fluorescent dyes, radio labels, enzymes, and colorimetric labels. Other labels include ligands which bind to antibodies labeled with fluorophores, chemiluminescent agents, and enzymes. A probe can also constitute radio labeled PCR primers that are used to generate a radio labeled amplicon. It is not intended that the nucleic acid probes of the invention be limited to any particular size.

Amplification is not always a requirement for marker detection (e.g. Southern blotting and RFLP detection). Separate detection probes can also be omitted in amplification/detection methods, e.g., by performing a real time amplification reaction that detects product formation by modification of the relevant amplification primer upon incorporation into a product, incorporation of labeled nucleotides into an amplicon, or by monitoring changes in molecular rotation properties of amplicons as compared to unamplified precursors (e.g., by fluorescence polarization).

Varin Genes

The QLT data as described herein identifies the KR gene (SEQ ID NO: 243 and SEQ ID NO: 244 (protein)) as possibly involved in the production of modified varin activity in *Cannabis*. The KR gene pt/mtKR/FabG1 (β ketoacyl-acyl carrier protein (ACP) reductase, At1g24360) is also referred to as 3-oxoacyl-[acyl-carrier-protein] reductase. KR functions together with enoyl-ACP reductase (pt/mtER) to catalyze two of the reactions that constitute the core four-reaction cycle of the fatty acid biosynthesis (FAS) system, which iteratively elongates the acyl-chain by two carbon atoms per cycle (Guan et al. 2020, Plant Physiology 183(2): 517-529). In *Cannabis*, plastid fatty acid biosynthesis forms the precursor for the acyl chain in THC and THCV (Welling et al. 2019, Scientific Reports 9(1): 1-13). Allelic variation of KR likely produces a KR variant that results in a shorter propyl (3-carbon) side chain found in THCV instead of a pentyl (5-carbon) group found in THC. Guan et al. (2020, Plant Physiology 183(2): 517-529) describe a single copy of KR in *Arabidopsis*, the presence of a pre-sequence determines whether it localizes to the chloroplast, where it is involved in fatty acid chain elongation, or to the mitochondria where it is involved in different processes. A T-DNA insertion in KR in *Arabidopsis* makes it embryonic lethal, further supporting the notion that it is essential for fatty acid biosynthesis. In *Cannabis* there appear to be at least 3 copies of KR with varying expression levels in stalked capitate trichomes between the low Total Varin (0.11%) variety 'Purple Kush' and the intermediate Total Varin variety 'Finola' (0.74%; Livingston et al. 2020, The Plant Journal 101: 37-56). BLASTP results of the mapped 'Abacus' KRsequence on CBDrx reference genome result in: 3-oxoacyl-[acyl-carrier-protein] reductase 4 [*Cannabis sativa*] 100% protein sequence match for full 322 AA sequence. Gene expression analysis of *Cannabis* stalked capitate trichomes identifies 3 KR genes with homologs in *Brassica napus*: fabg1, fabg2, and fabg3. Two of these genes, fabg1 and fabg3 display significant expression differences between 'Finola' and 'Purple Kush' (Livingston et al. 2020, The Plant Journal 101: 37-56). BLASTN of the transcriptome fragments of these three genes identified fabg1 in 'Finola' and 'Purple Kush' as the homolog of the mapped 'Abacus' KRgene.

*Cannabis* Breeding

*Cannabis* is an important and valuable crop. Thus, a continuing goal of *Cannabis* plant breeders is to develop stable, high yielding *Cannabis* cultivars that are agronomically sound. To accomplish this goal, the *Cannabis* breeder preferably selects and develops *Cannabis* plants with traits that result in superior cultivars. The plants described herein can be used to produce new plant varieties. In some embodiments, the plants are used to develop new, unique, and superior varieties or hybrids with desired phenotypes.

The development of commercial *Cannabis* cultivars requires the development of *Cannabis* varieties, the crossing of these varieties, and the evaluation of the crosses. Pedigree breeding and recurrent selection breeding methods may be used to develop cultivars from breeding populations. Breeding programs may combine desirable traits from two or more varieties or various broad-based sources into breeding pools from which cultivars are developed by selfing and selection of desired phenotypes. The new cultivars may be crossed with other varieties and the hybrids from these crosses are evaluated to determine which have commercial potential.

Details of existing *Cannabis* plants varieties and breeding methods are described in Potter et al. (2011, World Wide Weed: Global Trends in *Cannabis* Cultivation and Its Control), Holland (2010, The Pot Book: A Complete Guide to *Cannabis*, Inner Traditions/Bear & Co, ISBN1594778981, 9781594778988), Green I (2009, The *Cannabis* Grow Bible: The Definitive Guide to Growing Marijuana for Recreational and Medical Use, Green Candy Press, 2009, ISBN 1931160589, 9781931160582), Green II (2005, The *Cannabis* Breeder's Bible: The Definitive Guide to Marijuana Genetics, *Cannabis* Botany and Creating Strains for the Seed Market, Green Candy Press, 1931160279, 9781931160278), Starks (1990, Marijuana Chemistry: Genetics, Processing & Potency, ISBN 0914171399, 9780914171393), Clarke (1981, Marijuana Botany, an Advanced Study: The Propagation and Breeding of Distinctive *Cannabis*, Ronin Publishing, ISBN 091417178X, 9780914171782), Short (2004, Cultivating Exceptional *Cannabis*: An Expert Breeder Shares His Secrets, ISBN 1936807122, 9781936807123), Cervantes (2004, Marijuana Horticulture: The Indoor/Outdoor Medical Grower's Bible, Van Patten Publishing, ISBN 187882323X, 9781878823236), Franck et al. (1990, Marijuana Grower's Guide, Red Eye Press, ISBN 0929349016, 9780929349015), Grotenhermen and Russo (2002, *Cannabis* and Cannabinoids: Pharmacology, Toxicology, and Therapeutic Potential, Psychology Press, ISBN 0789015080, 9780789015082), Rosenthal (2007, The Big Book of Buds: More Marijuana Varieties from the World's Great Seed Breeders, ISBN 1936807068, 9781936807062), Clarke, R C (*Cannabis*: Evolution and Ethnobotany 2013 (In press)), King, J (Cannabible Vols 1-3, 2001-2006), and four volumes of Rosenthal's Big Book of Buds series (2001, 2004, 2007, and 2011), each of which is herein incorporated by reference in its entirety for all purposes.

Pedigree selection, where both single plant selection and mass selection practices are employed, may be used for the generating varieties as described herein. Pedigree selection, also known as the "Vilmorin system of selection," is described in Fehr, Walter; Principles of Cultivar Development, Volume I, Macmillan Publishing Co., which is hereby incorporated by reference. Pedigree breeding is used commonly for the improvement of self-pollinating crops or inbred lines of cross-pollinating crops. Two parents which possess favorable, complementary traits are crossed to produce an F1. An F2 population is produced by selfing one or several F1's or by intercrossing two F1's (sib mating). Selection of the best individuals usually begins in the F2 population; then, beginning in the F3, the best individuals in the best families are usually selected. Replicated testing of families, or hybrid combinations involving individuals of these families, often follows in the F4 generation to improve the effectiveness of selection for traits with low heritability. At an advanced stage of inbreeding (e.g., F6 and F7), the best lines or mixtures of phenotypically similar lines are tested for potential release as new cultivars.

Choice of breeding or selection methods depends on the mode of plant reproduction, the heritability of the trait(s) being improved, and the type of cultivar used commercially (e.g., F1 hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

Mass and recurrent selections can be used to improve populations of either self- or cross-pollinating crops. A genetically variable population of heterozygous individuals may be identified or created by intercrossing several different parents. The best plants may be selected based on individual superiority, outstanding progeny, or excellent combining ability. Preferably, the selected plants are intercrossed to produce a new population in which further cycles of selection are continued.

Backcross breeding has been used to transfer genes for a simply inherited, highly heritable trait into a desirable homozygous cultivar or line that is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent may be selected and repeatedly crossed (backcrossed) to the recurrent parent. The resulting plant is expected to have the attributes of the recurrent parent (e.g., cultivar) and the desirable trait transferred from the donor parent.

A single-seed descent procedure refers to planting a segregating population, harvesting a sample of one seed per plant, and using the one-seed sample to plant the next generation. When the population has advanced from the F2 to the desired level of inbreeding, the plants from which lines are derived will each trace to different F2 individuals. The number of plants in a population declines each generation due to failure of some seeds to germinate or some plants to produce at least one seed. As a result, not all of the F2 plants originally sampled in the population will be represented by a progeny when generation advance is completed.

Mutation breeding is another method of introducing new traits into *Cannabis* varieties. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation (such as X-rays, Gamma rays, neutrons, Beta radiation, or ultraviolet radiation), chemical mutagens (such as base analogs like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid or acridines. Once a desired trait is observed through mutagenesis the trait may then be incorporated into existing germplasm by traditional breeding techniques. Details of mutation breeding can be found in Principles of Cultivar Development by Fehr, Macmillan Publishing Company, 1993.

The complexity of inheritance also influences the choice of the breeding method. Backcross breeding may be used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Additional breeding methods have been known to one of ordinary skill in the art, e.g., methods discussed in Chahal and Gosal (Principles and procedures of plant breeding: biotechnological and conventional approaches, CRC Press, 2002, ISBN 084931321X, 9780849313219), Taji et al. (In vitro plant breeding, Routledge, 2002, ISBN 156022908X, 9781560229087), Richards (Plant breeding systems, Taylor & Francis US, 1997, ISBN 0412574500, 9780412574504), Hayes (Methods of Plant Breeding, Publisher: READ BOOKS, 2007, ISBN1406737062, 9781406737066), each of which is incorporated by reference in its entirety for all purposes. *Cannabis* genome has been sequenced (Bakel et al., The draft genome and transcriptome of *Cannabis sativa*, Genome Biology, 12(10):R102, 2011). Molecular markers for *Cannabis* plants are described in Datwyler et al. (Genetic variation in hemp and marijuana (*Cannabis sativa* L.) according to amplified fragment length polymorphisms, J Forensic Sci. 2006 March; 51(2):371-5), Pinarkara et al., (RAPD analysis of seized marijuana (*Cannabis sativa* L.) in Turkey, Electronic Journal of Biotechnology, 12(1), 2009), Hakki et al., (Inter simple sequence repeats separate efficiently hemp from marijuana (*Cannabis sativa* L.), Electronic Journal of Biotechnology, 10(4), 2007), Datwyler et al., (Genetic Variation in Hemp and Marijuana (*Cannabis sativa* L.) According to Amplified Fragment Length Polymorphisms, J Forensic Sci, March 2006, 51(2):371-375), Gilmore et al. (Isolation of microsatellite markers in *Cannabis sativa* L. (marijuana), Molecular Ecology Notes, 3(1): 105-107, March 2003), Pacifico et al., (Genetics and marker-assisted selection of chemotype in *Cannabis sativa* L.), Molecular Breeding (2006) 17:257-268), and Mendoza et al., (Genetic individualization of *Cannabis sativa* by a short tandem repeat multiplex system, Anal Bioanal Chem (2009) 393:719-726), each of which is herein incorporated by reference in its entirety for all purposes.

The production of double haploids can also be used for the development of homozygous varieties in a breeding program. Double haploids are produced by the doubling of a set of chromosomes from a heterozygous plant to produce a completely homozygous individual. For example, see Wan et al., Theor. Appl. Genet., 77:889-892, 1989.

Marker Assisted Selection Breeding

In an embodiment, marker assisted selection (MAS) is used to produce plants with desired traits. MAS is a powerful shortcut to selecting for desired phenotypes and for introgressing desired traits into cultivars (e.g., introgressing desired traits into elite lines). MAS is easily adapted to high throughput molecular analysis methods that can quickly screen large numbers of plant or germplasm genetic material for the markers of interest and is much more cost effective than raising and observing plants for visible traits.

In some embodiments, the invention therefore provides quantitative trait loci (QTL) that demonstrate significant co-segregation with elevated THCV, THCVA, CBDV, CBDVA, CBGV, or CBGVA levels. The QTL of the invention can be tracked during plant breeding or introgressed into a desired genetic background in order to provide novel plants exhibiting elevated THCV, THCVA, CBDV, CBDVA, CBGV, or CBGVA levels and one or more other beneficial traits. Molecular markers linked to the QTL of the invention and methods of using the markers for detection of and selection for elevated THCV, THCVA, CBDV, CBDVA, CBGV, or CBGVA levels can be used. Thus, embodiments of the invention therefore include specific markers, chromosome intervals comprising the markers, and methods of detecting markers genetically linked to elevated THCV, THCVA, CBDV, CBDVA, CBGV, or CBGVA levels. For example, the markers described in Table 2. In an embodiment, the polymorphism can be at position 72,717,623 on chromosome 1 of the Abacus *Cannabis* reference genome (SEQ ID NO:1). Also provided herein are markers that are useful for detecting the presence or absence of THCV, THCVA, CBDV, CBDVA, CBGV, or CBGVA activity alleles within the QTL of the invention that can be used in marker assisted selection (MAS) breeding programs to produce plants with a desired elevated THCV, THCVA, CBDV, CBDVA, CBGV, or CBGVA levels. Also provided herein are markers that are useful for detecting the presence or absence of THCV, THCVA, CBDV, CBDVA, CBGV, or CBGVA activity alleles within the QTL of the invention that can be used in marker assisted selection (MAS) breeding programs to produce plants with a desired level of THCV, THCVA, CBDV, CBDVA, CBGV, or CBGVA.

The invention further provides methods of using the markers identified herein to introgress loci associated with high THCV, THCVA, CBDV, CBDVA, CBGV, or CBGVA levels into plants. Thus, one skilled in the art can use the invention to create novel Cannabis plants with elevated THCV, THCVA, CBDV, CBDVA, CBGV, or CBGVA activity by crossing a donor line comprising a QTL associated with THCV, THCVA, CBDV, CBDVA, CBGV, or CBGVA activity into any desired recipient line, with or without MAS. Resulting progeny can be selected to be genetically similar to the recipient line except for the THCV, THCVA, CBDV, CBDVA, CBGV, or CBGVA activity QTL.

Introgression refers to the transmission of a desired allele of a genetic locus from one genetic background to another, which is significantly assisted through MAS. For example, introgression of a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele can be, e.g., a selected allele of a marker, a QTL, a transgene, or the like.

The introgression of one or more desired loci from a donor line into another is achieved via repeated backcrossing to a recurrent parent accompanied by selection to retain one or more loci from the donor parent. Markers associated with varin activity may be assayed in progeny and those progeny with one or more desired markers are selected for advancement. In another aspect, one or more markers can be assayed in the progeny to select for plants with the genotype of the agronomically elite parent. This invention anticipates that trait introgressed varin modification will require more than one generation, wherein progeny are crossed to the recurrent (agronomically elite) parent or selfed. Selections are made based on the presence of one or more varin markers and can also be made based on the recurrent parent genotype, wherein screening is performed on a genetic marker and/or phenotype basis. In another embodiment, markers of this invention can be used in conjunction with other markers, ideally at least one on each chromosome of the Cannabis genome, to track the modified varin activity phenotypes.

Genetic markers are used to identify plants that contain a desired genotype at one or more loci, and that are expected to transfer the desired genotype, along with a desired phenotype to their progeny. Genetic markers can be used to identify plants containing a desired genotype at one locus, or at several unlinked or linked loci (e.g., a haplotype), and that would be expected to transfer the desired genotype, along with a desired phenotype to their progeny. The present invention provides the means to identify plants that exhibit a modified varin phenotype by identifying plants having varin-specific markers.

In general, MAS uses polymorphic markers that have been identified as having a significant likelihood of co-segregation with a desired trait. Such markers are presumed to map near a gene or genes that give the plant its desired phenotype, and are considered indicators for the desired trait, and are termed QTL markers. Plants are tested for the presence or absence of a desired allele in the QTL marker.

Identification of plants or germplasm that include a marker locus or marker loci linked to a desired trait or traits provides a basis for performing MAS. Plants that comprise favorable markers or favorable alleles are selected for, while plants that comprise markers or alleles that are negatively correlated with the desired trait can be selected against. Desired markers and/or alleles can be introgressed into plants having a desired (e.g., elite or exotic) genetic background to produce an introgressed plant or germplasm having the desired trait. In some aspects, it is contemplated that a plurality of markers for desired traits are sequentially or simultaneously selected and/or introgressed. The combinations of markers that are selected for in a single plant is not limited and can include any combination of markers disclosed herein or any marker linked to the markers disclosed herein, or any markers located within the QTL intervals defined herein.

In some embodiments, a first Cannabis plant or germplasm exhibiting a desired trait (the donor) can be crossed with a second Cannabis plant or germplasm (the recipient, e.g., an elite or exotic Cannabis, depending on characteristics that are desired in the progeny) to create an introgressed Cannabis plant or germplasm as part of a breeding program. In some aspects, the recipient plant can also contain one or more loci associated with one or more desired traits, which can be qualitative or quantitative trait loci. In another aspect, the recipient plant can contain a transgene.

MAS, as described herein, using additional markers flanking either side of the DNA locus provide further efficiency because an unlikely double recombination event would be needed to simultaneously break linkage between the locus and both markers. Moreover, using markers tightly flanking a locus, one skilled in the art of MAS can reduce linkage drag by more accurately selecting individuals that have less of the potentially deleterious donor parent DNA. Any marker linked to or among the chromosome intervals described herein can thus find use within the scope of this invention.

Similarly, by identifying plants lacking a desired marker locus, plants having low varin activity can be identified and eliminated from subsequent crosses. These marker loci can be introgressed into any desired genomic background, germplasm, plant, line, variety, etc., as part of an overall MAS breeding program designed to modify varin activity. The invention also provides chromosome QTL intervals that can be used in MAS to select plants that demonstrate different varin traits. The QTL intervals can also be used to counter-select plants that do not exhibit increased varin activity.

Thus, the invention permits one skilled in the art to detect the presence or absence of varin modification genotypes in the genomes of Cannabis plants as part of a MAS program, as described herein. In one embodiment, a breeder ascertains the genotype at one or more markers for a parent having favorable varin modification activity, which contains a favorable varin modification activity allele, and the genotype at one or more markers for a parent with unfavorable varin modification activity, which lacks the favorable varin modification activity allele. A breeder can then reliably track the inheritance of the varin modification activity alleles through subsequent populations derived from crosses between the two parents by genotyping offspring with the markers used on the parents and comparing the genotypes at those markers with those of the parents. Depending on how tightly linked the marker alleles are with the trait, progeny that share genotypes with the parent having varin modification activity alleles can be reliably predicted to express the desirable phenotype and progeny that share genotypes with the parent having unfavorable varin modification activity alleles can be reliably predicted to express the undesirable phenotype. Thus, the laborious, inefficient, and potentially inaccurate process of manually phenotyping the progeny for varin modification activity traits is avoided.

Closely linked markers flanking the locus of interest that have alleles in linkage disequilibrium with varin modification activity alleles at that locus may be effectively used to select for progeny plants with desirable varin modification activity traits. Thus, the markers described herein, such as those listed in Table 2, as well as other markers genetically linked to the same chromosome interval, may be used to select for *Cannabis* plants with different varin modification activity traits. Often, a haplotype, which is a set of these markers will be used, (e.g., 2 or more, 3 or more, 4 or more, 5 or more) in the flanking regions of the locus. Optionally, as described above, a marker flanking or within the actual locus may also be used. The parents and their progeny may be screened for these sets of markers, and the markers that are polymorphic between the two parents used for selection. In an introgression program, this allows for selection of the gene or locus genotype at the more proximal polymorphic markers and selection for the recurrent parent genotype at the more distal polymorphic markers.

In an embodiment, MAS is used to select one or more *Cannabis* plants comprising varin modification activity, the method comprising: (i) obtaining nucleic acids from the sample *Cannabis* plant or germplasm; (ii) detecting one or more markers that indicate varin modification activity, (iii) indicating varin modification activity, and (iv) selecting the one or more plants indicating the varin modification activity.

A number of SNPs together within a sequence, or across linked sequences, can be used to describe a haplotype for any particular genotype (Ching et al. (2002), BMC Genet. 3:19 pp Gupta et al. 2001, Rafalski (2002b), Plant Science 162:329-333). Haplotypes may in some circumstances be more informative than single SNPs and can be more descriptive of any particular genotype. Haplotypes of the present invention as described in Table 2 can be used for marker assisted selection.

The choice of markers actually used to practice the invention is not limited and can be any marker that is genetically linked to the intervals as described herein, which includes markers mapping within the intervals. In certain embodiments, the invention further provides markers closely genetically linked to, or within approximately 0.5 cM of, the markers provided herein and chromosome intervals whose borders fall between or include such markers, and including markers within approximately 0.4 cM, 0.3 cM, 0.2 cM, and about 0.1 cM of the markers provided herein.

In some embodiments the markers and haplotypes described above can be used for marker assisted selection to produce additional progeny plants comprising the indicated varin modification activity. In some embodiments, backcrossing may be used in conjunction with marker-assisted selection.

Kits for Use in Diagnostic Applications

Kits for use in diagnostic, research, and prognostic applications are also provided by the invention. Such kits may include any or all of the following: assay reagents, buffers, nucleic acids for detecting the target sequences and other hybridization probes and/or primers. The kits may include instructional materials containing directions (i.e., protocols) for the practice of the methods of this invention. While the instructional materials typically comprise written or printed materials, they are not limited to such. Any medium capable of storing such instructions and communicating them to an end user is contemplated by this invention. Such media include, but are not limited to, electronic storage media (e.g., magnetic discs, tapes, cartridges, chips), optical media (e.g., CD ROM), cloud-based media, and the like. Such media may include addresses to internet sites that provide such instructional materials.

EXAMPLES

Aspects of the present teachings can be further understood in light of the following examples, which should not be construed as limiting the scope of the present teachings in any way.

The practice of the present teachings employ, unless otherwise indicated, conventional methods of protein chemistry, biochemistry, recombinant DNA techniques and pharmacology, within the skill of the art. Such techniques are explained fully in the literature. See, e.g., T. Creighton, Proteins: Structures and Molecular Properties, 1993, W. Freeman and Co.; A. Lehninger, Biochemistry, Worth Publishers, Inc. (current addition); J. Sambrook et al., Molecular Cloning: A Laboratory Manual, 2nd Edition, 1989; Methods In Enzymology, S. Colowick and N. Kaplan, eds., Academic Press, Inc.; Remington's Pharmaceutical Sciences, 18th Edition, 1990, Mack Publishing Company, Easton, Pa.; Carey and Sundberg, Advanced Organic Chemistry, Vols. A and B, 3rd Edition, 1992, Plenum Press.

The practice of the present teachings also employ, unless otherwise indicated, conventional methods of statistical analysis, within the skill of the art. Such techniques are explained fully in the literature. See, e.g., J. Little and D. Rubin, Statistical Analysis with Missing Data, 2nd Edition 2002, John Wiley and Sons, Inc., NJ; M. Pepe, The Statistical Evaluation of Medical Tests for Classification and Prediction (Oxford Statistical Science Series) 2003, Oxford University Press, Oxford, UK; X. Zhoue et al., Statistical Methods in Diagnostic Medicine 2002, John Wiley and Sons, Inc., NJ; T. Hastie et. al, The Elements of Statistical Learning: Data Mining, Inference, and Prediction, Second Edition 2009, Springer, N.Y.; W. Cooley and P. Lohnes, Multivariate procedures for the behavioral science 1962, John Wiley and Sons, Inc. NY; E. Jackson, A User's Guide to Principal Components 2003, John Wiley and Sons, Inc., NY.

Example 1—Discovery of Varin Markers

This example describes the discovery of SNP markers associated with increased cannabivarin (from here onwards referred to as "varin") production.

Material

Germplasm used for the analysis was an F2 mapping population (n=142) between a Type I and a Type III accession (Type I: Total THC/Total CBD>3.0; Type II: Total THC/Total CBD: 0.3-3.0; Type III: Total THC/Total CBD <0.3; Germplasm assessment round 2; GAR2) in addition to a set of 67 diverse seed lots consisting of 1-20 accessions each (n=302; germplasm assessments rounds 1 and 3; GAR1 and GAR3).

Cannabinoid Data Collection

Cannabinoid data were obtained through HPLC of mature flower tissue which was dried for at least one week. Total Varin content is defined as the sum of Total Tetrahydrocannabivarin (THCV), Total Cannabidivarin (CBDV), and Total Cannabigerivarin (CBGV). Total THCV was calculated as (0.877*THCVA)+THCV. Total CBDV was calculated as (0.877*CBDVA)+CBD. Total CBGV was calculated as (0.878*CBGVA)+CBGV. Total Varin content data ranged between 0-0.59% for the F2 mapping population and between 0-1.22% for the diverse set of seed lots. The level of detection of the equipment was >0.03 and as a result any values for individual minor cannabinoids lower than this value are reported as zero. THCV and CBDV content data ranged between 0-0.22% and 0-0.52%, respectively for GAR2. THCV and CBDV content data ranged between 0-1.07% and 0-0.48%, respectively for GAR1 and GAR3 combined.

The Varin Ratio, referred to as the ratio between Total Varin (%) by Total Cannabinoids (%; Total Cannabinoids=total THC ((0.877*THCA)+D9−THC)+total CBD ((0.877*CBDA)+CBD)+total CBC ((0.877*CBCA)+CBC)+total CBG ((0.878*CBGA)+CBG)) was used as a means to correct for variation in sample quality and other confounding effects such as trichome density since varins and cannabinoids are produced in the same plant tissues (stalked capitate trichomes) and are produced for a major part by the same biosynthesis pathway. The Varin Ratio ranged between 0-0.053 for the F2 mapping population and between 0-0.068 for the diverse set of seed lots of GAR1 and GAR3.

Comparing Total Varin as well as the Varin Ratio data for the check accession in GAR1 and GAR3 shows that GAR1 had significantly higher values (p=0.026 and p=0.0008, respectively; Table 1). However, when comparing the averages of all accessions used for mapping in these two experiments, GAR3 had higher values as compared to GAR1 (p=5.35E-5 and p=0.0028, respectively; Table 1). It therefore appears that GAR3 contained germplasm representing genetic variation which increases Total Varin as well as Varin Ratio more as compared to the genetics in GAR1.

TABLE 1

Total Varin (% dry weight of flower) and Varin Ratio averages per experiment for the check (type I) and the accessions used for mapping.

| Experiment | Total Varin (%) Check | Varin Ratio Check | Total Varin (%) NAM accessions | Varin Ratio NAM accessions |
|---|---|---|---|---|
| GAR1 | 0.16 | 0.007 | 0.19 | 0.013 |
| GAR3 | 0.14 | 0.006 | 0.26 | 0.016 |

QTL Mapping

The F2 mapping population (n=294) was genotyped with an Illumina bead array. After initial marker QC, further filtering steps were performed to filter out known low quality SNPs, SNPs with large numbers of missing values (>50%), linked SNPs (SNPs in 5 kb regions evaluated for LD>0.2) and SNPs with a minimum allele frequency <1% (vcftools). Subsequently, SNPs deviating from Hardy-Weinberg equilibrium were removed based on a threshold of 1E-06 (plink; Purcell et al. 2007, AJHG 81(3): 559-575). After these filtering steps, 7607 array SNPs remained for map construction and QTL analysis.

A linkage map was constructed using the F2 mapping population SNP data using the package MSTmap (http://mstmap.org/). The 294 accessions were evaluated in two consecutive experiments (n=96 and n=198, respectively). Mature flower minor cannabinoid data were obtained from the second experiment through HPLC analysis. Cannabinoid values were averaged across all replicates (up to 3 replicates per accession), resulting in flower cannabinoid data for 142 accessions with at least one replicate each. Most of the missing data points were caused by poor plant health and/or hermaphroditism.

QTLs were mapped on this linkage map using the R package QTL (https://rqtl.org/). QTL mapping of Total Varin (Total THCV+Total CBDV) resulted in the discovery of two significant QTLs on chromosomes 4 and 7 at 51.844 (1.5 LOD support interval between 50.822 and 52.185 cM) and 44.676 cM (1.5 LOD support interval between 41.435 and 54.000 cM), respectively (highest LOD scores per QTL 21.750 and 6.344, respectively, FIG. 1). The linkage map haplotype associated with the highest QTL on chromosome 4 encompasses a 0.94 Mbp region between positions 73,605,274 and 74,545,194 (Cannabis Abacus reference genome version 2 (CsaAba2); FIG. 1). The linkage map haplotype associated with the 1.5 LOD support interval on chromosome 4 encompasses a 5.4 Mbp region between positions 69,222,980 and 74,594,736. The linkage map haplotype associated with the highest QTL on chromosome 7 encompasses a 0.10 Mbp region between positions 59,291,458 and 59,305,086 (CsaAba2; FIG. 1). The haplotype associated with the 1.5 LOD support interval on chromosome 7 encompasses a 5.83 Mbp region between positions 56,158,064 and 61,821,470.

QTL mapping of Varin Ratio resulted in the discovery of two significant QTLs on chromosomes 4 and 7 at 51.844 (1.5 LOD interval between 50.822 and 52.697 cM) and 45.000 cM (1.5 LOD interval between 41.605 and 50.000 cM), respectively (highest LOD scores per QTL 23.848 and 6.725, respectively). The linkage map haplotype associated with the highest QTL on chromosome 4 is the same as for Total Varin (it encompasses a 0.94 Mbp region between positions 73,605,274 and 74,545,194). The haplotype associated with the 1.5 LOD support interval on chromosome 4 encompasses a 6.1 Mbp region between positions 69,222,980 and 75,336,018. The linkage map haplotype associated with the highest QTL on chromosome 7 was inferred based on interval mapping and not associated with a marker, as a result no linkage map haplotype could be determined. The haplotype for the 1.5 LOD interval was between positions 57,171,995 and 61,520,771 (4.3 Mb region).

Mapping of Total THCV values as well as Total THCV presence resulted in 2 QTLs in the same genomic regions as the Total Varin QTLs. QTL mapping of Total CBDV values as well as Total CBDV presence resulted in the detection of a significant QTL on chromosome 7 in the same genomic region as the Total Varin QTL.

TABLE 2

| Corresponding sequence ID | SNP marker name | p-value | type | Ref. call | Alt call | Abacus reference genome position | Chrom. | Left flanking marker haplotype | Right flanking marker haplotype | Position left flanking marker haplotype (bp) | Position right flanking marker haplotype (bp) |
|---|---|---|---|---|---|---|---|---|---|---|---|
| SEQ ID NO: 1 | 142078_3920202 | 1.62E-27 | B | C | A | 72,717,623 | 4 | 142078_3860187 | 142078_3932846 | 72,657,658 | 72,730,265 |
| SEQ ID NO: 2 | 142078_3625974 | 8.32E-16 | X | A | G | 72,413,830 | 4 | 142078_3622001 | 142078_3638408 | 72,409,857 | 72,434,554 |
| SEQ ID NO: 3 | 142078_3550154 | 9.55E-16 | X | T | C | 72,330,901 | 4 | 142078_3507985 | 122946_5887 | 72,283,941 | 72,353,650 |
| SEQ ID NO: 4 | 142078_4766558 | 2.95E-16 | B | G | A | 73,591,604 | 4 | 142078_4721318 | 142078_4780228 | 73,542,722 | 73,605,274 |
| SEQ ID NO: 5 | 142078_1326143 | 6.31E-14 | X | A | C | 69,742,048 | 4 | 142078_1314843 | 142078_1338093 | 69,730,748 | 69,753,998 |
| SEQ ID NO: 6 | 142078_1210539 | 1.00E-13 | X | G | T | 69,610,062 | 4 | Cannabis.v1_scf2450.35342_100 | 142078_1223276 | 69,595,111 | 69,623,124 |
| SEQ ID NO: 7 | 142193_1677355 | 1.10E-13 | A | T | G | 76,062,454 | 4 | 142193_1673355 | 142193_1686698 | 76,058,454 | 76,071,798 |
| SEQ ID NO: 8 | 75806_4137 | 3.72E-15 | X | T | C | 66,562,042 | 4 | 123913_6028 | 142582_1198181 | 66,539,745 | 66,647,763 |
| SEQ ID NO: 9 | 142078_3253223 | 1.48E-12 | X | A | C | 72,070,492 | 4 | 142078_3238681 | 142078_3261138 | 72,052,129 | 72,095,249 |
| SEQ ID NO: 10 | Cannabis.v1_scf1667-61642_101 | 2.88E-12 | A | C | A | 74,886,331 | 4 | 142193_535381 | 142193_555905 | 74,880,600 | 74,901,126 |
| SEQ ID NO: 11 | Cannabis.v1_scf5183-21792_100 | 6.03E-12 | X | G | C | 72,386,361 | 4 | 142078_3589579 | 142078_3617106 | 72,377,499 | 72,404,962 |
| SEQ ID NO: 12 | 142078_577614 | 2.09E-11 | X | G | T | 68,871,783 | 4 | 142078_557995 | 130277_722 | 68,845,023 | 68,875,411 |
| SEQ ID NO: 13 | 142078_3704759 | 1.91E-11 | B | G | A | 72,500,945 | 4 | 142078_3700082 | 142078_3717574 | 72,496,268 | 72,513,761 |
| SEQ ID NO: 14 | 142078_1847669 | 8.71E-11 | X | G | C | 70,313,071 | 4 | 142078_1830079 | 142078_1861170 | 70,295,481 | 70,326,573 |
| SEQ ID NO: 15 | 142078_292186 | 3.98E-09 | B | C | T | 68,551,901 | 4 | 142078_228609 | 142078_326999 | 68,475,585 | 68,594,870 |
| SEQ ID NO: 16 | 105108_3515 | 1.20E-12 | X | G | C | 42,457,670 | 4 | 141066_113575 | 141066_141659 | 42,441,379 | 42,469,463 |
| SEQ ID NO: 17 | 142193_1314778 | 5.01E-12 | B | A | T | 75,695,688 | 4 | 142193_1306685 | 142193_1326687 | 75,687,594 | 75,707,597 |
| SEQ ID NO: 18 | 142078_1437037 | 1.20E-08 | B | G | A | 69,860,635 | 4 | 102664_130 | 142078_1459884 | 69,809,534 | 69,883,481 |
| SEQ ID NO: 19 | 142498_504213 | 9.55E-09 | A | T | A | 65,944,497 | 4 | 145827_5552 | Cannabis.v1_scf535.75066_101 | 65,913,302 | 66,008,134 |
| SEQ ID NO: 20 | 141588_1041814 | 2.34E-11 | B, X | G | C | 44,409,131 | 4 | 141588_1047596 | 141588_1033673 | 44,403,349 | 44,417,272 |
| SEQ ID NO: 21 | 141536_1732919 | 3.09E-10 | X | A | G | 59,679,717 | 4 | 141536_1702981 | 141536_1737270 | 59,649,779 | 59,684,068 |
| SEQ ID NO: 22 | 142593_2516791 | 1.10E-14 | B | G | A | 60,682,036 | 7 | 142593_2508127 | 142593_2530585 | 60,673,372 | 60,695,830 |

TABLE 2-continued

| Corresponding sequence ID | SNP marker name | p-value | type | Ref. call | Alt call | Abacus reference genome position | Chrom. | Left flanking marker haplotype | Right flanking marker haplotype | Position left flanking marker haplotype (bp) | Position right flanking marker haplotype (bp) |
|---|---|---|---|---|---|---|---|---|---|---|---|
| SEQ ID NO: 23 | 142193_544418 | 3.16E-11 | B | C | A | 74,889,638 | 4 | 142193_535381 | 142193_555905 | 74,880,600 | 74,901,126 |
| SEQ ID NO: 24 | 137716_10170 | 8.91E-10 | X | G | A | 42,260,741 | 4 | 138905_127660 | 141066_29491 | 42,235,386 | 42,327,915 |
| SEQ ID NO: 25 | 141066_96797 | 8.91E-10 | X | G | A | 42,424,601 | 4 | 141066_58456 | 141066_113575 | 42,377,261 | 42,441,379 |
| SEQ ID NO: 26 | 141066_131854 | 8.91E-10 | X | A | T | 42,459,658 | 4 | 141066_113575 | 141066_141659 | 42,441,379 | 42,469,463 |
| SEQ ID NO: 27 | 142078_2113828 | 4.57E-09 | X | T | A | 70,616,713 | 4 | 142078_2100111 | 142078_2133291 | 70,602,918 | 70,636,176 |
| SEQ ID NO: 28 | 142078_2101225 | 8.71E-09 | X | C | T | 70,604,032 | 4 | 142078_2100111 | 142078_2133291 | 70,602,918 | 70,636,176 |
| SEQ ID NO: 29 | Cannabis.v1_scf1614-34746_100 | 4.37E-08 | B, X | T | G | 26,454,266 | 4 | 142250_449324 | 142250_528752 | 26,394,188 | 26,487,178 |
| SEQ ID NO: 30 | 142078_2120695 | 1.41E-08 | B | A | G | 70,623,580 | 4 | 142078_2100111 | 142078_2133291 | 70,602,918 | 70,636,176 |
| SEQ ID NO: 31 | 142078_2108403 | 2.40E-08 | B | G | C | 70,611,260 | 4 | 142078_2100111 | 142078_2133291 | 70,602,918 | 70,636,176 |
| SEQ ID NO: 32 | 107657_19015 | 2.95E-11 | X | G | A | 62,122,798 | 4 | 140681_105156 | Cannabis.v1_scf140.50542_101 | 62,093,721 | 62,129,504 |
| SEQ ID NO: 33 | 141539_889015 | 1.58E-07 | A | T | C | 60,918,190 | 4 | 141539_922097 | 141539_695730 | 60,874,259 | 61,160,176 |
| SEQ ID NO: 34 | 142593_2843997 | 5.50E-15 | B | T | C | 61,014,416 | 7 | 142593_2841509 | 142593_2851984 | 61,011,928 | 61,022,403 |
| SEQ ID NO: 35 | 142498_946327 | 8.71E-07 | A | A | T | 65,379,561 | 4 | 142498_966118 | Cannabis.v1_scf2509.28688_100 | 65,355,808 | 65,382,522 |
| SEQ ID NO: 36 | Cannabis.v1_scf1899-49684_101 | 3.72E-07 | X | A | C | 39,110,266 | 4 | 141136_248713 | 141136_336333 | 39,106,806 | 39,198,241 |
| SEQ ID NO: 37 | 141588_698298 | 2.95E-07 | X | G | A | 44,819,952 | 4 | 141588_705411 | 141588_687895 | 44,812,839 | 44,830,355 |
| SEQ ID NO: 38 | 141911_847832 | 8.32E-09 | X | G | T | 50,680,227 | 4 | 141911_817392 | 141911_934580 | 50,648,892 | 50,774,281 |
| SEQ ID NO: 39 | 141588_872012 | 3.24E-07 | X | C | T | 44,601,335 | 4 | 141588_900636 | 141588_864857 | 44,555,718 | 44,608,490 |
| SEQ ID NO: 40 | Cannabis.v1_scf276-285935_100 | 3.24E-07 | X | G | A | 44,623,676 | 4 | 141588_854448 | 141588_849165 | 44,619,140 | 44,624,423 |
| SEQ ID NO: 41 | 141588_843688 | 3.24E-07 | X | G | T | 44,629,900 | 4 | 141588_849165 | 141588_837908 | 44,624,423 | 44,635,679 |
| SEQ ID NO: 42 | 141588_732634 | 3.24E-07 | X | G | A | 44,759,390 | 4 | 141588_740586 | 141588_725441 | 44,751,438 | 44,773,432 |
| SEQ ID NO: 43 | 141588_650796 | 3.24E-07 | X | G | A | 44,867,872 | 4 | 141588_657909 | 124183_8856 | 44,860,759 | 44,883,368 |
| SEQ ID NO: 44 | Cannabis.v1_scf3658-4502_101 | 8.91E-07 | B | C | T | 27,064,107 | 4 | 142250_982210 | 142250_1028117 | 27,021,230 | 27,067,180 |
| SEQ ID NO: 45 | 141588_811200 | 5.50E-07 | X | C | A | 44,672,313 | 4 | 141588_822852 | 141588_803539 | 44,650,802 | 44,679,975 |

TABLE 2-continued

| Corresponding sequence ID | SNP marker name | p-value | type | Ref. call | Alt call | Abacus reference genome position | Chrom. | Left flanking marker haplotype | Right flanking marker haplotype | Position left flanking marker haplotype (bp) | Position right flanking marker haplotype (bp) |
|---|---|---|---|---|---|---|---|---|---|---|---|
| SEQ ID NO: 46 | 141750_1008206 | 1.00E-08 | X | G | C | 40,776,686 | 4 | 141750_1063875 | 141750_998088 | 40,694,357 | 40,786,739 |
| SEQ ID NO: 47 | 141539_692672 | 1.12E-07 | X | T | C | 61,163,234 | 4 | 141539_695730 | 134058_6596 | 61,160,176 | 61,197,205 |
| SEQ ID NO: 48 | 141588_1407653 | 2.29E-11 | X | G | T | 43,942,890 | 4 | 141588_1452579 | 141588_1335465 | 43,890,681 | 44,027,031 |
| SEQ ID NO: 49 | 142250_1987729 | 6.61E-10 | B | G | T | 28,202,114 | 4 | 142250_1917324 | 142250_2002252 | 28,150,049 | 28,216,587 |
| SEQ ID NO: 50 | 142593_2671993 | 4.79E-13 | B | T | C | 60,842,314 | 7 | 142593_2637764 | 142593_2691470 | 60,804,184 | 60,861,899 |
| SEQ ID NO: 51 | 142593_2666596 | 5.50E-13 | B | T | A | 60,836,917 | 7 | 142593_2637764 | 142593_2691470 | 60,804,184 | 60,861,899 |
| SEQ ID NO: 52 | 142593_2561020 | 7.94E-13 | B | A | G | 60,726,211 | 7 | 142593_2552839 | 142593_2565374 | 60,718,030 | 60,730,565 |
| SEQ ID NO: 53 | 142593_2694605 | 1.62E-12 | B | T | C | 60,865,034 | 7 | 142593_2691470 | 142593_2698637 | 60,861,899 | 60,869,066 |
| SEQ ID NO: 54 | 141840_416132 | 1.38E-11 | B | A | G | 61,689,496 | 7 | 141840_410839 | 141840_422198 | 61,684,203 | 61,695,330 |
| SEQ ID NO: 55 | 142250_2334807 | 1.45E-06 | X | G | A | 28,499,186 | 4 | 142250_2222937 | 142250_2242636 | 28,487,316 | 28,507,015 |
| SEQ ID NO: 56 | 142250_2380876 | 9.77E-07 | X | C | G | 28,655,285 | 4 | 142250_2371515 | 142250_2385434 | 28,641,339 | 28,659,845 |
| SEQ ID NO: 57 | 141840_61026 | 7.76E-12 | B | A | G | 61,315,097 | 7 | 141840_28460 | 141840_70758 | 61,282,508 | 61,324,829 |
| SEQ ID NO: 58 | 141840_125137 | 7.76E-12 | B | C | T | 61,384,518 | 7 | 141840_112505 | 118198_2742 | 61,371,885 | 61,399,597 |
| SEQ ID NO: 59 | 141840_271843 | 4.90E-11 | B | A | C | 61,543,623 | 7 | 131410_7533 | 141840_289618 | 61,535,971 | 61,563,546 |
| SEQ ID NO: 60 | 141840_131915 | 1.82E-11 | B | A | T | 61,391,296 | 7 | 141840_112505 | 118198_2742 | 61,371,885 | 61,399,597 |
| SEQ ID NO: 61 | 142250_2293974 | 6.31E-09 | X | G | A | 28,563,750 | 4 | 142250_2242636 | 142250_2305272 | 28,507,015 | 28,575,047 |
| SEQ ID NO: 62 | 142078_3894722 | 1.74E-13 | B | C | T | 72,692,194 | 4 | 142078_3860187 | 142078_3932846 | 72,657,658 | 72,730,265 |
| SEQ ID NO: 63 | 90_425860 | 3.16E-07 | X | C | A | 1,306,106 | 1 | 90_418766 | 90_436440 | 1,298,626 | 1,316,649 |
| SEQ ID NO: 64 | 90_516765 | 7.94E-07 | X | T | G | 1,408,650 | 1 | 90_489082 | 90_518873 | 1,378,487 | 1,410,751 |
| SEQ ID NO: 65 | 293_1299949 | 1.58E-07 | A | T | C | 96,902,576 | 2 | 293_1305006 | 293_1299799 | 96,897,519 | 96,902,726 |
| SEQ ID NO: 66 | 142372_3159807 | 1.26E-06 | X | A | C | 601,392 | 3 | 142372_3172030 | 142372_3154648 | 589,166 | 606,551 |
| SEQ ID NO: 67 | 142372_2749182 | 5.01E-09 | X | A | C | 1,053,571 | 3 | 142372_2759498 | 142372_2744348 | 1,043,255 | 1,058,405 |
| SEQ ID NO: 68 | 142250_8699831** | 1.26E-08 | X | G | C | 35,933,381 | 4 | 142250_8667430 | 142250_8720726 | 35,900,980 | 35,954,576 |

TABLE 2-continued

| Corresponding sequence ID | SNP marker name | p-value | type | Ref. call | Alt call | Abacus reference genome position | Chrom. | Left flanking marker haplotype | Right flanking marker haplotype | Position left flanking marker haplotype (bp) | Position right flanking marker haplotype (bp) |
|---|---|---|---|---|---|---|---|---|---|---|---|
| SEQ ID NO: 69 | 141488_326503 | 3.98E-07 | X | T | C | 80,090,345 | 4 | 141488_322143 | 141488_333598 | 80,085,984 | 80,097,441 |
| SEQ ID NO: 70 | 141488_351566** | 1.26E-09 | X | T | A | 80,115,357 | 4 | 141488_341572 | 141488_360273 | 80,105,416 | 80,127,527 |
| SEQ ID NO: 71 | 141488_432025** | 2.51E-10 | X | G | C | 80,199,302 | 4 | 141488_422798 | 141488_437671 | 80,190,075 | 80,204,949 |
| SEQ ID NO: 72 | 141488_461840** | 3.98E-10 | A | T | C | 80,229,056 | 4 | 141488_451427 | 141488_465971 | 80,218,646 | 80,233,188 |
| SEQ ID NO: 73 | 141488_577527 | 2.00E-07 | X | C | G | 80,348,481 | 4 | 141488_569396 | Cannabis.v1_scf1179.83564_100 | 80,340,078 | 80,367,295 |
| SEQ ID NO: 74 | 141488_582366** | 6.31E-12 | X | C | A | 80,353,319 | 4 | 141488_569396 | Cannabis.v1_scf1179.83564_100 | 80,340,078 | 80,367,295 |
| SEQ ID NO: 75 | 141488_588603** | 2.51E-12 | X | C | T | 80,361,168 | 4 | 141488_569396 | Cannabis.v1_scf1179.83564_100 | 80,340,078 | 80,367,295 |
| SEQ ID NO: 76 | 141488_592975 | 5.01E-07 | X | C | A | 80,365,496 | 4 | 141488_569396 | Cannabis.v1_scf1179.83564_100 | 80,340,078 | 80,367,295 |
| SEQ ID NO: 77 | 141488_657452** | 3.98E-12 | X | C | G | 80,429,514 | 4 | 141488_655251 | 141488_661741 | 80,427,312 | 80,443,930 |
| SEQ ID NO: 78 | 141488_685576** | 2.00E-10 | X | C | A | 80,467,768 | 4 | 141488_680647 | 141488_698028 | 80,462,839 | 80,480,220 |
| SEQ ID NO: 79 | 141488_718654** | 1.58E-10 | X | G | A | 80,500,846 | 4 | 141488_707567 | 141488_739914 | 80,489,759 | 80,531,379 |
| SEQ ID NO: 80 | 141488_759240 | 6.31E-07 | X | T | G | 80,554,549 | 4 | 141488_748628 | 141488_775888 | 80,543,937 | 80,571,063 |
| SEQ ID NO: 81 | 141488_804059 | 1.26E-06 | X | C | G | 80,599,233 | 4 | 347_447507 | 141488_806258 | 80,596,780 | 80,601,432 |
| SEQ ID NO: 82 | 125246_20932 | 2.51E-09 | X | G | A | 42,019,510 | 5 | 125246_12778 | 128973_16521 | 42,011,356 | 42,089,635 |
| SEQ ID NO: 83 | 199557_20501 | 3.98E-07 | B | C | T | 1,477,638 | 6 | 199557_71162 | 75510_360 | 1,436,177 | 1,617,387 |
| SEQ ID NO: 84 | 103533_2046 | 1.26E-07 | X | G | T | 1,547,216 | 6 | 199557_71162 | 75510_360 | 1,436,177 | 1,617,387 |
| SEQ ID NO: 85 | 139181_57592 | 1.58E-09 | X | A | C | 9,352,336 | 6 | 130304_10952 | 141337_1260 | 9,351,976 | 9,357,910 |
| SEQ ID NO: 86 | 120967_267 | 1.26E-08 | B | C | G | 21,255,914 | 6 | 81189_1282 | 196_5934 | 21,185,192 | 21,356,602 |
| SEQ ID NO: 87 | 77309_117 | 3.16E-07 | B | A | G | 21,288,458 | 6 | 81189_1282 | 196_5934 | 21,185,192 | 21,356,602 |
| SEQ ID NO: 88 | 141826_380714** | 1.58E-11 | B | A | T | 25,701,639 | 6 | 141826_76348 | 142467_35146 | 25,574,335 | 25,702,216 |
| SEQ ID NO: 89 | 141145_18419 | 5.01E-08 | B | A | G | 46,375,436 | 6 | 141145_21826 | 141145_9342 | 46,372,026 | 46,383,991 |
| SEQ ID NO: 90 | 133613_11055 | 2.51E-08 | B | A | T | 53,088,610 | 6 | 139552_25688 | Cannabis.v1_scf1239.51984_84 | 53,025,697 | 53,123,500 |
| SEQ ID NO: 91 | 140442_11150 | 1.58E-14 | X | T | A | 54,422,975 | 6 | Cannabis.v1_scf2144.23459_100 | 127299_134 | 54,418,137 | 54,449,136 |

TABLE 2-continued

| Corresponding sequence ID | SNP marker name | p-value | type | Ref. call | Alt call | Abacus reference genome position | Chrom. | Left flanking marker haplotype | Right flanking marker haplotype | Position left flanking marker haplotype (bp) | Position right flanking marker haplotype (bp) |
|---|---|---|---|---|---|---|---|---|---|---|---|
| SEQ ID NO: 92 | 393_150329 | 1.00E-27 | X | T | C | 56,278,544 | 6 | 393_185365 | 393_52202 | 56,236,381 | 56,394,257 |
| SEQ ID NO: 93 | 231_15997 | 3.98E-11 | B | A | G | 63,262,835 | 6 | 140485_2016 | 132997_1843 | 63,181,444 | 63,331,822 |
| SEQ ID NO: 94 | 123683_23309 | 2.51E-14 | B | A | C | 64,641,858 | 6 | 202206_29766 | 123683_155 | 64,639,895 | 64,665,011 |
| SEQ ID NO: 95 | 321_12940 | 1.00E-06 | X | T | C | 82,769,380 | 6 | 321_6046 | 321_25322 | 82,762,486 | 82,781,902 |
| SEQ ID NO: 96 | 81097_814 | 2.51E-07 | X | T | C | 84,428,826 | 6 | 187114_2047 | 198_266631 | 84,381,966 | 84,465,476 |
| SEQ ID NO: 97 | 424_7576172** | 3.98E-10 | X | G | A | 12,654,209 | 9 | 424_7552085 | 424_7580025 | 12,624,051 | 12,658,062 |
| SEQ ID NO: 98 | 424_12451946 | 1.26E-06 | X | A | C | 18,343,719 | 9 | 424_12448868 | 424_12467409 | 18,340,641 | 18,359,336 |
| SEQ ID NO: 99 | 141768_2132603 | 1.00E-07 | X | A | G | 27,937,504 | 9 | 141768_2151596 | 141768_2109274 | 27,918,393 | 27,960,833 |
| SEQ ID NO: 100 | 142335_191216 | 1.58E-08 | B | G | C | 51,967,498 | 9 | 142335_150076 | 142335_204753 | 51,920,670 | 51,981,036 |
| SEQ ID NO: 101 | 142316_804337 | 3.16E-07 | X | C | T | 58,316,394 | 9 | 142316_752597 | 126383_430 | 58,264,648 | 58,354,901 |
| SEQ ID NO: 102 | 140807_1546* | 6.31E-08 | X | A | G | 13,708,867 | 1 | 157_761752 | 157_1062688 | 13,542,717 | 13,858,559 |
| SEQ ID NO: 103 | 369_303184 | 9.55E-08 | B | G | A | 21,374,553 | 1 | 369_293586 | 369_337282 | 21,364,989 | 21,386,103 |
| SEQ ID NO: 104 | 142225_852* | 3.16E-49 | X | G | C | 33,426,602 | 1 | 141915_1321 | 142470_18320 | 33,423,461 | 33,483,608 |
| SEQ ID NO: 105 | 141673_1924981 | 5.89E-08 | X | G | A | 57,945,889 | 1 | Cannabis.v1_scf3780.20014_100 | 138159_3473 | 57,926,021 | 57,945,895 |
| SEQ ID NO: 106 | 141677_25193 | 1.17E-07 | X | A | C | 74,769,414 | 1 | 102084_1104 | 141677_13830 | 74,762,030 | 74,781,979 |
| SEQ ID NO: 107 | 132136_9628 | 2.04E-07 | A | T | C | 5,078,822 | 2 | 97722_470 | 167_2253514 | 5,066,772 | 5,092,655 |
| SEQ ID NO: 108 | 167_1167836 | 3.24E-07 | A | T | C | 6,291,492 | 2 | 167_1176329 | 167_1146929 | 6,282,862 | 6,314,717 |
| SEQ ID NO: 109 | 142353_26553* | 3.72E-08 | X | G | A | 68,155,237 | 2 | 142353_32479 | 142353_21782 | 68,149,311 | 68,160,008 |
| SEQ ID NO: 110 | 116167_2793 | 1.05E-06 | B | G | A | 82,116,647 | 2 | 141810_1957 | 344_10921 | 82,069,986 | 82,169,750 |
| SEQ ID NO: 111 | 411_1266367 | 2.14E-08 | X | A | G | 78,793,988 | 3 | 411_1270956 | 411_1260253 | 78,789,397 | 78,800,102 |
| SEQ ID NO: 112 | 142193_4943614 | 3.39E-07 | B | T | C | 79,698,853 | 4 | 142193_4938680 | 142193_4950097 | 79,693,919 | 79,705,336 |
| SEQ ID NO: 113 | 141488_70104 | 1.58E-07 | X | T | C | 79,824,851 | 4 | 141488_65730 | 141488_105584 | 79,820,477 | 79,862,264 |
| SEQ ID NO: 114 | 129891_10941* | 2.40E-11 | X | A | G | 79,972,170 | 4 | 141488_210149 | 129891_174 | 79,966,786 | 79,982,937 |

TABLE 2-continued

| Corresponding sequence ID | SNP marker name | p-value | type | Ref. call | Alt call | Abacus reference genome position | Chrom. | Left flanking marker haplotype | Right flanking marker haplotype | Position left flanking marker haplotype (bp) | Position right flanking marker haplotype (bp) |
|---|---|---|---|---|---|---|---|---|---|---|---|
| SEQ ID NO: 115 | 141488_247424 | 1.05E-06 | X | A | G | 80,011,567 | 4 | 128687_5749 | 141488_269684 | 79,987,142 | 80,033,725 |
| SEQ ID NO: 116 | Cannabis.v1_scf1353.38456_101* | 1.70E-11 | X | T | C | 80,012,804 | 4 | 128687_5749 | 141488_269684 | 79,987,142 | 80,033,725 |
| SEQ ID NO: 117 | 141488_253018 | 3.72E-10 | B | T | C | 80,017,161 | 4 | 128687_5749 | 141488_269684 | 79,987,142 | 80,033,725 |
| SEQ ID NO: 118 | 141488_264076* | 5.13E-07 | X | T | C | 80,028,174 | 4 | 128687_5749 | 141488_269684 | 79,987,142 | 80,033,725 |
| SEQ ID NO: 119 | 141488_287391* | 3.39E-11 | X | G | C | 80,051,232 | 4 | 128687_5749 | 141488_291532 | 80,033,725 | 80,055,373 |
| SEQ ID NO: 120 | 141488_308754* | 1.20E-13 | X | A | G | 80,072,595 | 4 | 141488_269684 | 141488_322143 | 80,070,786 | 80,085,984 |
| SEQ ID NO: 121 | 141488_415560 | 7.08E-08 | X | C | A | 80,182,837 | 4 | 141488_306945 | 141488_422798 | 80,177,584 | 80,190,075 |
| SEQ ID NO: 122 | 141488_528550 | 3.09E-08 | X | A | C | 80,299,232 | 4 | 141488_410307 | 141488_535112 | 80,295,031 | 80,305,794 |
| SEQ ID NO: 123 | 141488_718654 | 3.24E-07 | X | G | A | 80,500,846 | 4 | 141488_524349 | 141488_739914 | 80,489,759 | 80,531,379 |
| SEQ ID NO: 124 | 141488_748628 | 7.41E-08 | X | C | T | 80,543,937 | 4 | 141488_707567 | 141488_759240 | 80,531,379 | 80,554,549 |
| SEQ ID NO: 125 | 141488_796227 | 1.82E-08 | X | C | T | 80,591,401 | 4 | 141488_739914 | 347_447507 | 80,586,011 | 80,596,780 |
| SEQ ID NO: 126 | 197_1007670 | 8.32E-10 | B | A | G | 54,569,276 | 6 | 141488_790837 | 197_935474 | 54,541,813 | 54,651,452 |
| SEQ ID NO: 127 | 113321_6502 | 4.07E-07 | X | G | A | 78,245,587 | 6 | 197_1035136 | 141004_2972 | 78,245,560 | 78,249,253 |
| SEQ ID NO: 128 | 280_107725 | 1.74E-08 | X | T | C | 78,551,191 | 6 | 141004_6665 | 280_97823 | 78,540,013 | 78,560,829 |
| SEQ ID NO: 129 | 141477_415245 | 8.51E-07 | X | C | T | 80,899,443 | 6 | 280_118109 | 141477_427723 | 80,797,091 | 80,911,870 |
| SEQ ID NO: 130 | 321_137337* | 2.95E-08 | A | T | C | 83,711,056 | 6 | 141477_313433 | 138753_14265 | 83,694,543 | 83,953,839 |
| SEQ ID NO: 131 | 141801_365489 | 8.32E-07 | X | C | T | 11,220,411 | 7 | 321_120746 | 141801_367651 | 11,193,689 | 11,222,573 |
| SEQ ID NO: 132 | 141440_188532 | 7.76E-13 | X | A | G | 41,986,329 | 7 | 141801_349680 | Cannabis.v1_scf357.238502_101 | 41,982,953 | 41,988,552 |
| SEQ ID NO: 133 | 142465_697275* | 9.77E-09 | X | G | A | 47,794,758 | 7 | 141440_191907 | 142465_677341 | 47,792,278 | 47,814,732 |
| SEQ ID NO: 134 | Cannabis.v1_scf3835.18137_100 | 3.24E-09 | NA | G | A | 58,418,614 | 7 | 142465_699755 | 142593_559015 | 58,398,634 | 58,428,139 |
| SEQ ID NO: 135 | 142593_598766 | 4.68E-07 | X | G | A | 58,467,957 | 7 | 142593_535108 | 142593_602588 | 58,463,826 | 58,471,780 |
| SEQ ID NO: 136 | 142593_696671 | 6.61E-09 | X | A | T | 58,607,780 | 7 | 142593_594638 | 142593_725201 | 58,603,250 | 58,634,785 |
| SEQ ID NO: 137 | 142593_825954 | 1.12E-07 | X | C | T | 58,767,876 | 7 | 142593_692141 | 142593_836762 | 58,755,760 | 58,783,491 |

TABLE 2-continued

| Corresponding sequence ID | SNP marker name | p-value | type | Ref. call | Alt call | Abacus reference genome position | Chrom. | Left flanking marker haplotype | Right flanking marker haplotype | Position left flanking marker haplotype (bp) | Position right flanking marker haplotype (bp) |
|---|---|---|---|---|---|---|---|---|---|---|---|
| SEQ ID NO: 138 | un248038_76_77 | 5.13E-07 | A | C | T | 58,788,342 | 7 | 142593_836762 | 142593_842265 | 58,783,491 | 58,788,994 |
| SEQ ID NO: 139 | 142593_953088 | 4.57E-08 | X | A | G | 58,900,646 | 7 | 142593_943837 | Cannabis.v1_sct5743.7791_100 | 58,891,392 | 58,900,981 |
| SEQ ID NO: 140 | 142593_1001463 | 4.79E-08 | A | C | T | 58,949,513 | 7 | 142593_995090 | 127143_729 | 58,943,140 | 58,958,684 |
| SEQ ID NO: 141 | 135838_2796 | 2.69E-10 | X | T | C | 58,995,137 | 7 | 135838_9228 | 142593_1045102 | 58,998,710 | 59,004,318 |
| SEQ ID NO: 142 | 142593_1138108 | 1.02E-07 | X | A | T | 59,119,856 | 7 | 116549_2593 | 142593_1142353 | 59,106,366 | 59,124,101 |
| SEQ ID NO: 143 | 142593_1283036 | 1.66E-07 | A | A | C | 59,285,985 | 7 | 142593_1276185 | 142593_1288509 | 59,279,134 | 59,291,458 |
| SEQ ID NO: 144 | 142593_1291062 | 1.23E-06 | B | G | C | 59,294,013 | 7 | 142593_1288509 | 142593_1314314 | 59,291,458 | 59,320,748 |
| SEQ ID NO: 145 | 142593_1302135 | 1.45E-15 | X | G | A | 59,305,086 | 7 | 142593_1288509 | 142593_1314314 | 59,291,458 | 59,320,748 |
| SEQ ID NO: 146 | 142593_1336537 | 1.45E-07 | A | A | G | 59,349,246 | 7 | 142593_1316266 | 142593_1346741 | 59,322,700 | 59,359,452 |
| SEQ ID NO: 147 | 142593_1387225 | 1.70E-12 | X | G | A | 59,400,111 | 7 | 142593_1382994 | 142593_1404608 | 59,395,879 | 59,424,272 |
| SEQ ID NO: 148 | 142593_1427427 | 1.10E-13 | X | C | T | 59,457,070 | 7 | 142593_1426611 | 142593_1447509 | 59,456,254 | 59,493,821 |
| SEQ ID NO: 149 | 142593_1664077 | 1.86E-07 | X | A | G | 59,740,097 | 7 | 142593_1652544 | 142593_1689440 | 59,728,563 | 59,765,123 |
| SEQ ID NO: 150 | 142593_1693931 | 2.69E-07 | X | T | C | 59,769,614 | 7 | 142593_1693709 | 142593_1698008 | 59,769,392 | 59,773,691 |
| SEQ ID NO: 151 | 142593_1891259 | 9.77E-15 | X | G | A | 60,004,461 | 7 | 142593_1879958 | 142593_1913106 | 59,993,160 | 60,026,309 |
| SEQ ID NO: 152 | 142593_2106455 | 3.98E-15 | X | C | T | 60,246,243 | 7 | 142593_2104091 | 142593_2112886 | 60,243,878 | 60,252,673 |
| SEQ ID NO: 153 | 142593_2160414 | 1.12E-15 | X | C | G | 60,300,000 | 7 | 142593_2156380 | 142593_2165824 | 60,295,966 | 60,305,410 |
| SEQ ID NO: 154 | 142593_2265578 | 8.13E-13 | X | G | A | 60,405,904 | 7 | 142593_2256478 | 142593_2268303 | 60,396,804 | 60,408,629 |
| SEQ ID NO: 155 | 142593_2376437 | 7.41E-15 | X | T | C | 60,527,155 | 7 | 142593_2368332 | 142593_2379228 | 60,519,050 | 60,529,946 |
| SEQ ID NO: 156 | 142593_2565374 | 4.47E-13 | X | G | A | 60,730,565 | 7 | 142593_2561020 | 142593_2568942 | 60,726,211 | 60,734,133 |
| SEQ ID NO: 157 | 142593_2588342 | 3.31E-14 | X | G | A | 60,753,532 | 7 | 142593_2580585 | 142593_2621910 | 60,745,776 | 60,788,329 |
| SEQ ID NO: 158 | 142593_2772843 | 2.00E-14 | X | G | A | 60,943,279 | 7 | 142593_2767522 | 142593_2777334 | 60,937,958 | 60,947,768 |
| SEQ ID NO: 159 | 142593_2805919 | 1.74E-12 | X | T | C | 60,976,341 | 7 | 142593_2781277 | 142593_2811045 | 60,951,711 | 60,981,467 |
| SEQ ID NO: 160 | 142593_2824003 | 5.75E-14 | X | A | G | 60,994,423 | 7 | 142593_2818258 | 142593_2826371 | 60,988,678 | 60,996,791 |

TABLE 2-continued

| Corresponding sequence ID | SNP marker name | p-value | type | Ref. call | Alt call | Abacus reference genome position | Chrom. | Left flanking marker haplotype | Right flanking marker haplotype | Position left flanking marker haplotype (bp) | Position right flanking marker haplotype (bp) |
|---|---|---|---|---|---|---|---|---|---|---|---|
| SEQ ID NO: 161 | 142593_2836644 | 3.55E-16 | X | T | C | 61,007,064 | 7 | 142593_2828765 | 142593_2843997 | 60,999,185 | 61,014,416 |
| SEQ ID NO: 162 | 141840_10828 | 3.02E-07 | X | T | G | 61,258,755 | 7 | 141840_4653 | 141840_17886 | 61,252,580 | 61,265,813 |
| SEQ ID NO: 163 | 141840_284460* | 1.86E-38 | X | T | A | 61,282,508 | 7 | 141840_17886 | 141840_61026 | 61,265,813 | 61,315,097 |
| SEQ ID NO: 164 | 141840_511814 | 1.86E-13 | A | T | A | 61,305,861 | 7 | 141840_17886 | 141840_61026 | 61,265,813 | 61,315,097 |
| SEQ ID NO: 165 | um259474_79_80* | 1.66E-42 | X | T | C | 61,328,967 | 7 | 141840_70758 | 141840_81469 | 61,324,829 | 61,335,541 |
| SEQ ID NO: 166 | 141840_239615* | 8.91E-14 | X | A | T | 61,504,547 | 7 | 141840_230929 | 195655_1938 | 61,495,886 | 61,513,471 |
| SEQ ID NO: 167 | 141840_325947* | 4.68E-15 | A | T | C | 61,599,429 | 7 | 141840_302429 | 141840_336769 | 61,576,356 | 61,610,251 |
| SEQ ID NO: 168 | 141840_372430* | 4.27E-23 | B | T | C | 61,645,795 | 7 | 141840_361933 | 141840_390902 | 61,635,274 | 61,664,268 |
| SEQ ID NO: 169 | 141840_378162* | 2.82E-52 | X | A | G | 61,651,527 | 7 | 141840_361933 | 141840_390902 | 61,635,274 | 61,664,268 |
| SEQ ID NO: 170 | 141840_385292* | 1.70E-19 | A | T | C | 61,658,656 | 7 | 141840_361933 | 141840_390902 | 61,635,274 | 61,664,268 |
| SEQ ID NO: 171 | 141840_441895 | 2.24E-07 | X | C | G | 61,715,027 | 7 | 141840_432068 | 141840_475273 | 61,705,200 | 61,748,400 |
| SEQ ID NO: 172 | 141840_681190* | 1.78E-20 | A | T | A | 61,989,002 | 7 | 161261_383 | 141840_702827 | 61,899,142 | 62,015,383 |
| SEQ ID NO: 173 | 141840_691350* | 1.41E-26 | X | G | A | 61,999,104 | 7 | 161261_383 | 141840_702827 | 61,899,142 | 62,015,383 |
| SEQ ID NO: 174 | 141840_707354* | 8.32E-21 | X | A | C | 62,019,912 | 7 | 141840_702827 | 141840_824096 | 62,015,383 | 62,126,279 |
| SEQ ID NO: 175 | 141840_721728* | 5.89E-21 | X | A | C | 62,034,938 | 7 | 141840_702827 | 141840_824096 | 62,015,383 | 62,126,279 |
| SEQ ID NO: 176 | 141840_906772* | 7.59E-25 | X | G | T | 62,231,000 | 7 | 141840_884102 | 64499_111 | 62,208,408 | 62,291,873 |
| SEQ ID NO: 177 | 102155_5292 | 7.76E-11 | X | T | C | 62,387,493 | 7 | 136166_12762 | 140868_508226 | 62,303,488 | 62,409,957 |
| SEQ ID NO: 178 | 109486_529 | 1.38E-13 | X | C | G | 62,647,527 | 7 | 132283_3008 | 140868_230733 | 62,632,314 | 62,732,875 |
| SEQ ID NO: 179 | 140868_225626* | 3.31E-16 | A | G | A | 62,737,982 | 7 | 140868_230733 | 140868_211849 | 62,732,875 | 62,751,759 |
| SEQ ID NO: 180 | 140868_220724* | 1.41E-09 | X | G | A | 62,742,884 | 7 | 140868_230733 | 140868_211849 | 62,732,875 | 62,751,759 |
| SEQ ID NO: 181 | 140868_216359* | 3.55E-41 | A | G | A | 62,747,249 | 7 | 140868_230733 | 140868_211849 | 62,732,875 | 62,751,759 |
| SEQ ID NO: 182 | 140868_202351* | 8.91E-55 | X | G | T | 62,761,203 | 7 | 140868_206368 | 140868_185104 | 62,757,240 | 62,778,564 |
| SEQ ID NO: 183 | 140868_196317* | 1.02E-16 | A | A | G | 62,767,237 | 7 | 140868_206368 | 140868_185104 | 62,757,240 | 62,778,564 |

TABLE 2-continued

| Corresponding sequence ID | SNP marker name | p-value | type | Ref. call | Alt call | Abacus reference genome position | Chrom. | Left flanking marker haplotype | Right flanking marker haplotype | Position left flanking marker haplotype (bp) | Position right flanking marker haplotype (bp) |
|---|---|---|---|---|---|---|---|---|---|---|---|
| SEQ ID NO: 184 | 140868_179511* | 1.55E-15 | X | G | A | 62,792,364 | 7 | 140868_185104 | 140868_177962 | 62,778,564 | 62,793,913 |
| SEQ ID NO: 185 | 140868_156260 | 8.32E-13 | X | T | C | 62,815,617 | 7 | 140868_158272 | 140868_149960 | 62,813,605 | 62,821,917 |
| SEQ ID NO: 186 | 140868_121287* | 7.59E-17 | A | T | G | 62,850,589 | 7 | 140868_128727 | 140868_115270 | 62,843,149 | 62,858,327 |
| SEQ ID NO: 187 | 140868_107435 | 1.05E-06 | A | G | T | 62,866,162 | 7 | 140868_112809 | 140868_99748 | 62,860,788 | 62,873,846 |
| SEQ ID NO: 188 | 140868_103015* | 4.79E-18 | A | G | T | 62,870,580 | 7 | 140868_112809 | 140868_99748 | 62,860,788 | 62,873,846 |
| SEQ ID NO: 189 | 140868_60566* | 6.92E-19 | A | G | A | 62,941,027 | 7 | 140868_68791 | 140868_57409 | 62,904,803 | 62,944,184 |
| SEQ ID NO: 190 | 140868_29987* | 5.13E-55 | X | C | T | 62,971,551 | 7 | 140868_47498 | 140868_23884 | 62,954,094 | 62,977,654 |
| SEQ ID NO: 191 | 140868_21724* | 1.58E-20 | X | T | C | 62,979,814 | 7 | 140868_23884 | 140868_14418 | 62,977,654 | 62,987,118 |
| SEQ ID NO: 192 | 140868_8332* | 3.63E-52 | X | G | A | 62,993,205 | 7 | 140868_14418 | 140868_2816 | 62,987,118 | 62,998,721 |
| SEQ ID NO: 193 | 142415_1123082 | 5.13E-07 | A | A | G | 1,348,101 | 9 | 142415_1120521 | 142415_1128560 | 1,345,541 | 1,353,633 |
| SEQ ID NO: 194 | 424_10555780 | 1.66E-08 | B | C | G | 16,113,998 | 9 | 424_10523904 | 424_10575382 | 16,078,155 | 16,133,600 |
| SEQ ID NO: 195 | 424_11546598 | 2.75E-09 | B | G | A | 17,302,948 | 9 | 424_11537880 | 424_11565850 | 17,294,230 | 17,322,228 |
| SEQ ID NO: 196 | 424_11882159 | 4.90E-14 | A | G | A | 17,687,309 | 9 | 424_11776611 | 424_11902260 | 17,577,328 | 17,707,410 |
| SEQ ID NO: 197 | 424_12133507 | 7.76E-08 | X | G | T | 17,980,798 | 9 | 424_12112304 | 424_12149995 | 17,959,161 | 17,998,665 |
| SEQ ID NO: 198 | 424_14302177 | 6.17E-07 | B | G | C | 20,457,181 | 9 | 424_14299593 | 424_14385169 | 20,454,597 | 20,540,690 |
| SEQ ID NO: 199 | 141768_2047138 | 1.26E-07 | B | C | T | 28,057,298 | 9 | 141768_2051395 | 141768_2012967 | 28,053,040 | 28,107,725 |
| SEQ ID NO: 200 | 141239_980212 | 2.63E-07 | X | A | G | 34,290,160 | 9 | 141239_972584 | 141239_994438 | 34,282,531 | 34,312,727 |
| SEQ ID NO: 201 | 188092_144 | 2.69E-07 | X | C | T | 36,400,585 | 9 | 141509_1546856 | Cannabis.v1_scf3894.25028_101 | 36,379,995 | 36,458,224 |
| SEQ ID NO: 202 | 141687_78697* | 1.78E-09 | B | G | T | 45,840,334 | 9 | 141687_117346 | 141687_26393 | 45,801,432 | 45,898,920 |
| SEQ ID NO: 203 | 140742_308066 | 5.01E-07 | X | C | G | 51,591,130 | 9 | 140742_297098 | 142335_27017 | 51,580,161 | 51,771,586 |
| SEQ ID NO: 204 | 142335_5939 | 1.51E-07 | A | C | A | 51,751,347 | 9 | 140742_297098 | 142335_27017 | 51,580,161 | 51,771,586 |
| SEQ ID NO: 205 | 142335_954059* | 8.32E-10 | X | A | T | 52,869,819 | 9 | 142335_812416 | 142335_959001 | 52,696,211 | 52,875,809 |
| SEQ ID NO: 206 | 142316_299798* | 1.82E-09 | B | C | G | 57,745,083 | 9 | 142316_295404 | 169352_5907 | 57,740,672 | 57,771,581 |

TABLE 2-continued

| Corresponding sequence ID | SNP marker name | p-value | type | Ref. call | Alt call | Abacus reference genome position | Chrom. | Left flanking marker haplotype | Right flanking marker haplotype | Position left flanking marker haplotype (bp) | Position right flanking marker haplotype (bp) |
|---|---|---|---|---|---|---|---|---|---|---|---|
| SEQ ID NO: 207 | 142316_538783 | 3.09E-07 | B | A | G | 58,014,320 | 9 | 142316_497464 | 131511_488 | 57,973,407 | 58,065,809 |
| SEQ ID NO: 208 | 118107_6746 | 8.71E-08 | B | G | T | 59,868,248 | 9 | 169_2044759 | 118107_2097 | 59,816,484 | 59,872,907 |
| SEQ ID NO: 209 | 123724_2165 | 1.62E-08 | B | G | T | 8,651,218 | X | 142494_3788220 | 142494_3798158 | 8,645,495 | 8,660,331 |
| SEQ ID NO: 210 | 142494_7010731 | 2.82E-07 | X | G | A | 12,403,249 | X | 142494_7003882 | 142494_7075673 | 12,396,400 | 12,468,050 |
| SEQ ID NO: 211 | 142293_8350062 | 2.04E-07 | B | G | T | 54,956,182 | X | 133051_13896 | 142293_8374176 | 54,910,038 | 54,980,691 |
| SEQ ID NO: 212 | 129510_2422 | 2.51E-08 | B | G | C | 56,498,195 | X | 121178_5772 | Cannabis.v1_scf1698.3251_101 | 56,488,769 | 56,518,228 |
| SEQ ID NO: 213 | 141076_101280 | 2.19E-07 | B | T | C | 56,966,336 | X | 141076_103376 | 141076_96071 | 56,964,240 | 56,971,544 |
| SEQ ID NO: 214 | 142299_1600906 | 9.55E-07 | X | T | C | 66,516,851 | X | 142299_1590502 | 142299_1552593 | 66,503,382 | 66,529,758 |
| SEQ ID NO: 215 | 421_5909899 | 6.17E-08 | B | A | G | 71,142,905 | X | 421_5922555 | 421_5903248 | 71,125,095 | 71,149,556 |
| SEQ ID NO: 216 | 421_5526104 | 1.20E-06 | A | G | A | 71,618,503 | X | 421_5529500 | 421_5496642 | 71,615,107 | 71,655,405 |
| SEQ ID NO: 217 | 421_4052952 | 6.61E-07 | A | A | G | 73,281,407 | X | 421_4066772 | 421_3975927 | 73,267,516 | 73,364,605 |
| SEQ ID NO: 218 | 135235_11613 | 6.61E-07 | A | A | G | 73,399,713 | X | 421_3947219 | 135235_3148 | 73,392,877 | 73,408,179 |
| SEQ ID NO: 219 | 421_2973420 | 3.98E-11 | B | A | G | 74,496,234 | X | 421_2978238 | 421_2970909 | 74,491,416 | 74,498,743 |
| SEQ ID NO: 220 | 421_2789258 | 7.94E-07 | B | C | G | 74,627,738 | X | 421_2867690 | 421_2787376 | 74,601,630 | 74,629,620 |
| SEQ ID NO: 221 | 421_2780311 | 7.24E-07 | A | C | T | 74,636,685 | X | 421_2787376 | 421_2773383 | 74,629,620 | 74,643,609 |
| SEQ ID NO: 222 | 421_2585261 | 8.32E-07 | B | A | G | 74,863,601 | X | 421_2587511 | 421_2580161 | 74,861,351 | 74,868,701 |
| SEQ ID NO: 223 | 421_2280631 | 9.77E-07 | A | G | A | 75,185,443 | X | 421_2287997 | 421_2256952 | 75,178,077 | 75,209,122 |
| SEQ ID NO: 224 | 421_1598102* | 1.38E-08 | B | C | A | 75,920,615 | X | 421_1600195 | 421_1595918 | 75,918,523 | 75,922,799 |
| SEQ ID NO: 225 | 421_1390091 | 1.17E-06 | A | T | C | 76,189,966 | X | 421_1396168 | 421_1366802 | 76,183,892 | 76,213,312 |
| SEQ ID NO: 226 | 170_555139 | 2.45E-07 | B | T | C | 78,539,112 | X | 170_554030 | 170_560514 | 78,538,003 | 78,544,488 |
| SEQ ID NO: 227 | 170_4513981 | 8.91E-07 | B | A | G | 80,362,725 | X | 170_4520692 | 170_4507833 | 80,356,014 | 80,368,873 |
| SEQ ID NO: 228 | 170_4459590 | 2.95E-08 | X | T | A | 80,424,310 | X | 170_4470135 | Cannabis.v1_scf2384.28120_101 | 80,413,765 | 80,434,069 |
| SEQ ID NO: 229 | 170_4368831 | 2.88E-10 | X | T | G | 80,521,410 | X | Cannabis.v1_scf4018.33910_100 | 170_4355901 | 80,516,281 | 80,534,345 |

TABLE 2-continued

| Corresponding sequence ID | SNP marker name | p-value | SNP marker type | Ref. call | Alt call | Abacus reference genome position | Chrom. | Left flanking marker haplotype | Right flanking marker haplotype | Position left flanking marker haplotype (bp) | Position right flanking marker haplotype (bp) |
|---|---|---|---|---|---|---|---|---|---|---|---|
| SEQ ID NO: 230 | 170_4338498 | 1.12E-06 | A | G | T | 80,551,750 | X | 170_4344442 | 170_4333357 | 80,545,805 | 80,556,891 |
| SEQ ID NO: 231 | 170_4279882 | 1.12E-07 | B | A | G | 80,610,117 | X | 170_4315417 | 170_4267929 | 80,574,630 | 80,622,070 |
| SEQ ID NO: 232 | 170_3444229 | 2.95E-07 | X | T | C | 81,555,347 | X | 170_3449290 | 170_3440241 | 81,550,487 | 81,559,370 |
| SEQ ID NO: 233 | 170_3363670 | 2.75E-08 | B | G | T | 81,636,223 | X | 170_3365785 | 170_3357241 | 81,634,101 | 81,642,223 |
| SEQ ID NO: 234 | 139860_60165 | 7.76E-07 | B | A | C | 20,354,173 | 6 | 139860_75065 | 114303_941 | 20320408 | 20483460 |
| SEQ ID NO: 235 | 171_21004641 | 1.17E-06 | B | T | G | 23,016,846 | 8 | 171_20999301 | Cannabis.v1_scf71.189044_101 | 23011506 | 23027425 |
| SEQ ID NO: 236 | 142713_950507 | 6.46E-07 | X | A | G | 5,460,790 | 7 | 142713_964351 | 142713_932357 | 5446945 | 5478973 |
| SEQ ID NO: 237 | 141356_780969 | 2.04E-07 | X | G | A | 27,884,762 | 7 | 141356_815408 | 141356_663765 | 27850202 | 28012619 |
| SEQ ID NO: 238 | 141366_519971 | 9.55E-07 | X | C | A | 34,997,619 | 7 | 141366_485380 | 141366_524919 | 34963027 | 35003079 |
| SEQ ID NO: 239 | 199086_194 | 4.68E-07 | X | T | C | 45,591,259 | 7 | 199046_8779 | 199045_10153 | 45580623 | 45605317 |
| SEQ ID NO: 240 | 140726_195388 | 4.27E-07 | X | C | G | 52,454,110 | 7 | un105509_43_89 | 140726_183076 | 52441872 | 52466415 |
| SEQ ID NO: 241 | 141318_196817 | 6.17E-07 | B | A | G | 57,247,955 | 7 | 141318_269266 | 141318_174028 | 57233796 | 57276534 |
| SEQ ID NO: 242 | 122751_1014 | 4.79E-07 | X | C | T | 58,720,667 | 7 | 142593_778210 | 142593_805106 | 58704675 | 58740782 |

First column, SNP marker number; Second column, SNP marker name; Third column, NAM p-value; Fourth column, SNP marker type; Fifth column, reference allele call; Sixth column, alternative allele call; Seventh column, Abacus reference genome position.
Eighth column, chromosome; Ninth column, left flanking SNP of haplotype surrounding SNP marker; Tenth column, right flanking SNP of haplotype surrounding SNP marker; Eleventh column, Abacus reference genome position left flanking SNP of haplotype surrounding SNP marker; Twelfth column, Abacus reference genome position right flanking SNP of haplotype surrounding SNP marker.
SEQ ID NO. 1-62: SNP markers discovered through Total THCV, Total Varin, and Varin Ratio QTL mapping and NAM of accessions selected to have the KR marker 142078_3920202 to be homozygous alternate allele or heterozygous.
SEQ ID NO. 63-101: SNP markers discovered through NAM of Total Varin of accessions selected to have KR marker 142078_3920202 to be homozygous alternate allele or heterozygous.
SEQ ID NO. 102-233: SNP markers discovered through NAM of Varin Ratio of accessions selected to have KR marker 142078_3920202 to be homozygous alternate allele or heterozygous.
SEQ ID NO. 234-242: SNP markers discovered through NAM of Total THCV of accessions selected to have KR marker 142078_3920202 to be homozygous alternate allele or heterozygous.
*SNP marker is also significantly associated with Varin Ratio.
**SNP marker is also significantly associated with Total Varin.

Association Mapping

The set of 67 diverse seed lots (n=302) was genotyped with an Illumina bead array. SNPs were filtered using the same QC process as described above, however, minor allele frequency cutoff of 5% and no filter for SNPs that are not in Hardy-Weinberg equilibrium was used. This resulted in 33,509 array SNPs for input in nested association mapping (NAM) analysis. Total THCV, Total Varin, and Varin Ratio data were obtained similarly as described above for QTL mapping with the only difference that each accession was grown out as one replicate. NAM was performed using the R package NAM (https://cran.r-project.org/web/packages/NAM/index.html) using seed lots as family structure (GWAS2 function). NAM analysis included a kinship matrix computed by the NAM package. NAM analysis was done for GAR1 and GAR3 combined, as well as separate per experiment. Since the check variety showed significant difference for both Total Varin content as well as the Varin Ratio analysis would need to be performed per experiment. However, since mapping power was low per experiment due to lower numbers of accessions per experiment a final call for candidate markers was made based on strong significant associations in the analysis using the combined GAR1 and GAR3 results and one of the two separate analyses.

Figure 2:
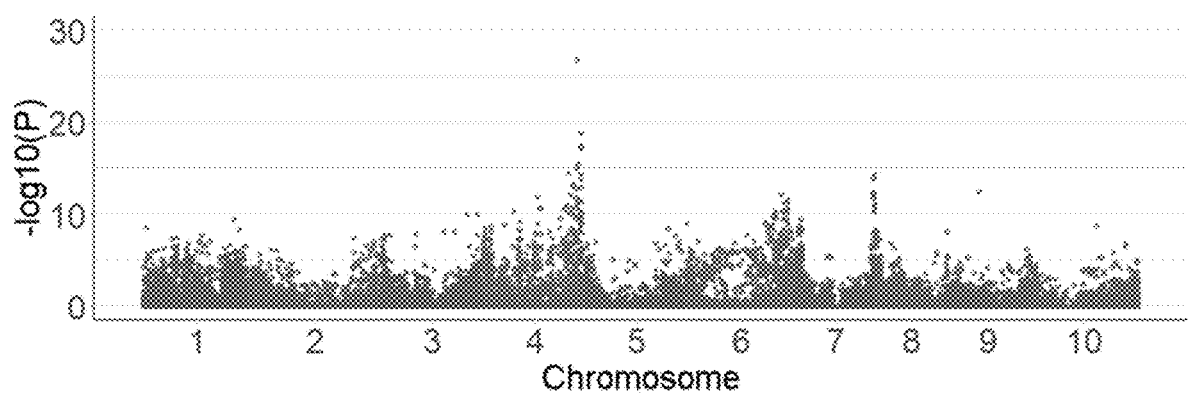
FIG. 2 illustrates −10 log p-values from Total Varin NAM based on 302 accessions from 67 diverse seed lots (x-axis: positions on the Abacus reference genome version CsaAba2; chromosome 10 is the X chromosome).

NAM of Total Varin (FIG. 2) and Total THCV based on GAR1 and GAR3 resulted in the identification of one major NAM peak on chromosome 4 (marker 142078_3920202 at position 72,717,623 of the CsaAba2 reference genome; NAM Total Varin p-value=1.62E-27; NAM Total THCV p-value=1.78E-40). The same marker was identified after NAM using GAR1 data (p-value=1.86E-17). This marker was absent from the GAR3 NAM analysis because minor allele frequency (MAF) was less than 5%. When lowering the MAF cutoff to 1%, marker 142078_3920202 was included and was significantly associated with the trait (p-value=2.69E-08)). NAM of Varin Ratio based on GAR1 and GAR3 resulted in the identification of the same NAM peak on chromosome 4 (marker 142078_3920202 at position 72,717,623; NAM p-value=2.51E-35). NAM of Varin Ratio based on GAR1 and GAR3 separately identified the same NAM peak at marker 142078_3920202 (p-value=3.02E-20 and 1.15E-15, respectively).

The second largest association for Total Varin was observed on chromosome 7 (marker 142593_2843997 at position 61,014,416; NAM p-value=5.50E-15). The same marker showed strong association with Total THCV (p-value for NAM: 6.03E-22) and Varin Ratio (p-value=1.07E-11). Total CBDV did not show strong associations in NAM analysis. NAM of Varin Ratio based on GAR1 and GAR3 separately identified the same peak near marker 142593_2843997 only in GAR3 (p-value=1.35E-09).

In total 432 markers were significantly associated with Total Varin (<1.6E-06 Bonferroni multi-test threshold) after NAM using data for GAR1 and GAR3. These markers were further filtered to be below the multi-test detection threshold for both the combined GAR1 and GAR3 analysis and one experiment (GAR1 or GAR3) to account for experiment effect, resulting in 124 unique markers. In total 346 markers were significantly associated with Varin Ratio (<1.6E-06 Bonferroni multi-test threshold) after NAM using data for GAR1 and GAR3. Filtering this set based on significant associations in GAR1 and/or GAR3 resulted in 225 markers. All of the 124 markers significantly associated with Total Varin overlapped with the set of 225 markers significantly associated with Varin Ratio. Therefore this set of 124 markers was further filtered for genotype effect on Varin Ratio to be greater than 0.01. This effect was calculated as the difference in average Varin Ratio of the genotype with the highest average value and the genotype with the lowest average value. This resulted in a set of 62 significantly associated markers with Total THCV, Total Varin, and Varin Ratio located on chromosomes 1 and 7 (Table 2 SEQ ID. 1-62).

Identification of Candidate Genes

NAM results were filtered for the chromosome containing the QTL region identified on the linkage map to exclude false positives. The marker with the most significant association with Total Varin, Varin Ratio, and Total THCV in NAM analysis (142078_3920202), overlapped with the F2 mapping QTL region 1.5 LOD support interval. Genes near marker 142078_3920202 on chromosome 4 of the CsaAba2 reference genome were subsequently explored for annotations related to the production of varins. The haplotype based on NAM p-values for association with Total Varin surrounding SNP marker 142078_3920202 is flanked by SNPs 142078_3860187 and 142078_3932846, and ranges between positions 72,657,658-72,730,265 on chromosome 4 of the CsaAba2 reference genome. This haplotype contains four genes: RUN/FYVE domain protein (AT1G27850), 3-oxoacyl-[acyl-carrier-protein] reductase, chloroplastic (KR/FABG; AT1G24360), DYNAMIN-like 1C (DL1C: AT1G14830), and DNA polymerase alpha-primase complex, polymerase-associated subunit B (POLA2; AT1G61580). From these four genes one candidate gene was identified: 3-oxoacyl-[acyl-carrier-protein] reductase, chloroplastic (KR; AT1G24360).

The second F2 map QTL for Total Varin, Varin Ratio, and Total THCV is located on chromosome 7 and spans a haplotype between positions 55,59,291,458 and 59,305,086, the 1.5 LOD interval haplotype is between 56,158,064 and 61,821,470. NAM identified a peak for Total Varin and THCV at position 61,014,416 (marker 142593_2843997), which is inside the 1.5 LOD support interval. The haplotype based on NAM p-values for association with Total Varin surrounding SNP marker 142593_2843997 is flanked by SNPs 142593_2841509 and 142593_2851984, and ranges between positions 61,011,928-61,022,403 on chromosome 7 of the CsaAba2 reference genome. This haplotype contains two genes: Inositol polyphosphate multikinase alpha (IPK2a) and V-type proton ATPase subunit e1 (VHA-e1).

Validation of Markers

Elite germplasm as well as single member seed lots were excluded from the NAM analysis so that those data could be used for marker validation. As a result validation was performed using 83 elites and single member seed lots from GAR1 and GAR3.

Marker 142078_3920202

The majority of GAR1 and GAR3 germplasm (n=302) were homozygous for the reference allele, a smaller group was heterozygous, and only 4 accessions were homozygous alternative allele for SNP marker 142078_3920202 (the genotype associated with high Total Varin levels; Table 3A). Accessions with the homozygous alternative allele genotype for this marker are: an accession from seed lot 19GAR3-95 (PGTHB-341328; Total Varin=1.22, highest value in panel of 302 accessions), another accession from the same seed lot (19GAR3-95, PGTHB-342931, Total Varin=0.41; one accession from seed lot 19GAR3-117 (PGTHB-341371; no varin data collected), and one accession from seed lot 19GAR1-27 (PGTHB-333538, Total Varin=0.82). The difference in average Total Varin value between homozygous reference and alternative is 0.62%, the difference in Varin Ratio is 0.045. The three seed lots containing accessions with homozygous alternate alleles for marker 142078_3920202 segregated for the marker and the trait (Table 4).

TABLE 3A

Total Varin averages and accession counts per genotype for marker 142078_3920202 for GAR1 and GAR3.

| 142078_392020 2 genotype | Total Varin average (%) | Total Varin range (%) | Varin Ratio average | Accession count |
|---|---|---|---|---|
| Homozygous reference (CC) | 0.20 | 0-0.47 | 0.013 | 268 |
| Heterozygous (CA) | 0.43 | 0-0.91 | 0.029 | 31 |
| Homozygous alternative (AA) | 0.82 | 0.41-1.22 | 0.057 | 3 |

TABLE 3B

Validation based on elites. Summary Total Varin averages and accessions counts per genotype for marker 142078_3920202 for GAR1 elites. Homozygous alternative allele lacks values because it is absent in elites.

| 142078_3920202 genotype | Total Varin average (%) | Total Varin range (%) | Varin Ratio average | Accession count |
|---|---|---|---|---|
| Homozygous reference (CC) | 0.16 | 0-0.78 | 0.009 | 76** |
| Heterozygous (CA) | 0.31 | 0.12-0.63 | 0.020 | 7 |
| Homozygous alternative (AA) | —* | — | — | — |

*None of the GAR1 elites were homozygous alternative allele for marker 142078_3920202.
**Data for Varin Ratio homozygous reference for 75 accessions.

TABLE 4

Values for Total Varin content and Varin Ratio as well as genotypes for the two markers of the haplotype which segregate in GAR1 and GAR3 for members of the three seed lots with at least one accession which is homozygous alternative allele for 142078_3920202.

| Seed lot | Accession ID | Total Varin (%) | Varin Ratio | 142078_3894722 | 142078_3920202 |
|---|---|---|---|---|---|
| 19GAR1-27 | PGTHB-333534 | 0.63 | 0.044 | T/T | C/A |
| 19GAR1-27 | PGTHB-333537 | 0.54 | 0.035 | T/T | C/A |
| 19GAR1-27 | PGTHB-333538 | 0.82 | 0.006 | T/T | A/A |
| 19GAR1-27 | PGTHB-333539 | 0.13 | 0.010 | C/T | C/C |
| 19GAR3-95 | PGTHB-341304 | 0.74 | 0.044 | C/T | CA |
| 19GAR3-95 | PGTHB-341328 | 1.22 | 0.068 | T/T | A/A |
| 19GAR3-95 | PGTHB-341365 | 0.54 | 0.037 | T/T | C/A |
| 19GAR3-95 | PGTHB-342931 | 0.41 | 0.045 | T/T | A/A |
| 19GAR3-117 | PGTHB-341299 | 0.56 | 0.036 | C/T | C/A |
| 19GAR3-117 | PGTHB-341347 | 0.10 | 0.008 | C/C | C/C |
| 19GAR3-117 | PGTHB-341359 | 0.14 | 0.012 | C/C | C/C |
| 19GAR3-117 | PGTHB-341371 | NA | NA | T/T | A/A |
| 19GAR3-117 | PGTHB-342359 | 0.35 | 0.031 | C/T | C/A |
| 19GAR3-117 | PGTHB-342878 | 0.48 | 0.034 | C/T | C/A |
| 19GAR3-117 | PGTHB-342935 | 0.45 | 0.038 | C/T | C/A |

TABLE 5

NAM p-values for SNPs inside and flanking the haplotype containing marker 42078_3920202 for Total THCV, Varin Ratio, and Total Varin based on data from GAR1 and GAR3.

| Marker | Position | Total THCV | Varin Ratio | Total Varin |
|---|---|---|---|---|
| 142078_3860187 | 72,657,657 | 6.17E-04 | 1.55E-01 | 8.91E-02 |
| 142078_3894722 | 72,692,193 | 1.17E-22 | 1.35E-17 | 1.74E-13 |
| 142078_3898764* | 72,696,236 | — | — | — |
| 142078_3920202 | 72,717,622 | 1.78E-40 | 2.51E-35 | 1.62E-27 |
| 142078_3932846 | 72,730,264 | 1.29E-01 | 1.45E-03 | 1.95E-02 |

*SNP had MAF <5% in the studied population, filtered from NAM.

Besides marker 142078_3920202 the haplotype contains markers 142078_3894722 and 142078_3898764 (both inside the KR/FabG candidate gene; Table 5). No NAM p-value is available for the latter marker since it was monomorphic in GAR1 and GAR3. 142078_3894722 is significantly associated with Total THCV, Total Varin content and Varin Ratio, but the level of significance is lower as compared to 142078_390202. 142078_3898764 was excluded from NAM analysis due to low MAF. The accessions in the seed lots containing the beneficial haplotype (Table 6) are all homozygous reference allele for this marker. Verifying all GAR1 and GAR3 data including the elites and single member seed lots (which were not used for NAM analysis) identified 7 accessions with heterozygous genotype (T/C) for marker 142078_3898764. One of these accessions had a homozygous alternative (A/A) for the main marker 142078_3920202 and had the highest level of Total Varin among the set (Table 6). This level of Total Varin was in the same range as the accessions with the A/A genotype for marker 142078_3920202 in the set of accessions used for NAM (0.41-1.22%). The range of Total Varin for the accessions that were heterozygous for both markers is in the same range as the NAM accessions which were heterozygous for the main marker, 142078_3920202. These data provide additional validation for marker 142078_3920202 to be associated with Total Varin increase.

TABLE 6

| Plant ID | Seed lot* | 142078_3894722 | 142078_3898764 | 142078_3920202 | Varin Ratio | Total Varin (%) |
|---|---|---|---|---|---|---|
| 14C-1-1477 | elite | C/T | T/C | C/A | 0.018 | 0.18 |
| 31C-1-1481 | elite | T/T | T/C | C/A | 0.009 | 0.11 |
| 24-345-1200 | 19GAR1-24 | T/T | T/C | C/A | NA | 0.31 |
| 39-439-1235 | elite | NA | T/C | A/A | NA | 0.66 |
| 15C-1-1462 | elite | T/T | T/C | C/A | 0.025 | 0.36 |
| 24-336-1191 | 19GAR1-24 | C/T | T/C | C/A | NA | 0.37 |
| 24-341-1195 | 19GAR1-24 | C/T | T/C | C/A | NA | 0.32 |

Marker validation using germplasm from GAR1 and GAR3 not used in mapping.
142078_3898764 is heterozygous in only these accessions, the rest of the GAR1 and GAR3 accessions as well as the elites are all homozygous reference (T/T).
NA = no data.
*Plants marked "elite" were elite clones, not part of a seed lot.

When checking GAR2 data for marker 142078_3920202, the surrounding linkage map haplotype at 51.333 cM was found to include 6 additional SNP markers (142078_3619082, 142078_3638408, 142078_3700082, un111551_73_74, 142078_3828790, 142078_3898764, 142078_3920202; Table 7). Whereas marker 142078_3898764 segregates in GAR2, marker 142078_3894722 is monomorphic in this F2 population. Total Varin as well as Varin Ratio averages were similar for both heterozygous and homozygous reference allele for this haplotype (Table 7). Another observation from the GAR2 mapping results is that the effect of this marker is not as strong as observed in GAR1 and GAR3. This indicates that GAR1 and GAR3 are expected to have additional genetics which increase the Total Varin values.

Discovery of Five Additional Markers

In order to discover markers and genes that contribute to high Total THCV, Total Varin, and Varin Ratio levels in addition to KR/FABG, germplasm testing positive for the homozygous alternative allele (A/A) or heterozygous (C/A) genotype for 142078_3920202 was evaluated for Total THCV, Total Varin, and Varin Ratio.

In total 191 accessions from 21 seed lots with 142078_3920202 A/A or C/A were evaluated for Total THCV, Total Varin, and Varin Ratio in greenhouse and field in 2019, 2020, and 2021 (Table 8). This set includes 37 accessions (11 seed lots; top 11 rows in Table 8) from the initial data from GAR1 and GAR3 used to map the KR markers.

TABLE 7

| 142078_3894722 | 142078_3920202 | 142078_3898764 | Accession count | Varin Ratio | Total Varin average (%) | Total Varin range (%) |
|---|---|---|---|---|---|---|
| NA | CC | TT | 25 | 0.009 | 0.12 | 0-0.25 |
| NA | CA | TC | 69 | 0.020 | 0.22 | 0.06-0.59 |
| NA | AA | CC | 33 | 0.022 | 0.23 | 0.12-0.39 |

GAR2 values for marker 142078_3920202, 142078_3898764 and 142078_3894722 (NA = marker monomorphic in GAR2).

TABLE 8

| Seed lot | Total Varin (%) Avg | Total Varin (%) Min | Total Varin (%) Max | Varin Ratio Avg | Varin Ratio Min | Varin Ratio Max | Accession Count |
|---|---|---|---|---|---|---|---|
| 19GAR1-3 | 0.69 | 0.63 | 0.79 | 0.05 | 0.04 | 0.05 | 4 |
| 19GAR1-24 | 0.33 | 0.30 | 0.37 | 0.02 | 0.02 | 0.03 | 3 |
| 19GAR1-25 | 0.59 | 0.26 | 0.77 | 0.03 | 0.02 | 0.05 | 3 |
| 19GAR1-27 | 0.66 | 0.54 | 0.82 | 0.04 | 0.03 | 0.06 | 3 |
| 19GAR1-47 | 0.24 | 0.13 | 0.36 | 0.02 | 0.01 | 0.02 | 4 |
| 19GAR1-49 | 0.20 | 0.20 | 0.21 | 0.01 | 0.01 | 0.01 | 3 |
| 19GAR1-56 | 0.07 | 0.00 | 0.14 | 0.01 | 0.00 | 0.02 | 2 |
| 19GAR3-95 | 0.62 | 0.41 | 0.91 | 0.04 | 0.03 | 0.04 | 4 |
| 19GAR3-116 | 0.59 | 0.33 | 0.74 | 0.03 | 0.02 | 0.04 | 4 |
| 19GAR3-117 | 0.42 | 0.35 | 0.56 | 0.03 | 0.03 | 0.03 | 4 |
| 19GAR3-118 | 0.15 | 0.00 | 0.25 | 0.01 | 0.00 | 0.02 | 3 |
| 20TP1B-1008 | 1.14 | 1.12 | 1.16 | 0.06 | 0.05 | 0.06 | 2 |
| 20TP1B-1017 | 0.87 | 0.52 | 1.21 | 0.04 | 0.03 | 0.05 | 2 |
| 19AMTY-3 | 0.00 | 0.00 | 0.00 | 0.00 | 0.00 | 0.00 | 2 |
| 19AMTY-5 | 0.00 | 0.00 | 0.00 | 0.00 | 0.00 | 0.00 | 3 |
| 20VLP2-4 | 1.18 | 0.50 | 2.37 | 0.20 | 0.08 | 0.67 | 11 |
| 19GAR2-133 | 0.13 | 0.00 | 0.25 | 0.01 | 0.00 | 0.02 | 68 |
| 19AMTY-7 | 0.00 | 0.00 | 0.00 | 0.00 | 0.00 | 0.00 | 2 |

TABLE 8-continued

| Seed lot | Total Varin (%) Avg | Total Varin (%) Min | Total Varin (%) Max | Varin Ratio Avg | Varin Ratio Min | Varin Ratio Max | Accession Count |
|---|---|---|---|---|---|---|---|
| 20VLP2-11 | 0.50 | 0.21 | 0.80 | 0.08 | 0.06 | 0.10 | 6 |
| 20VLP2-3 | 0.20 | 0.00 | 0.40 | 0.02 | 0.00 | 0.05 | 2 |
| 21VLP5-1 | 2.20 | 0.46 | 11.60 | 0.76 | 0.00 | 3.85 | 56 |

Seed lots with accessions that are homozygous alternate allele or heterozygous for the KR marker 142078_3920202 used for the discovery of additional genetic factors contributing to high levels of Total THCV, Total Varin and/or Varin Ratio.

All 191 accessions were genotyped with an Illumina bead array. After filtering for known low quality SNPs, less than 10% missing data, and minor allele frequency greater than 1%, 35,813 SNPs remained for analysis. Mapping was performed through NAM (see previous section about association mapping) of Total THCV, Total Varin as well as Varin Ratio based on all 191 accessions with seed lot (Table 8) as family structure.

Figure 3:
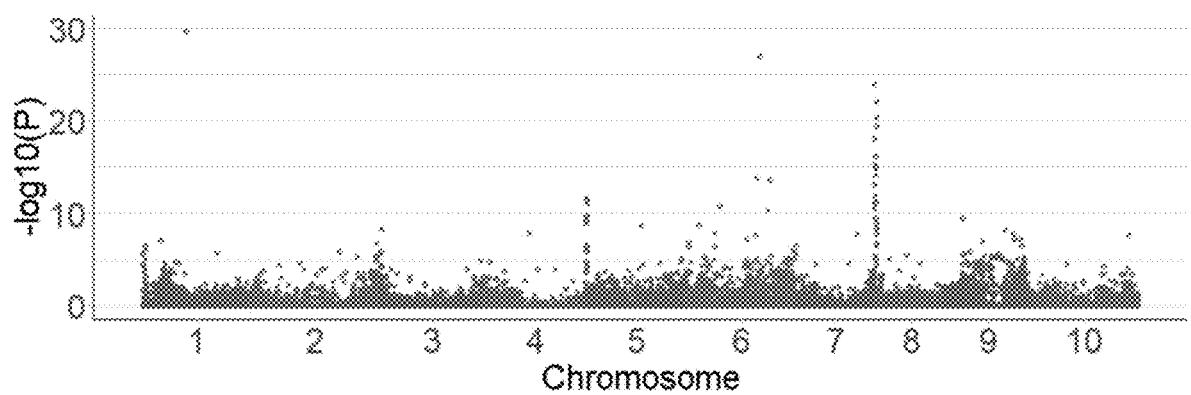
FIG. 3 illustrates −10 log p-values from Total Varin NAM based on 191 accessions from 21 diverse seed lots with KR marker 142078_3920202 homozygous alternate allele or heterozygous (x-axis: positions on the Abacus reference genome version CsaAba2; chromosome 10 is the X chromosome).

NAM results for Total Varin show strong associations for SNPs on chromosomes 1, 4, 6, and 7 with a total of 77 significantly associated SNPs (<1.4E-06 Bonferroni multi-test correction threshold; FIG. 3; Table 2 SEQ IDs 63-101). Significant associations for Total THCV (66 SNPs) overlapped with all significant associations observed in NAM for Total Varin, however associations were in general weaker as compared to NAM of Total Varin (five SNPs showed stronger associations with Total THCV as compared to Total Varin). NAM of Total THCV identified nine additional significantly associated SNPs (Table 2 SEQ IDs 234-242). NAM results for Varin Ratio show stronger associations (with 142 SNPs) at the same locations on chromosomes 1, 4, and 7; 48 of the significantly associated SNPs overlapped with the 77 significantly associated SNPs with Total Varin (Table 2 SEQ IDs 102-233).

SNP markers with strongest associations include SNP marker 142225_852 located at position 33,426,602 on chromosome 1 (CsaAba2 reference genome), which is associated with Total THCV, Total Varin, and Varin Ratio with p-values 1.23E-20, 1.86E-30, and 3.16E-49, respectively.

The SNP marker with the most significant association with Total THCV, Total Varin, and Varin Ratio on chromosome 4 (p-values 8.91E-09, 2.00E-12 and 1.20E-13, respectively), 41488_308754, is located at position 80,072,595 (CsaAba2 reference genome).

The SNP marker with the most significant association with Total THCV and Total Varin (p-values 1.00E-23 and 1.07E-27, respectively) on chromosome 6, 393_150329, is located at position 56,278,544 (CsaAba2 reference genome). This SNP marker displayed non-significant association with Varin Ratio (p-value=3.89E-05).

The strong association on chromosome 7 consists of two SNP markers most significantly associated with the phenotypes: 140868_29987 and 140868_8332, which are located at positions 62,971,551 and 62,993,205, respectively on chromosome 7 (CsaAba2 reference genome) and are associated with Total THCV with p-values 4.27E-18 and 1.48E-16, respectively. Total Varin association with 140868_29987 and 140868_8332 resulted in p-values 8.71E-23 and 3.89E-21, respectively. These two SNP markers are associated with Varin Ratio with p-values 5.13E-55 and 3.63E-52, respectively.

Next, haplotypes surrounding these four SNP markers were identified. The nearest non-significant SNP flanking 142225_852 on chromosome 1 is 141915_1321 and is located inside Berberine Bridge Enzyme-Like 24 (BBE24; position 33,423,461; p-value=1 for Total THCV, Total Varin, and Varin Ratio), however, its low minor allele frequency makes it a less reliable SNP. The next nearest non-significant SNP is 143920_1429 is located inside Flavone 3'-O-methyltransferase 1 (OMT1; position 33,409,265; p-value for Total THCV=4.37E-01; Total Varin=1.35E-01; p-value for Varin Ratio=7.59E-01). The nearest SNP flanking 142225_852 on the other side is 142470_18320 (position 33,483,608; p-value=1 for Total THCV, Total Varin, and Varin Ratio). As a result, the haplotype surrounding 142225_852 ranges between SNPs 143920_1429 and 142470_18320, spanning the genomic region between positions 33,409,265-33,483,608. This haplotype contains two candidate genes: BBE24 (142225_852 is 0.3 kb downstream of this gene) and OMT1 (142225_852 is 11.5 kb upstream of this gene) (Table 9).

The nearest non-significant SNPs flanking 41488_308754 on chromosome 4 are 141488_306945 for Total THCV and Total Varin (position 80,070,786; p-values 1 and 5.50E-02, respectively) and 141488_298707 (position 80,062,548; p-value=3.24E-02) for Varin Ratio. The nearest non-significant SNP flanking the other side of 41488_308754 is 141488_322143 (position 80,085,984; p-value=3.63E-01 for Total THCV, p-value=1.91E-01 for Total Varin, and p-value=1 for Varin Ratio). As a result the haplotype surrounding 41488_308754 is flanked by SNPs 141488_298707 and 141488_322143, spanning a genomic region on chromosome 4 between positions 80,062,548-80,085,984. This region contains three candidate genes: Fatty Acyl-ACP Thioesterases B (FATB; 41488_308754 is 0.1 kb upstream of this gene), Pentatricopeptide repeat-containing protein AT1G22960, mitochondrial (41488_308754 is 2.8 kb downstream of this gene), Origin of Replication Complex subunit 4 (ORC4; 41488_308754 is 6.4 downstream of this gene) (Table 9).

The nearest non-significant SNPs flanking 393_150329 on chromosome 6 are 393_185365 (position 56,236,381; p=2.57E-03 for Total THCV, p-value=1.58E-03 for Total Varin, p-value=1 for Varin Ratio) and 393_52202 (position 56,394,257; p-value=1 for both Total THCV and Total Varin; p-value=3.55E-01 for Varin Ratio). As a result, the haplotype surrounding 393_150329 ranges between SNPs 393_185365 and 393_52202, spanning the genomic region between positions 56,236,381-56,394,257). This region contains one candidate gene: DNA repair and meiosis protein (MRE11; 393_150329 is 113 kb upstream of this gene) (Table 9).

The nearest non-significant SNPs flanking 140868_29987 on chromosome 7 are 140868_47498 (position 62,954,094; p-value=1 for Total THCV, Total Varin, and Varin Ratio) and 140868_23884 (position 62,977,654; p-value=3.55E-01 for Total THCV, p-value=1 for both Total Varin and Varin Ratio). As a result, the haplotype surrounding 140868_29987 ranges between SNPs 140868_47498 and 140868_23884, spanning the genomic region between positions 62,954,094-62,977,654. This region contains three genes: Actin-related protein 2/3 complex subunit 2A/Distorted Trichomes 2 (ARPC2A/DIS2; 140868_29987 is 17.1 kb upstream of this gene), Membrane-bound transcription factor site-2 protease homolog (S2P; 140868_29987 is 12.3 kb downstream of this gene), and a CTP synthase family protein (140868_29987 is 3.0 kb upstream of this gene) (Table 9).

The nearest non-significant SNPs flanking 140868_8332 on chromosome 7 are 140868_14418 (position 62,987,118; p-value=1 for Total THCV, Total Varin, and Varin Ratio) and 140868_2816 (position 62,998,721; 5.5 kb upstream of 140868_8332; p-value=3.18E-01 for Total THCV, p-value=1 for both Total Varin and Varin Ratio), respectively. As a result, the haplotype surrounding 140868_8332 ranges between SNPs 140868_14418 and 140868_2816, spanning the genomic region between positions 62,987,118-62,998,721. This region contains four candidate genes: Aromatic aminotransferase ISS1 (ISS1; 140868_8332 is located 5.9 kb downstream of this gene), a hypothetical protein (140868_8332 is located 3.2 kb upstream of this gene), Pentatricopeptide repeat-containing protein AT1G33350 (PCMP-E57; 140868_8332 is located inside this gene), G-type lectin S-receptor-like serine/threonine-protein kinase SD1-29 (SD129; 140868_8332 is located 2.6 kb upstream of this gene) (Table 9).

TABLE 9

| Corresponding sequence ID | SNP marker | Candidate gene | Chrom. | Position (bp) | Reference allele | Alternate allele | Beneficial genotype |
|---|---|---|---|---|---|---|---|
| SEQ ID NO: 104 | 142225_852 | BBE24 | 1 | 33,426,602 | G | C | G/C, C/C |
| SEQ ID NO: 1 | 142078_3920202 | KR | 4 | 72,717,623 | C | A | C/A, A/A |
| SEQ ID NO: 120 | 141488_308754 | FATB | 4 | 80,072,595 | A | G | A/G, G/G |
| SEQ ID NO: 92 | 393_150329 | na* | 6 | 56,278,544 | T | C | T/C, C/C |
| SEQ ID NO: 190 | 140868_29987 | ARPC2A | 7 | 62,971,551 | C | T | C/T, T/T |
| SEQ ID NO: 192 | 140868_8332 | ISS1 | 7 | 62,993,205 | G | A | G/A, A/A |

Six main varin SNP markers.
First column: SNP ID, second column: SNP marker, third column: candidate gene containing flanking marker used for validation, fourth column: chromosome of the Abacus reference genome (version CsaAba2) SNP marker is located on, fifth column: position on Abacus reference genome (version CsaAba2), sixth column: reference allele in the Abacus reference genome, seventh column: alternate allele, eight column: beneficial genotype contributing to high levels of Total THCV, Total Varin, and/or Varin Ratio (except for the KR/FabG SNP marker all other SNP markers segregated for homozygous reference allele and heterozygous genotypes, it is expected that homozygous alternate allele genotypes have a similar beneficial effect as heterozgyous genotypes on varin production).
*No flanking marker in a candidate gene, main marker is located in a gene desert in the Abacus CsaAba2 reference genome.

Accessions with highest levels of Total THCV, Total Varin, and Varin Ratio had either homozygous alternate or heterozygous genotypes for the six varin markers (Table 10). Accessions with lower levels of Total THCV, Total Varin, and Varin Ratio have fewer of these six markers with homozygous alternate or heterozygous genotypes and more with homozygous reference allele genotypes. It is expected that the markers that have the heterozygous genotype as beneficial genotype also have the homozygous alternate genotype as beneficial genotype as would be expected for dominant inheritance (Table 2 and 10).

TABLE 10

| Accession | Total THCV | Total Varin | Varin Ratio | KR (142078_3920202) | FATB (141488_308754) | ARPC2A (140868_29987) | ISS1 (140868_8332) | BBE24 (142225_852) | (393_150329) |
|---|---|---|---|---|---|---|---|---|---|
| 21VLP5-1-18 | 6.68 | 11.60 | 3.48 | B | X | X | X | X | X |
| 21VLP5-1-207 | 3.60 | 6.26 | 2.78 | B | A | X | X | X | A |
| 21VLP5-1-261 | 3.25 | 6.24 | 3.27 | B | X | X | X | X | A |
| 21VLP5-1-59 | 2.19 | 3.26 | 0.38 | B | X | A | A | A | A |
| 21VLP5-1-120 | 0.92 | 1.60 | 0.20 | B | A | A | A | A | A |
| 21VLP5-1-208 | 0.00 | 1.08 | 0.13 | X | X | A | A | A | A |
| 21VLP5-1-201 | 0.69 | 1.11 | 0.10 | A | A | A | X | U | U |

Examples of varin marker genotypes in a seed lot segregating for Total THCV, Total Varin, and Varin Ratio.
The majority of this seed lot was selected for the KR SNP marker 142078_3920202 to be homozygous alternative allele; one heterozygous and one homozygous reference allele accession were included for comparison.
First column: accession ID, second-fourth columns: Total THCV, Total Varin and Varin Ratio in flower collected at 56 days after onset of flowering.
Fifth-tenth columns: genotypes for the six varin markers (A = homozygous reference allele, X = heterozygous, B = homozygous alternate allele, U = missing data).

Validation of these six varin markers was performed in the progeny of crosses between a high varin (Total Varin=5.4% one week prior to full maturity) parent and five lower varin (Total Varin ranging between <LOQ-1.2% at maturity) parents. The high varin variety and three of the low varin varieties were not used in mapping (NAM). The parents as well as the progeny were genotyped with an Illumina bead array. The high varin variety had the beneficial genotype for five out of the six markers: it was heterozygous for four of the six markers, homozygous alternate allele for 142078_3920202 (KR/FABG), and homozygous reference allele for 140868_29987 (ARPC2A/DIS2). However, the SNP located inside the ARPC2A/DIS2 candidate gene was heterozygous (140868_47498). It is expected that in the high varin parent a recombination event between the marker and the candidate gene disrupted the association. As a result, it was decided to use for validation both the main markers (Table 9) and their flanking markers located inside candidate genes. The high varin parent had the beneficial genotype for all flanking markers except for 141915_1321 (which is inside BBE24 and had missing data; Table 11). The lower varin parents had beneficial genotypes for 2-4 markers (including flanking markers; Table 11)

marker with missing data were removed from further analysis resulting in 34 accessions for HPLC analysis. Accessions were sampled for flower (cola) at an early flowering stage (33 days after 12:12 light flip). Because of flowering time variation, samples varied in developmental stage with later flowering plants producing smaller flowers with more leaves that are difficult to separate from the flower tissue. Increased flower leafiness results in reduced cannabinoid and varin levels in the tested sample since leaves contain lower levels of varins and cannabinoids as compared to flowers. As a result, flower samples were grouped into three categories: very leafy with small flowers, leafy with larger flowers, and well defined flowers with minimum leafiness.

The number of candidate genes (main and/or flanking markers) with beneficial genotypes in the progeny of the crosses ranged between 3-5. Accessions with highest Total Varin, Total THCV, and Varin Ratio (corrected for flower developmental stage at time of sampling) had (in addition to the beneficial genotypes for KR and FATB) the beneficial genotype for the ARPC2A marker 140868_47498 and both ISS1 markers (Table 12). Accessions with lower Total Varin, Total THCV, and Varin Ratio lacked this combination of markers, but had different combinations of the other markers (Table 12). From past experiments (in a different genetic background) it was determined that Total Varin >2% in leafy

TABLE 11

| Accession | Total THCV | Total Varin | Varin Ratio | desert (393_150329) | KR (142078_3894722) | KR (142078_3920202) | FATB (141488_306945) |
|---|---|---|---|---|---|---|---|
| 21TX1-60 | 5.40 | 5.40 | 1.00 | X | B | B | X |
| 21TX1-62 | 0.91 | 0.91 | 0.04 | A | B | X | A |
| 21TX1-65 | 0.91 | 0.91 | 0.04 | A | B | B | A |
| 21TX1-21* | 1.16 | 1.16 | 0.05 | A | B | X | A |
| 21TX1-59 | 0.00 | 0.00 | 0.00 | A | X | A | A |
| 21TX1-32* | 1.21 | 1.21 | 0.05 | A | B | X | A |

| Accession | FATB (141488_308754) | ARPC2A **(140868_47498) | ISS1 (140868_14418) | ISS1 (140868_8332) | BBE24 (141915_1321) | BBE24 (142225_852) |
|---|---|---|---|---|---|---|
| 21TX1-60 | X | X | X | X | U | X |
| 21TX1-62 | A | A | A | A | B | A |
| 21TX1-65 | A | A | A | A | B | A |
| 21TX1-21* | A | A | X | X | X | A |
| 21TX1-59 | A | A | A | X | U | U |
| 21TX1-32* | A | A | A | A | X | A |

Chemotype (based on flower at maturity) and marker genotype of the parents of the progenies used for marker validation.
*Accessions were used in mapping (NAM).
**Marker 140868_29987 (ARPC2A) was not used in validation because it was monomorphic for the reference allele in all parents.

Accessions from the progeny of these crosses were selected to have at least the beneficial genotype for the KR marker, focusing on maximizing the number of markers with beneficial genotype (n=44). Accessions with more than one flower samples at the early flowering stage results in >5% Total Varin at maturity. This indicates that the majority of these haplotypes are expected to produce >5% Total Varin (Total THCV) in the tested genetic backgrounds at maturity.

TABLE 12

| Haplotype | Stage | Population | Total Varin | Total THCV | Varin Ratio | Count* |
|---|---|---|---|---|---|---|
| KR_FATB_ARPC2A_ISS1full | defined flower | 21TX1-60 × 21 | 8.10 | 8.03 | 1.17 | 1 |
| KR_FATB_ISS1full_BBE24 | defined flower | 21TX1-60 × 21 | 2.97 | 2.97 | 0.37 | 2 |
| KR_ISS1_BBE24 | defined flower | 21TX1-60 × 21 | 2.64 | 2.64 | 0.25 | 2 |
| KR_FATB_ISS1_BBE24 | defined flower | 21TX1-60 × 21 | 2.55 | 2.55 | 0.24 | 1 |
| KR_ISS1_BBE24 | defined flower | 21TX1-60 × 32 | 3.44 | 3.44 | 0.67 | 2 |
| KR_FATB_ISS1_BBE24 | defined flower | 21TX1-60 × 59 | 2.96 | 2.96 | 0.30 | 2 |
| KR_FATB_ISS1_BBE24 | defined flower | 21TX1-60 × 65 | 1.75 | 1.75 | 0.24 | 1 |
| KR_FATB_ARPC2A_ISS1full | leafy | 21TX1-60 × 21 | 4.88 | 4.88 | 0.84 | 2 |
| KR_ISS1_BBE24 | leafy | 21TX1-60 × 21 | 2.47 | 2.47 | 0.30 | 2 |
| desert_KR_ISS1_BBE24 | leafy | 21TX1-60 × 59 | 3.13 | 1.45 | 0.32 | 1 |
| desert_KR_FATB_ISS1_BBE24 | leafy | 21TX1-60 × 59 | 2.48 | 2.48 | 0.33 | 2 |
| KR_ISS1_BBE24 | leafy | 21TX1-60 × 59 | 2.10 | 2.10 | 0.24 | 5 |
| KR_FATB_ISS1_BBE24 | leafy | 21TX1-60 × 59 | 1.84 | 1.84 | 0.30 | 5 |
| KR_FATB_ARPC2A_ISS1 | leafy | 21TX1-60 × 62 | 2.56 | 2.56 | 0.62 | 1 |
| KR_FATB_ISS1full_BBE24 | very leafy | 21TX1-60 × 21 | 2.57 | 2.57 | 0.43 | 2 |
| KR_ISS1full_BBE24 | very leafy | 21TX1-60 × 21 | 2.02 | 2.02 | 0.40 | 1 |
| desert_KR_FATB_ISS1_BBE24 | very leafy | 21TX1-60 × 62 | 1.91 | 1.91 | 0.38 | 2 |

Averages for Total Varin (%), Total THCV (%), and Varin Ratio per haplotype, flowering stage at time of sampling for HPLC analysis, and population.
A candidate gene is listed in the haplotype if one or both of the markers associated with the gene have the beneficial genotype.
For 393_150329 there is no flanking marker in a candidate gene because the marker is located in a gene desert on the Abacus reference genome; instead of a candidate gene identifier the word "desert" is used for this marker.
For ISS1 a distinction was made between a single marker (referred to as "ISS1") or both markers (referred to as "ISS1full").
*Number of accessions with the same haplotype per flowering stage.

Example 2—Discovery of *Cannabis* Total THCV Genetic Variants

Finola is a hemp variety with intermediate varin amounts (Total CBDV=Total Varin=0.74%; Pavlovic et al. 2019, Front. Plant Sci. 10: 1265) of the same order of magnitude as the highest levels of Total Varin observed in GAR1 and GA3. Finola has the homozygous alternate allele genotype (A/A) at marker 142078_3920202, which is associated with increased Total Varin content. This variety is heterozygous (C/T) for marker 142078_3894722 and homozygous reference (T/T) for marker 142078_3898764.

TABLE 13

Table 13 provides a listing of the markers for the present invention, which are located at position 26 of each respective sequence:

| SEQ ID NO | Description/SNP ID | Sequence |
|---|---|---|
| SEQ ID NO: 1 | 142078_3920202 | AACAAATCAATGACCAACTCAACAACAGCAACAA CGGTATTTGAGATGGAG |
| SEQ ID NO: 2 | 142078_3625974 | AAGACTAAAACACAGAGAAGAAAGTAATAGTCCT AAAGGAGAAGAAGAAAA |
| SEQ ID NO: 3 | 142078_3550154 | ACAAGTAGGTGATGATATAATTGCATTGCTTCAG CAGGGGAGAAAATTTGA |
| SEQ ID NO: 4 | 142078_4766558 | CTGTGGAGCTGCGGTTGTATTTGGTGAGTAATTC TATGATTTTGAGTATAA |
| SEQ ID NO: 5 | 142078_1326143 | AAGATTTGAAGGAGAGATTGGATAGAAAAACAAG AGGTAAGCCTTAGACCT |
| SEQ ID NO: 6 | 142078_1210539 | GGATGACGATGCCACCGTTGATGAAGACTCTGTC GCCGGAGTCCATGGTGA |
| SEQ ID NO: 7 | 142193_1677355 | AGAGCCTTGACCATCAACAACACCATTGCCTTGA ATAGTGAAATTATTGAT |
| SEQ ID NO: 8 | 75806_4137 | GGGGAAAACAAAATTGGAGGCCACGTGGAAGCCA AAATTAAATTTGTGGAG |
| SEQ ID NO: 9 | 142078_3253223 | CACACCTTAAATACAACAATCACACAAAGAATCA AATTTCACCATTGGAGC |
| SEQ ID NO: 10 | Cannabis.v1_scf1667-61642_101 | AAAAGATATATGTGTAATGTAATGTCACCAGCTT CTCATCTTATATACGTA |
| SEQ ID NO: 11 | Cannabis.v1_scf5183-21792_100 | ACATGTGTTTGGTTTAAATTAAGGGGAAGATAAC CATTAGAGAAGAATTGA |
| SEQ ID NO: 12 | 142078_577614 | GCTGCTCTACAAAATTCAGTACCCTGTCCTGTCC ATTAATTTGGCTTTGGG |

TABLE 13-continued

Table 13 provides a listing of the markers for the present invention, which are located at position 26 of each respective sequence:

| SEQ ID NO | Description/SNP ID | Sequence |
|---|---|---|
| SEQ ID NO: 13 | 142078_3704759 | TAGAGGTAGAGAATCATAAACATGAGACGGCATT CTCTCTTGGTAAGGACA |
| SEQ ID NO: 14 | 142078_1847669 | TTCCAAGCATCATTGGCATCATACAGCCAATAAT AGCTGCCAGACTTAACT |
| SEQ ID NO: 15 | 142078_292186 | GGCGCCATGGGTGTGTGGAGTTCGGCAACTTCCA GACCAGTGGAGCTTCCA |
| SEQ ID NO: 16 | 105108_3515 | CAAAGGAAAACAAAGTCCCCAACCTGGCCCTCAA TATCTCTACACTTCGTA |
| SEQ ID NO: 17 | 142193_1314778 | TTCACCAAGCTGTGTGATAGATCTCATGTGATGA AACTCACAAAATAAATT |
| SEQ ID NO: 18 | 142078_1437037 | GGACTTGGTTAGGATGTTTTACGGCGAATTGGGT AAGAAGAAAGATGGAAG |
| SEQ ID NO: 19 | 142498_504213 | AACTACTTTCTCAATAAAAGAAACTAAATACTA TAATATTATAGTTGTAT |
| SEQ ID NO: 20 | 141588_1041814 | ATCTAAATTGTAGTATTTTGCTAATGGTTGCTCT ATACATATGAGAGGTGA |
| SEQ ID NO: 21 | 141536_1732919 | ACCCTAAAGAAGGGACTTACATGAAACTTTTGGT TCTCCTTGGAAGATCTG |
| SEQ ID NO: 22 | 142593_2516791 | TTGTAGAAGCACCCAATATTATTTTGGCCTAATA TGAGATTGAGTTATTCT |
| SEQ ID NO: 23 | 142193_544418 | GTTTTACATTTGGTAGAAACCAAGACCCCAAGAG GTGGTTTCTTGAAAGTA |
| SEQ ID NO: 24 | 137716_10170 | GAGCTGTCCCCGCTTAGTGGAGCGCGACCCCCAA AGTTGACATATGCAATG |
| SEQ ID NO: 25 | 141066_96797 | AAATATTCTTACTGCTCCAACGGTTGGGAGGCTA ATGAGTTTCCCTCGTCC |
| SEQ ID NO: 26 | 141066_131854 | GTCGCTCGGGCATTAGCTAATCCAAAGGACATGA CTAGGAATTCACAGTGC |
| SEQ ID NO: 27 | 142078_2113828 | GCGAATTTCCTAAAAGTTTGGTTCATCAGGTTGT GTAATTGGCTGAAGCTC |
| SEQ ID NO: 28 | 142078_2101225 | GAGCTTAGTGAATCCTTGCCTAAGGCCGATTTTG ATTGAGGAGAATTCCTT |
| SEQ ID NO: 29 | Cannabis.v1_scf1614-34746_100 | AAATTTGAATAACATGTTGGCTTATTGGTGATGG CTCTCTTGTTACTAGCA |
| SEQ ID NO: 30 | 142078_2120695 | TTAACCTCATATTCGTACACTTGAGAGAGACTGG CCGTGCATCAACTTCGG |
| SEQ ID NO: 31 | 142078_2108403 | TAAAGACAAACACTGGGAACGTGTAGTAATTGAG ACTGATAGCATGATATC |
| SEQ ID NO: 32 | 107657_19015 | ATTAATATAGTAATGGTTTACACTAGGTGCACAA CCATTCCATCATTCTGA |
| SEQ ID NO: 33 | 141539_889015 | AATCCAAGCTAGCTAATGTTTTGCATGCCAATGA GCTTTCAAGACGTTTAA |
| SEQ ID NO: 34 | 142593_2843997 | CCCTTTTATTGGGCCTGATTATGGATTGAGCTTT TTATATTTTAATGAA |
| SEQ ID NO: 35 | 142498_946327 | ACTAATGATTCTTCTAGGTCAATGAATCAAATT TTATGCCCAAAGATTGT |
| SEQ ID NO: 36 | Cannabis.v1_scf1899-49684_101 | ACTCCAAAATTGCAGAACTAGGCAGAGGAGATGG AGCAGATGGATTTCCAA |
| SEQ ID NO: 37 | 141588_698298 | TTTTGGAGAGGTGATTAAACTTTTCGAGGAGCTG ACTGCTGCAAACCCTTC |

TABLE 13-continued

Table 13 provides a listing of the markers for the present invention, which are located at position 26 of each respective sequence:

| SEQ ID NO | Description/SNP ID | Sequence |
|---|---|---|
| SEQ ID NO: 38 | 141911_847832 | AAGTTTTAAAAAATTTGGTGTGCCCGTGTGGGGT CTGTGGAAGTTATGGAA |
| SEQ ID NO: 39 | 141588_872012 | TTGCTCACATCCTTGTCCATGGTTCCTGTCAGCC ACTTGAAGTCTGGCTGA |
| SEQ ID NO: 40 | Cannabis.v1_scf276-285935_100 | GGTAAGTTAATTGTATTTCCCATCAGTTCTTTTT TTGCTATGTAACATGTT |
| SEQ ID NO: 41 | 141588_843688 | TACTTATTTGGAAAGTAGCACCATTGCCGACAAG GCAAACTTGGTGCGAGT |
| SEQ ID NO: 42 | 141588_732634 | TATCAGATTACCCCTCTATGTTGGAGAAGATCCA ACTCTGATGGCACAGTT |
| SEQ ID NO: 43 | 141588_650796 | TGAAGGCCTATGCCCTCGACCGTCCGAAGAAGGT GCAGAAGATAAATGCAT |
| SEQ ID NO: 44 | Cannabis.v1_scf3658-4502_101 | CAAGTGACAGATCAAATGCATGTGACTCACCTGA CACCTTGGCTGGCATAG |
| SEQ ID NO: 45 | 141588_811200 | ACATACTTGGTAGTAAATCTAGATCCTGGTAAAA TATTTCCAACAGCTAAA |
| SEQ ID NO: 46 | 141750_1008206 | ATTTGATTTCTATTTATTGTTATTTGTAGTATCC AACATGACTATGACCAA |
| SEQ ID NO: 47 | 141539_692672 | AACAAATGAAGTCTCCTCTAATCTATATTAATAG CTAGCTAGTTGGTTTTC |
| SEQ ID NO: 48 | 141588_1407653 | GTTTGTGCACTTTTCCATTTAAAAAGTTGCTTTG TTTCAGTTTGTAAGCTT |
| SEQ ID NO: 49 | 142250_1987729 | ATACCAGAGCTTCTTCTTGAAATTGGAAGGTGCC ACAGGCCACCCGGTCAT |
| SEQ ID NO: 50 | 142593_2671993 | TGTTTTCTAGTTTAAATTTCGATTGTCGTTGCCT TCTCCTAGCTTGCCTAG |
| SEQ ID NO: 51 | 142593_2666596 | GTTGACTAGAGCTCAGTCTATGAATTATCATATT TATAAATATACATAAAT |
| SEQ ID NO: 52 | 142593_2561020 | CTGGCCTATTAAGCTGATGGACATCAAGACCACA AGATGCCAATTCGGAAG |
| SEQ ID NO: 53 | 142593_2694605 | CTTGACCAAGAATCCACTTTGCCATTCTCCTATG TCTTTTATCCACTCTTG |
| SEQ ID NO: 54 | 141840_416132 | CTAGAAGTGCACTGACCAAACCCCCAACACTTAT CTCAAGTAGCCATTGTT |
| SEQ ID NO: 55 | 142250_2234807 | AACACATGAATGTACGATTCTATTTGGGTTGTGG TAGATCAATTTACGAAT |
| SEQ ID NO: 56 | 142250_2380876 | TTGTGTCTCGCATGTATCATTGGCTCAGGTTTGC AAAATGCAACCCTATGC |
| SEQ ID NO: 57 | 141840_61026 | AAAGGAGAGTGAAACAGTGAATGTGAAAAACCTT TTTCTCTCAGTTTCCGC |
| SEQ ID NO: 58 | 141840_125137 | GGTGTCGATGTAATTTCCATAATCACCACAATCA AACCAAAGCCTTCCTTT |
| SEQ ID NO: 59 | 141840_271843 | AGATGCAGTAGTCACCAAAATTACAAAGAAAACA ATTTGGTTATGTATATT |
| SEQ ID NO: 60 | 141840_131915 | TTAATTTCATTAATTATTAGAAAATAAATAAAAT AAGTTGACTATAATATT |
| SEQ ID NO: 61 | 142250_2293974 | GGGTATAACAATTTCCCCTTAAAATGTCTTTATT AATAAAAAGTGCTTTTA |
| SEQ ID NO: 62 | 142078_3894722 | TCCAGTTATGTAACTTGCAGCAGGACCAAGTGCC AAAAATTCCACTAGCCC |

TABLE 13-continued

Table 13 provides a listing of the markers for the present invention, which are located at position 26 of each respective sequence:

| SEQ ID NO | Description/SNP ID | Sequence |
|---|---|---|
| SEQ ID NO: 63 | 90_425860 | CAGGAATACCTTGCCATTTGATATGCTCTTGAGG CTTACAGGAAGTCTTGA |
| SEQ ID NO: 64 | 90_516765 | ATAAATTATGAGGTTGACTTTGGATTGGGTCAAC CTATTTATGTTGGACCT |
| SEQ ID NO: 65 | 293_1299949 | AAGAAGGCCATTTATAATTCACTACTGGGACAAC AAAAGCAACACCTGATA |
| SEQ ID NO: 66 | 142372_3159807 | ATGCTACTAGGAATATTTGATTACAACCCAAACT AATATAAGATAGTAGTA |
| SEQ ID NO: 67 | 142372_2749182 | CAGCTTGTTCCTCAACAAACTTCACAAGCTTCTC CAGATACCGATCTCCGG |
| SEQ ID NO: 68 | 142250_8699831 | TGTGTACATTCAGGTTTATATATGTGCATGCCTC TCATACTGCTAAACTTC |
| SEQ ID NO: 69 | 141488_326503 | TGTGGTGGATAAAGACAGGCCCCCATCTCATCAA TCTGTTCGCCGATTTTT |
| SEQ ID NO: 70 | 141488_351566 | GGAACACTTTATTGGCTAAAAAGGTCCCTACTT GAGAAAATACTTTACCT |
| SEQ ID NO: 71 | 141488_432025 | TGACCCATAAGATTTCAAGTCAGCCGTGTCGATA ATAAATTATATTAAGGA |
| SEQ ID NO: 72 | 141488_461840 | ACTCAATTATTTATAGTATCCTATTTCCAATTTC CACTTAGAACACTCCCA |
| SEQ ID NO: 73 | 141488_577527 | TTCACAATTGGATTCTACTCATCGTCGTTGTGGT GCTTTTCGGTGCTGTTG |
| SEQ ID NO: 74 | 141488_582366 | TAAACGACTTTTAAGACTTAATCTTCCATTTGAT TGGACAATACAAACAAA |
| SEQ ID NO: 75 | 141488_588603 | AATTTGATAAAACCATCCACCTATTCTTTTAACA TAATTAATTATATCTTT |
| SEQ ID NO: 76 | 141488_592975 | ATTTATCTGGCGCCCCTAAGAGAGTCTCTGGTAA TTTAGAATCTATGGGAT |
| SEQ ID NO: 77 | 141488_657452 | TTCTACAGAATACATAATTGGACTGCTTTTTTTG TTATACAAACTTGGATC |
| SEQ ID NO: 78 | 141488_685576 | TTTGCTTATAATCGGAGTTATTGTTCTGTTTCAG GGCCTGAAAATATGGGG |
| SEQ ID NO: 79 | 141488_718654 | CACGACATGAAAAATGTGTTCTTAAGCACGACAC GTTACGAGAAGTACAAA |
| SEQ ID NO: 80 | 141488_759240 | TACTTCTTCTGTCTTATGTGAAACTTTCTTTAAC TGCATTTCATTTTGACA |
| SEQ ID NO: 81 | 141488_804059 | TTGCAAATAAGATGATATATTAAGTCTTGAACTT GGAAATAACAAGTTAGA |
| SEQ ID NO: 82 | 125246_20932 | GATGATTGCTGATCCTATGACAAAAGGCTTGCTA CCTCATAAATTCAAGGA |
| SEQ ID NO: 83 | 199557_20501 | AAAAAAGACGAATTTTAGCACGACACACGGTATA ATGCTACAAATTAGCAC |
| SEQ ID NO: 84 | 103533_2046 | CATCTAAAAACTCTTGTACTACTTTGATATCTTC AGGTAGAATTGACTCAG |
| SEQ ID NO: 85 | 139181_57592 | AGAAAGTCATGGTTCTCATTTAGTAAACATGATG TCACAATAATCCAGAGA |
| SEQ ID NO: 86 | 120967_267 | AGATGTTTCATGAAGCATTTGGTTGCGTCATCTA CCTATCAGCTAGAGAAG |
| SEQ ID NO: 87 | 77309117 | CACATGATATTGATGTTTCAATTTGATAATCATG TTTTATATACTGCACTG |

TABLE 13-continued

Table 13 provides a listing of the markers for the present invention, which are located at position 26 of each respective sequence:

| SEQ ID NO | Description/SNP ID | Sequence |
| --- | --- | --- |
| SEQ ID NO: 88 | 141826_380714 | AGTGCAACACTAAAGAAAGCCCAATAGAGAGGTTCAAAGCAGTTCTTGCAT |
| SEQ ID NO: 89 | 14114518419 | TAAGAGAAACCATTCTATGTAATTAACCCCTATAAAATGGTGGTTGCATCT |
| SEQ ID NO: 90 | 133613_11055 | GGCCTGCCAGCCCCCTAGAAGTGGCATGTTCATCATTTCATTGTCCCTCCT |
| SEQ ID NO: 91 | 140442_11150 | AAAGCACCCCTGGCCAAGGACTTTTTTTCTATGCAACCTGCTTTGACCCTC |
| SEQ ID NO: 92 | 393_150329 | CCAAATCAAGCATGCAAAACATCATTTTCTTCCCAAAATTTCCAAGAAACT |
| SEQ ID NO: 93 | 231_15997 | AGTGTTGCATGAAATATGTTATTTGAGCATCTATTAATGGTTAGTAATCCT |
| SEQ ID NO: 94 | 123683_23309 | CATAGTTGCTCAACCTTAACTTTGCATTTACCTACACATGCAAACAATAAC |
| SEQ ID NO: 95 | 321_12940 | CTCAATAAAAATTCAATCTTTCTTCTACAGCTCACTCTTCCCATAACCAGA |
| SEQ ID NO: 96 | 81097_814 | TAGTTAGGCTAATTATAGTTTTTGGTTTCGAACTTTAATATGTATTAGATC |
| SEQ ID NO: 97 | 424_7576172 | TAATAATATGAGTTAACACAATAAAGAACTATCTAATCAATCTCAAGTTTT |
| SEQ ID NO: 98 | 424_12451946 | CCAGTTCAGTCATAAAGGCACTTATAAGGGCAGAATTTGAGACTTTAATCT |
| SEQ ID NO: 99 | 141768_2132603 | GGTTGTTATGACTTGTATATGTTGTATATTATGTGTTGTATGCTAACGTGT |
| SEQ ID NO: 100 | 142335_191216 | GTGTTTGAAAGAGTACTCATACCACGTATAATTTTTTGTGTCAAGTTTTAA |
| SEQ ID NO: 101 | 142316_804337 | TTGACAAGTGCAACTGAGATTCATACTCTCTATGAAACTCGGCTTGCTCGA |
| SEQ ID NO: 102 | 140807_1546 | AACTAGACAAAACTTGCAATGTAATATCAGTCCTCCACATTAGTAATAAAC |
| SEQ ID NO: 103 | 369_303184 | TAGTGGGTAATTATATATGTTATGAGATTTATCGTCTTACCATGTAAAGGA |
| SEQ ID NO: 104 | 142225_852 | GCCCTATAATATAAAATGATGACCTGAAATGGATATGAAAGAAGAATGGCA |
| SEQ ID NO: 105 | 141673_1924981 | TGTTGTCAATATTAACCATGATCCCGACCCAGGTTTCTTGAGGTATGACTC |
| SEQ ID NO: 106 | 141677_25193 | GGTCACTCACTGTGAACGCCACGTTAAAAATTGAAGTTAATGCATCTAGCT |
| SEQ ID NO: 107 | 132136_9628 | GCGCACCACTAAATAACTTTAGAAGTCCAAATCGTATTTTCCCAACACAGA |
| SEQ ID NO: 108 | 167_1167836 | TTCAAGTTGTATCTCTTGTGCATACTGAGTTGTTGGCATTCGATCTCGCAA |
| SEQ ID NO: 109 | 142353_26553 | AGTATGGCAAAATAAGCCAACCAATGCCTCGTATCTTTATGCATTTGCGGT |
| SEQ ID NO: 110 | 116167_2793 | TTGAGAAAATATCAACTTAGACACTGGGTCCCCCTTCTAGCCCTTTGGAAA |
| SEQ ID NO: 111 | 411_1266367 | GAAAAAATACATTTGCCATTGCTCAACACAAGCATCATCACAGTATCTATG |
| SEQ ID NO: 112 | 142193_4943614 | GGTGCAATATTAGCTGGGTTAACAATTATATGGTTTCTTTTCGAAGTAGCT |

TABLE 13-continued

Table 13 provides a listing of the markers for the present invention, which are located at position 26 of each respective sequence:

| SEQ ID NO | Description/SNP ID | Sequence |
|---|---|---|
| SEQ ID NO: 113 | 141488_70104 | TCTGTTTGGTTCCTGAGAAAATTTGTCAGGGTTT GATTTTTTAGGTATTAA |
| SEQ ID NO: 114 | 129891_10941 | GATTGATAAAGAGACAAATTAAACAAAAATATTA AAGACTATTAAATAGTA |
| SEQ ID NO: 115 | 141488_247424 | GCACTAAGTTTTGAAGTGTTATTTGAAGCATGGT AGAAAGATTATCTTTTT |
| SEQ ID NO: 116 | Cannabis.v1_scf1353.38456_101 | AATAAATCTGAAAAAGTGGAAAAAATCTGAGTTA GTAGAGTAGATTTCTGG |
| SEQ ID NO: 117 | 141488_253018 | TCTCATTACAATCGATGAAAGCAATTGATTCTCT TAGGATGGAGTTCTATT |
| SEQ ID NO: 118 | 141488_264076 | GGGCTTAAGTAGAGGCCTAGCTCGTTTTATCTCA AACACGATCTCATGACA |
| SEQ ID NO: 119 | 141488_287391 | TCCGGATCTTGGTGTTGGTAATGCAGTTTAGGCA TTTTGGCATTTTTTATT |
| SEQ ID NO: 120 | 141488_308754 | GCAATGGACGGAAGTGCCTAAGAAAATTTGAGTA AAGAAAGATATTTTATG |
| SEQ ID NO: 121 | 141488_415560 | CCATTAGAAAAAAAGGGAAAAACACCCTAAACCC TAAAGCAGGCATGAAAA |
| SEQ ID NO: 122 | 141488_528550 | AAAGTAGAATTGGGAGTTTTGACTCAAAATGTAA ATTTGTGAGTTGACAGT |
| SEQ ID NO: 123 | 141488_718654 | CACGACATGAAAAATGTGTTCTTAAGCACGACAC GTTACGAGAAGTACAAA |
| SEQ ID NO: 124 | 141488_748628 | TAAAATTTTATTCTGAATGCCAAAACAGATACAT GTGTATCGATATACCCA |
| SEQ ID NO: 125 | 141488_796227 | CACCCTAGAAAGCCTCCACGATTCTCTTGCAGTC GTAGAAGAAGGCGCAAT |
| SEQ ID NO: 126 | 197_1007670 | ATAGATAGAAGGGGTGAATGAGAAACTCAAATG AAAAATAAATAATATTT |
| SEQ ID NO: 127 | 113321_6502 | AACTATATATAAAACACAAATATAAGGAATTATA TTTAGTTTCAAATTTTT |
| SEQ ID NO: 128 | 280_107725 | AGATTTTATAAATGCTCCAAATGGGTTGTCTAAG GTGTCTGCAGCAGTAAA |
| SEQ ID NO: 129 | 141477_415245 | GCATCTTTTTTCCCTTATGGATACACAAGCAATT CAACGAAGGAAAAGATA |
| SEQ ID NO: 130 | 321_137337 | ACTTGGGCCCTTCATTGTTTCTATATAAAATTGC TCGACCTATTTTGCATT |
| SEQ ID NO: 131 | 141801_365489 | CATGTAGAGGCACCTACGGCAGGATCCGTCATCT TGGCAGGAATTCCATCA |
| SEQ ID NO: 132 | 141440_188532 | CAACTGCCCAAATGGAAGGGACTGAAGTTCGAGA GTATTCATCAACCTAAA |
| SEQ ID NO: 133 | 142465_697275 | AAGAAGGGGAAAAGAAGTCATACGTGACCACT AACACTCCCCTAGTGTG |
| SEQ ID NO: 134 | Cannabis.v1_scf3835.18137_100 | AGGCAAGACAACCCTCCAACATAGCGAGTATCCA AAAGACCTTAGTCAGAG |
| SEQ ID NO: 135 | 142593_598766 | ACAAAACATATTAAAAGAAGTGAGGTGAAGAGA TGACCTAAGAAGTGAAA |
| SEQ ID NO: 136 | 142593_696671 | ACCAAGAAATTAGTGATAAGAAAACAGCTTCGGA ATTTATTTTCCAGTAAC |
| SEQ ID NO: 137 | 142593_825954 | TCTTCTCCAAACTAAAAGCAAAATACTGAGGAAA CTCCTTAACCTCTTCCA |

TABLE 13-continued

Table 13 provides a listing of the markers for the present invention, which are located at position 26 of each respective sequence:

| SEQ ID NO | Description/SNP ID | Sequence |
| --- | --- | --- |
| SEQ ID NO: 138 | un248038_76_77 | TACTGCCAACATTTGTTGGAACAGCCGGAGATGA CGCCCCAGCAGAGCTGA |
| SEQ ID NO: 139 | 142593_953088 | CCCCGAAGCTGTATATGTTGTAATTATTCATTAG TTTCACTACCACAACAT |
| SEQ ID NQ: 140 | 142593_1001463 | CATTTTAGTTCAACTGCAGCATTAGCTAATGCTC TGAACTCACTTTCTGTA |
| SEQ ID NO: 141 | 135838_2796 | ATGAAATTTATTATTTTGTCTTTTGTTGTAAAAG TATCACAAATAATGAAC |
| SEQ ID NO: 142 | 142593_1138108 | CTTATCAAAATTTTGGTAAACAACTACATTAATT TAGAGTCTTATGAAAAT |
| SEQ ID NO: 143 | 142593_1283036 | TTTGGCAATTAATGATATTTAGTTAAAGCACCTA ATCCATGACAGAATTGA |
| SEQ ID NO: 144 | 142593_1291062 | ATATTTCTTTCCTTCTAAGGATAGAGTAAGCTTT TGACTACGTGGGCCAAT |
| SEQ ID NO: 145 | 142593_1302135 | CCACGTGTATTAGAGATCAAAAGATGATGAACTT TTGTGGGAATTGTGTTC |
| SEQ ID NO: 146 | 142593_1336537 | TCGTGCTAAATGGGTTAGTAGTCTAATTAGTGAA CTCTGGCCTAAAGTAGA |
| SEQ ID NO: 147 | 142593_1387225 | GTGCTTCTCAAGGCTTTTTCTTCAGGAATTTTGA TGCTCTTGCTAGTCGTT |
| SEQ ID NO: 148 | 142593_1427427 | TATATAACTACTATTCTTCCTCTACCATTCTACT TATTTTCTTTTTGATAT |
| SEQ ID NO: 149 | 142593_1664077 | TAAACTATCTCAAGCCGATCACTGCAAACACAAA ATACCATGTCACAAAAC |
| SEQ ID NQ: 150 | 142593_1693931 | TTGCTAACATGGGAGCAAATATGGCTTCTTATGA TGCTGCAGTTCTCAACG |
| SEQ ID NO: 151 | 142593_1891259 | TCCAAGGTACATTAAATGGGTTTCAGGGTACATT AGATGGATTTCAAGGTA |
| SEQ ID NO: 152 | 142593_2106455 | TGAGTTTGGTTTGCAACCATGGAGCCCTAATAAG CTTCCCTACCCCTCAGG |
| SEQ ID NO: 153 | 142593_2160414 | GAAATATTTACAAATTTGCCACAACGTTTCGTT GACTTGGAAAAACAACC |
| SEQ ID NO: 154 | 142593_2265578 | TGTCCGTGCCACCTGCGTCGCAGACGATAGATCT TCAGACTTTGTACAACG |
| SEQ ID NO: 155 | 142593_2376437 | AGACTTACACCGTCCTCGAGGAACGTCATGAGCT CCCGCTTGTGAGCCGCC |
| SEQ ID NO: 156 | 142593_2565374 | CCCATTATCATCACCACTGCATAAAGTCAATGCA ACCATTCAAATAGCAAT |
| SEQ ID NO: 157 | 142593_2588342 | AACAAATTGCTGCTATGATTAGGCCGAAAACCAA GTAAAATGAGGCAACAA |
| SEQ ID NO: 158 | 142593_2772843 | TCTAATCATACAAAATGTCACCCCAGTCACTGCA TAAACCACATTTTCTCC |
| SEQ ID NO: 159 | 142593_2805919 | AAGATTCACGCAAGAAAATTATATGTAGTATCAC TATTCATTCGAATGGTA |
| SEQ ID NQ: 160 | 142593_2824003 | ATCCTTAAACTTGGAGTTGAGCATAAGGATGCAT TATTCTCTTCACTTCAT |
| SEQ ID NO: 161 | 142593_2836644 | TCACAGCACTCATTTTCTCATACTTTCCGGCTTT GCCATAAGAATCCAAGA |
| SEQ ID NO: 162 | 141840_10828 | GGTGTCGCTTTGTCTTAATGATCTTTTGGCTATA ATAGATTGCTTATCTGT |

TABLE 13-continued

Table 13 provides a listing of the markers for the present invention, which are located at position 26 of each respective sequence:

| SEQ ID NO | Description/SNP ID | Sequence |
| --- | --- | --- |
| SEQ ID NO: 163 | 141840_28460 | TATTGGACAATTTTTGTTGTCAATATGGTCATAG TGTCAACTAAACCATTG |
| SEQ ID NO: 164 | 141840_51814 | TTAAAATAAAAGATAAGTTGGACAATATTCTAAA TTAATTAGGTGTCAAAT |
| SEQ ID NO: 165 | un259474_79_80 | CACTTCATTGTTAGAAATCGGTCTTTGATGTCAC CCTGATTCAAGAAAAGA |
| SEQ ID NO: 166 | 141840_239615 | TACATCACCCAAGCAAATTAGCTCCAGGGGCGAC TTTCATTGCTTCAAATT |
| SEQ ID NO: 167 | 141840_325947 | CTATAATTTTGAACACGTCATAGCCTTACACGTG GCACCAAAACGTCTTAC |
| SEQ ID NO: 168 | 141840_372430 | TTAACAAGAAATGTAACTCCAATGCTCACGGAAT AGTGAATGACCGAGTCA |
| SEQ ID NO: 169 | 141840_378162 | AACAAGAGTATAACTCAGGATACTCAAAAGGGA AGAAGATGATTTTCAAA |
| SEQ ID NQ: 170 | 141840_385292 | CGGTGTGGCGACTATTAGCCTCGTATGCCATGGC AAGCCATATTTGAATCT |
| SEQ ID NO: 171 | 141840_441895 | GTTGTCTCGGGCTGAATCGGCCGGCCAACGCGCC GCCTGGATTGGACGAAA |
| SEQ ID NO: 172 | 141840_681190 | GCTTCTTAAATTTTTGTGGGGTTTTTGTGACAAG GAAGGAGGTGGAGAAAT |
| SEQ ID NO: 173 | 141840_691350 | GAGTTCATGGACAGTATTGGTGTAAGTTGTGATG CAATTGCTCGTACAGGA |
| SEQ ID NO: 174 | 141840_707354 | CCCAAACAAACAAATAATAAGTAATATTAATTAA TCCTAACAGAGTGGGTT |
| SEQ ID NO: 175 | 141840_721728 | TAGGACGGTTACCTAATTTTCATACAATTAATTA TAAAAGGAGAAGTTTGT |
| SEQ ID NO: 176 | 141840_906772 | TATTTGAGGGAGGCATAGACCCAGTGGTGGCTGA AGAGTGGATGAGTTGCA |
| SEQ ID NO: 177 | 102155_5292 | AACATAGTATTTAGTCACAAGTTGTTACTAATTT AATTTTAGTCACAACAA |
| SEQ ID NO: 178 | 109486_529 | GGCGAGCTGGTGATAATTTGATTGCCAAAATGAA AGAGAGATCTTTAAATT |
| SEQ ID NO: 179 | 140868_225626 | TTTGTGCTCGATCTTCATCAATGTCGCTAGCAGT GGTTGCAAAAGGATGAT |
| SEQ ID NQ: 180 | 140868_220724 | TTCTTGAATTGTGATCCCAAATTTGGATCCACAA GCTCCATTATATCTCCC |
| SEQ ID NO: 181 | 140868_216359 | TATTTGCAAGGCTATTGTTTTCCATGTACTCATA AACCAGCAACAATTGCT |
| SEQ ID NO: 182 | 140868_202351 | CATAACAAAGCTACTTTAATCATTCGAAATACTT CTTCGTGGTTGAACTCG |
| SEQ ID NO: 183 | 140868_196317 | ATTTCCATGCAAAGAAGAAGTAGTAAGAATACAA TTACATCATGGAGTATA |
| SEQ ID NO: 184 | 140868_179511 | TTTCTGTTCATGCTAGTTTAGGTAAGTGGTGGGA GTGTCTTAAGCTTTTTG |
| SEQ ID NO: 185 | 140868_156260 | CGTCGATTATGGGCTGACGCGTTTCTCTCCATGG GCCCTACTACCCTCCAA |
| SEQ ID NO: 186 | 140868_121287 | TATACAGACTATAGTCAATATTAAATCATTATTA TTAATTTCATATATAAT |
| SEQ ID NO: 187 | 140868_107435 | ATCCAGCTTCTACTAACAATGGTAAGTTTTATAC CAAATATCATAATTTCT |

TABLE 13-continued

Table 13 provides a listing of the markers for the present invention, which are located at position 26 of each respective sequence:

| SEQ ID NO | Description/SNP ID | Sequence |
| --- | --- | --- |
| SEQ ID NO: 188 | 140868_103015 | AGTTGATGGCGTTCATGGCGTCGTCGATTCGATTCCTCTGGAATTGGTAGT |
| SEQ ID NO: 189 | 140868_60566 | CCTTCTGACAGCTCGGAGGAAGGATGCTCGTTCGGTGAAGATTAAGAGAAG |
| SEQ ID NO: 190 | 140868_29987 | TTTTATTATTTTTTCACACAATTAACAATGAGACTCTTTAATAACAACAAC |
| SEQ ID NO: 191 | 140868_21724 | ATCTGGGTTGTTCTGTTCCTTCTCATGGAAATCTTGAAAAATGGGCTGTTC |
| SEQ ID NO: 192 | 140868_8332 | TTGGGTTGGTCCCAAAACCGGATTTGAGAATGTGGGTGTGGAGCAGAGGTG |
| SEQ ID NO: 193 | 142415_1123082 | ATAAATGAAATTCTCTATTTCCCTCAATACAATTTGATTATTTGATCCATA |
| SEQ ID NO: 194 | 424_10555780 | TAGCAAGAGAATCAGTTGCAGCGTTCGTAAGACGCTCTTTCAAGGTGTTCT |
| SEQ ID NO: 195 | 424_11546598 | GGTTCAGGACAAGGAGAAAGAGACTGAGTAAGATTAGGCATAGCAAAGAAA |
| SEQ ID NO: 196 | 424_11882159 | GGTGTAAAATTGTTACCATTTTGTTGTTTTTATTTTCAGTGTGAGTTGTTT |
| SEQ ID NO: 197 | 424_12133507 | AAATAGCAGTAGCTATAGCTAGCTTGTTATTATATTAGGCATGTGCATTGC |
| SEQ ID NO: 198 | 424_14302177 | ACACTGCTCCCAATCCAAAGGTAGAGGATCTTTCAGTTGAAGATCAACGCT |
| SEQ ID NO: 199 | 141768_2047138 | ATTGGAATAGTAAGTCTTTAGCCTTCGTTAACAGCATATTGGCAAACACTA |
| SEQ ID NO: 200 | 141239_980212 | GTGTGATTATGTCAAAGAAAAAGACAAACATGTTGGATATATTTTACCAGG |
| SEQ ID NO: 201 | 188092_144 | ATTTGTATTGTCCTTTCCAACTACCCTTTAGGTACCTATGATGATGATGGG |
| SEQ ID NO: 202 | 141687_78697 | AATAATTGTTGGAATTATTTTACCAGGATCTTAGATCTACTCACAAGTATG |
| SEQ ID NO: 203 | 140742_308066 | GTCATGATTGTATATTAAAATCTCTCATAATAAAAATTAAAGATATATGTA |
| SEQ ID NO: 204 | 142335_5939 | CATCAGACCGAGAAAACTTGGACACCAGGCTTGTTCGAAGCCGCACGCACC |
| SEQ ID NO: 205 | 142335_954059 | AAATTTAATTAATTTTCTAATATTTAAAATAATTAAATTATGTACCCAATA |
| SEQ ID NO: 206 | 142316_299798 | TCTTTAAATATTTGATAATGAGAATCCCATTTTGTTTTAGCACGTCATACG |
| SEQ ID NO: 207 | 142316_538783 | GTGCTTAAAATCCCATCCAAACTCAAGACCCACAATTTTTATATAATATAT |
| SEQ ID NO: 208 | 118107_6746 | GAGTTTCTTGTGAGATGGCGGCGTTGATTGAAGTTTGGATAGTAGAAAGTG |
| SEQ ID NO: 209 | 123724_2165 | TTGTTGTTGGTGAATCTAATCAGTGGTTATTTAGTTTGAGAAAATAAAAAT |
| SEQ ID NO: 210 | 142494_7010731 | TTAGTTTAAAAGGGATGAAAATATAGAATGAAGTCTTATTATCCATGCATT |
| SEQ ID NO: 211 | 142293_8350062 | CATCATTCTCATATTATTACTAAAAGGCTCATGGCTAAAGATACTAGTCAC |
| SEQ ID NO: 212 | 129510_2422 | TTTTAAAATACAAGGTACTAAATAAGCATTATTAAAATACAGGGTACAAA |

TABLE 13-continued

Table 13 provides a listing of the markers for the present invention, which are located at position 26 of each respective sequence:

| SEQ ID NO | Description/SNP ID | Sequence |
|---|---|---|
| SEQ ID NO: 213 | 141076_101280 | AATGTGCGACCGAGACAAGGTGTAGTCGCGCACT ATGCATGGCATAGCAAA |
| SEQ ID NO: 214 | 142299_1600906 | AAAATCAGCAAGCTGCTCATTTACTTCTTTGTAA GAGTGTGTGTGTTGTGT |
| SEQ ID NO: 215 | 421_5909899 | TGGTTTTTATTTATTTATTTTTTTGAGAAAAAAA CTTCAAAACCCACCTTT |
| SEQ ID NO: 216 | 421_5526104 | ACAAAAACTTAACCTGCAGAGATGGGTACCCACA AGTACCCACCCCAAATG |
| SEQ ID NO: 217 | 421_4052952 | GTGGAGGAAATTTCTTGGCTTTCTCAAGTGAGGC CCCAAAGAAGTGTGTGT |
| SEQ ID NO: 218 | 135235_11613 | GGAGAGCTAGCTATAGCTAATTAAAATTTTAAAT TATGAATAATAAACAA |
| SEQ ID NO: 219 | 421_2973420 | TGGTATAATCTATTTTGAACAAATGAGATGATCT AGCATAAACGTTTTATT |
| SEQ ID NO: 220 | 421_2789258 | CATGAACACGTAGATAAGTAATCAACAGTTAAGA TTAGACAAGAAATGTG |
| SEQ ID NO: 221 | 421_2780311 | CTCTAAGAGATGGAATTGAAGAAAACCTCAAGGA CTGAGAATGGAGCTGCT |
| SEQ ID NO: 222 | 421_2585261 | ATGGATCTTGGTTTAGTATAGAGTAAAATCTCAA GTAACTTGTGCTTGGTA |
| SEQ ID NO: 223 | 421_2280631 | AATGGTGCAGTGCAGAGGGTGGTGTGGCATGTGC TACAGTAACAGGCCCAG |
| SEQ ID NO: 224 | 421_1598102 | ATATCAGGCATTGTGGTAGAGAAAACGTTCAATC ATAATAGAAAACAACAA |
| SEQ ID NO: 225 | 421_1390091 | TGCATCGAGGCTGCAAAGTTTGTTTTTCTTGATC GAACAAGGGGTTGTTG |
| SEQ ID NO: 226 | 170_555139 | CTCGCATTCTCAATCTCCTCTCCATTCATGGTAG ATCTCCAACTTCTCTGA |
| SEQ ID NO: 227 | 170_4513981 | CCCGAGCCATATGCCACAGAGAACAACTTTTTGT CTCTTCAAGGTACACGC |
| SEQ ID NO: 228 | 170_4459590 | TCTCTCTCTCTTCAGACATATACCCTTAGCTCCC CTATTATTTCTACTATC |
| SEQ ID NO: 229 | 170_4368831 | GAAATCCAGTCCAAAGGCACAAAACTGTTTCTTC AAGAATGTACCACCTAA |
| SEQ ID NO: 230 | 170_4338498 | ACGTACCGGGAAAGAATTTTCCGATGATACGAAG GATCTTGCGACCTTGTT |
| SEQ ID NO: 231 | 170_4279882 | ATCAATGAAGAAGAAGGGTCATCCAAAACAAGGG GTTTCAACTGAGCTAAC |
| SEQ ID NO: 232 | 170_3444229 | TCATGGGAAAAGTGATGGAAGTTTTTAAACCCGG GGCTGTGGTTCTTCAGT |
| SEQ ID NO: 233 | 170_3363670 | TGGCTGGCTAGACAAGGATGCCATTGTTATAAAT TAATGATGTTGATCAAT |
| SEQ ID NO: 234 | 139860_60165 | CGTAAAATTTATTTTTAAAATATTAAAAATCATT TCTTACAGGCTGACCTA |
| SEQ ID NO: 235 | 171_21004641 | GTGGAGAGAAAAGCATAAGCAAATTTACAAATTT ACAAGTCAGCAAATTTT |
| SEQ ID NO: 236 | 142713_950507 | TTAAATATACTAATAAGAAAATGACACTTGGATA ATAACTTGAAACTTAAC |
| SEQ ID NO: 237 | 141356_780969 | ATTTTGAGAGAAAGAGATAGAGAGAGGGGGCGG GTTTGAGGCAAATGAAC |

TABLE 13-continued

Table 13 provides a listing of the markers for the present invention, which are located at position 26 of each respective sequence:

| SEQ ID NO | Description/SNP ID | Sequence |
| --- | --- | --- |
| SEQ ID NO: 238 | 141366_519971 | CTTTCGGAGAGAAAAAGAAGAAGTTCCAGACTCC CCAACTAAAGATTTTTT |
| SEQ ID NO: 239 | 199086_194 | GGACCCGAAAGCCCTGTCATCCCTCTAGGACCTA GAGAAGACCAAATCAAC |
| SEQ ID NO: 240 | 140726_195388 | CACTTCTTATTCGGTGTCATTCGATCAAGCTTTG TAAAAAACTTTGGTGGT |
| SEQ ID NO: 241 | 141318_196817 | GAAATGAATTATAAAAGTAGTGAGTAAGCAAAAC TTTCACAGCAGCCACAT |
| SEQ ID NO: 242 | 122751_1014 | TATAATCAATAGAATAAGATAGGACCTACTATTG TTTGTTTGTTCAACCAA |

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the invention as defined in the appended claims.

What is claimed is:

1. A method for selecting one or more *Cannabis* plants having modified varin activity, the method comprising:
   i) crossing a *Cannabis* plant having modified varin activity with another *Cannabis* plant to produce one or more F1 *Cannabis* progeny plants;
   (ii) obtaining a nucleic acid sample from the one or more F1 *Cannabis* progeny plants or their germplasm;
   (iii) screening the nucleic acids to detect one or more polymorphisms that are genetically linked to a varin activity trait loci,
   wherein the one or more polymorphisms comprise a polymorphism in the reference allele of the *Abacus Cannabis* CsaAba2 reference genome on chromosome 4 relative to position 72,717,623; 72,413,830; 72,330,901; 73,591,604; 72,070,492; 74,886,331; 72,386,361; 72,500,945; 72,692,194; 80,090,345; 80,115,357; 80,028,174; 80,051,232; or 80,072,595; or a polymorphism in the reference allele of the *Abacus Cannabis* reference genome version CsaAba2 on chromosome 7 relative to position 62,019,912; 62,034,938; 62,231,000; 62,387,493; 62,647,527; 62,737,982; 62,742,884; 62,747,249; 62,761,203; 62,767,237; 62,792,364; 62,815,617; 62,850,589; 62,866,162; 62,870,580; 62,941,027; 62,971,551; 62,979,814; or 62,993,205;
   (iv) selecting the one or more F1 *Cannabis* progeny plants comprising the one or more polymorphisms that are genetically linked to a varin activity trait loci; and
   (v) crossing the selected F1 *Cannabis* progeny plants to produce at least one additional progeny plant comprising the modified varin activity.

2. The method of claim 1, wherein the modified varin activity correlates to modified tetrahydrocannabivarin (THCV), tetrahydrocannabivarinic acid (THCVA), cannabidivarin (CBDV), cannabidivarinic acid (CBDVA), cannabigerivarin (CBGV), or cannabigerivarinic acid (CBGVA) levels.

3. The method of claim 1, wherein the selecting comprises marker assisted selection.

4. The method of claim 1, wherein the detecting comprises use of an oligonucleotide probe.

5. The method of claim 1, wherein the polymorphism on the *Abacus Cannabis* reference genome comprises:

(a) an A/C genotype at position 72,070,492 on chromosome 4;
(h) a T/C genotype at position 72,330,901 on chromosome 4;
(c) a G/C genotype at position 72,386,361 on chromosome 4;
(d) an A/G genotype at position 72,413,830 on chromosome 4;
(e) an A/A genotype at position 72,500,945 on chromosome 4;
(f) a T/T genotype at position 72,692,194 on chromosome 4;
(g) an A/A or C/A genotype at position 72,717,623 on chromosome 4;
(h) an A/A genotype at position 73,591,604 on chromosome 4;
(i) a C/C genotype at position 74,886,331 on chromosome 4;
(j) a T/C genotype at position 80,028,174 on chromosome 4;
(k) a G/C genotype at position 80,051,232 on chromosome 4;
(l) a G/G or A/G genotype at position 80,072,595 on chromosome 4;
(m) a T/C genotype at position 80,090,345 on chromosome 4;
(n) a T/A genotype at position 80.115,357 on chromosome 4;
(o) an A/C genotype at position 62,019,912 on chromosome 7;
(p) an A/C genotype at position 62,034)38 on chromosome 7;
(q) a G/T genotype at position 62,231,000 on chromosome 7;
(r) a T/T genotype at position 62,387,493 on chromosome 7;
(s) a C/G genotype at position 62,647,527 on chromosome 7;
(t) a G/G genotype at position 62,737,982 on chromosome 7;
(u) a G/A genotype at position 62,742,884 on chromosome 7;
(v) a G/A genotype at position 62,747,249 on chromosome 7;

(w) a G/T genotype at position 62,761,203 on chromosome 7;
(x) an A/A genotype at position 62,767,237 on chromosome 7;
(y) a G/A genotype at position 62,792,364 on chromosome 7;
(z) a T/C genotype at position 62,815,617 on chromosome 7;
(aa) a T/T genotype at position 62,850,589 on chromosome 7;
(bb) a G/G genotype at position 62,866,162 on chromosome 7;
(cc) a G/G genotype at position 62,870,580 on chromosome 7;
(dd) a G/G genotype at position 62,941,027 on chromosome 7;
(ee) a T/T or C/T genotype at position 62,971,551 on chromosome 7;
(ff) a T/C genotype at position 62,979,814 on chromosome 7; or
(gg) an A/A or G/A genotype at position 62,993,205 on chromosome 7.

6. The method of claim 1, wherein the crossing comprises selfing, sibling crossing, or backcrossing.

7. The method of claim 6, wherein the selfing, sibling crossing, or backcrossing comprises marker-assisted selection.

8. The method of claim 6, wherein the selfing, sibling crossing, or backcrossing comprises marker-assisted selection for at least two generations.

9. The method of claim 1, wherein the at least one additional progeny plant comprising the indicated modified varin activity is an F2-F7 progeny plant.

10. The method of claim 1, wherein the modified varin activity is an increase in THCV, CBGV, and/or CBDV levels.

* * * * *